(12) United States Patent
Liu et al.

(10) Patent No.: US 8,362,023 B2
(45) Date of Patent: Jan. 29, 2013

(54) PYRAZOLO PYRIMIDINES

(75) Inventors: Wenjian Liu, Beijing (CN); Kin-Chun Luk, North Caldwell, NJ (US); Xiaohu Zhang, Beijing (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/347,718

(22) Filed: Jan. 11, 2012

(65) Prior Publication Data

US 2012/0184508 A1  Jul. 19, 2012

Related U.S. Application Data

(63) Continuation of application No. PCT/CN2011/070383, filed on Jan. 19, 2011.

(51) Int. Cl.
| | |
|---|---|
| A61K 31/519 | (2006.01) |
| C07D 487/04 | (2006.01) |
| A61P 35/04 | (2006.01) |
| A61P 25/28 | (2006.01) |

(52) U.S. Cl. .................................... 514/262.1; 544/262
(58) Field of Classification Search .................. 544/262; 514/262.1
See application file for complete search history.

(56) References Cited

U.S. PATENT DOCUMENTS

| | | | |
|---|---|---|---|
| 7,217,710 B2 | 5/2007 | Adams et al. | |
| 7,435,731 B2 | 10/2008 | Arora et al. | |
| 7,452,880 B2 | 11/2008 | Arora et al. | |
| 7,563,799 B2 | 7/2009 | Billedeau et al. | |
| 2003/0235822 A1 | 12/2003 | Lokhor et al. | |
| 2004/0198751 A1 | 10/2004 | Adams et al. | |
| 2005/0197340 A1 | 9/2005 | Arora et al. | |
| 2005/0277655 A1 | 12/2005 | Ding et al. | |
| 2006/0009628 A1 | 1/2006 | Dempcy et al. | |
| 2006/0183900 A1 | 8/2006 | Huang et al. | |
| 2007/0179165 A1 | 8/2007 | Gyorkos et al. | |
| 2009/0131457 A1 | 5/2009 | Bruce et al. | |

FOREIGN PATENT DOCUMENTS

| | | |
|---|---|---|
| CN | 101555212 | 10/2009 |
| WO | 01/64958 | 9/2001 |
| WO | 03/029209 | 4/2003 |
| WO | 2005/028434 | 3/2005 |
| WO | 2005/085248 | 9/2005 |
| WO | 2005/121107 | 12/2005 |
| WO | 2006/063820 | 6/2006 |
| WO | 2007/023105 | 3/2007 |
| WO | 2007/023111 | 3/2007 |
| WO | 2007/136465 | 11/2007 |
| WO | 2008/047307 | 4/2008 |
| WO | 2008/098104 | 8/2008 |
| WO | 2009/126515 | 10/2009 |
| WO | 2009/128520 | 10/2009 |
| WO | 2010/003133 | 1/2010 |
| WO | 2011/068990 | 6/2011 |

OTHER PUBLICATIONS

Yang et al., "Carcinogenesis" 31(4):552-558 ( 2010).
Ansel et al., "Pharmaceutical Dosage Forms and Drug Delivery Systems":456-457 ( 1995).
Friedman et al., "Cancers" 2:1492-1512 ( 2010).
Kim, N., "Bioorganic & Medicinal Chemistry Letters" 16:3772-3776 ( 2006).
"English language Abstract corresponding to CN101555212", Oct. 14, 2009.
Kangmoon et al., "Cancer Research" 60:3631-3637 ( 2000).
"International Search Report PCT/EP2012/050545—mailed Apr. 5, 2012".
Southwick et al., "Heterocyclic Chemistry" 12:1199-1205 ( 1975).
Yoshida, K., "Biochemical Pharmacology" 76:1389-1394 ( 2008).
Ismail et al., "Egyptian J. Chem." 33:221-232 ( 1991).
Revesz et al., "Bioorg. Med. Chem." 16:262-266 ( 2006).
Deng et al., "Cancer Res." 66(8):4149-4158 ( 2006).
Koo et al., "Bioorganic & Medicinal Chem. Lett." 19:2324-2328 ( 2009).
Park et al., "Cell. Mol. Life Sci." 66:3235-3240 ( 2009).
Gao et al., "Cancer Biology & Therapy" 8(17):1671-1679 ( 2009).

*Primary Examiner* — Susanna Moore
(74) *Attorney, Agent, or Firm* — George W. Jonhston; Patricia S. Rocha-Tramaloni

(57) ABSTRACT

Compounds of formula and pharmaceutically acceptable salts thereof are described, as well as the pharmaceutical compositions containing said compounds and their pharmaceutically acceptable salts, and the use of the compounds and pharmaceutical compositions for the treatment, control or amelioration of proliferative diseases, including cancer, Down syndrome or early onset Alzheimer's disease.

22 Claims, No Drawings

PYRAZOLO PYRIMIDINES

PRIORITY TO RELATED APPLICATIONS

This application is a continuation of and claims priority from PCT/CN2011/070383, filed Jan. 19, 2011. The entire contents of the above-identified application is hereby incorporated by reference.

FIELD OF THE INVENTION

The present invention relates to pyrazolo[3,4-d]pyrimidines which act as inhibitors of DYRK1B and/or DYRK1A and are useful in the amelioration, treatment or control of cancer, especially solid tumors, or in the amelioration, treatment or control of Down syndrome or early onset Alzheimer's disease.

BACKGROUND OF THE INVENTION

Kinases are known to be important cellular enzymes that regulate cellular functions such as regulating cell division and proliferation. WO 2008/047307. Dual-specificity tyrosine-phosphorylation-regulated kinases (DYRKs) are a subfamily of protein kinases that have dual-specificity and are believed to play roles in cell proliferation and apoptosis induction. See, e.g., Kiyotsugu Yoshida, "Role for DYRK family kinases on regulation of apoptosis," Biochemical Pharmacology 76 (2008) pp 1389-1394; Jinghun Gao et al., "Mirk/Dyrk1B, a novel therapeutic target, mediates cells survival in non-small cell lung cancer cells," Cancer Biology & Therapy 8:17 (2009) pp. 1671-1679. DYRK1A is believed to be implicated in neural differentiation. Yoshida, id. at 1390. Over expression of this kinase is believed to be involved in Down syndrome and Alzheimer's disease. See Nam Kim, "Putative therapeutic agents for learning and memory deficits of people with Down syndrome," Bioorganic & Medicinal Chemistry Letters," 16 (2006) pp 3772-76 and Joongkyu Park et al, "Function and regulation of Dyrk1A: towards understanding Down syndrome," Cell. Mol. Life. Sci 66 (2009) pp 3235-3240. Thus, inhibition of this kinase is believed to be of benefit in controlling or ameliorating the effects of Down syndrome and early onset Alzheimer's disease. See, e.g., Kim, id; Park, id, and Kyung Koo et al., "QSAR analysis of pyrazolidine-3,5-diones derivatives as Dyrk1A inhibitors," Bioorganic & Medicinal Chemistry Letters 19 (2009) pp 2324-2328.

DYRK1B (also referred to as MIRK) mediates survival and differentiation in many tissues. It is believed to be implicated in certain cancers, particularly solid tumors. See, e.g., Gao, supra (lung cancer cells); Kangmoon Lee et al, "Mirk Protein Kinase is a Mitogen-activated Protein Kinase Substrate that Mediates Survival of Colon Cancer Cells", Cancer Research 60 (2000):3631-3637 and Xiaobing Deng et al, "The Kinase Mirk/Dyrk1B Mediates Cell Survival in a Pancreatic Ductal Adenocarcinoma," Cancer Res 66:8 (2006) pp 4149-58 (pancreatic cancer cells). Thus, inhibition of this kinase is believed to be of benefit in controlling or ameliorating cancer. See, Cao Yang et al, "The kinase Mirk is a potential therapeutic target in osteosarcoma," Carcinogenesis 31:4 (2010) pp 552-558 and Eileen Friedman, "The Kinase Mirk/dyrk1B: A Possible Therapeutic Target in Pancreatic Cancer," Cancers 2 (2010) 1492-1512.

SUMMARY OF THE INVENTION

One aspect of the invention is a compound of formula I

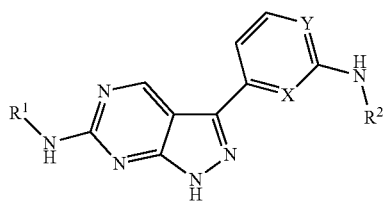

or a pharmaceutically acceptable salt thereof, wherein X, Y, $R^1$ and $R^2$ are as defined below.

The present invention also relates to pharmaceutical compositions comprising one or more compounds of the invention, or a pharmaceutically acceptable salt, and a pharmaceutically acceptable carrier or excipient.

The present invention further relates to a method of treating, ameliorating or controlling cancer, including specifically solid tumors, for example lung, pancreatic, colon, breast, bone and prostate cancers in a mammal, specifically a human, comprising administering to said mammal a therapeutically effective amount of a compound according to the invention or a pharmaceutically acceptable salt thereof.

The present invention further relates to a method of treating, ameliorating or controlling Down syndrome or Alzheimer's disease in a human, comprising administering to said human a therapeutically effective amount of a compound according to the invention or a pharmaceutically acceptable salt thereof.

DETAILED DESCRIPTION OF THE INVENTION

Definitions

As used herein, the following terms shall have the following definitions.

The terms "$C_{1-6}$ alkyl" or "$C_{1-4}$ alkyl" refer to straight- or branched-chain saturated hydrocarbon groups having from 1 to 6, or 1 to 4, carbon atoms, respectively. Examples of $C_{1-6}$ alkyl groups include, but are not limited to, methyl, ethyl, n-propyl, i-propyl, n-butyl, s-butyl, t-butyl, n-pentyl, and s-pentyl. Particular example for $C_{1-6}$ alkyl is methyl, ethyl and n-propyl. Particular example for $C_{1-4}$ alkyl is methyl, ethyl and n-propyl.

"Alkoxy, alkoxyl or lower alkoxy" refers to any of the above alkyl groups which is attached to the remainder of the molecule by an oxygen atom (RO—). Typical alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Aryl" means a substituted or unsubstituted monovalent, monocyclic or bicyclic, aromatic carboxylic hydrocarbon radical, preferably a 6-10 member aromatic ring system. Preferred aryl groups include, but are not limited to, phenyl, naphthyl, tolyl, and xylyl. Particular example for aryl is phenyl.

The term "cycloalkyl" as used herein means a substituted or unsubstituted stable monocyclic or polycyclic system which consists of carbon atoms only, all rings of which are saturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Particular example for cycloalkyl is cyclohexyl.

"Halogen" means Cl, F and Br. Particular example of halogen is F and Cl, most particularly Cl.

"Heteroaryl" means a substituted or unsubstituted aromatic heterocyclic ring system containing up to two rings. Preferred heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, triazolyl and tetrazolyl. Particular example of heteroaryl is thiophenyl.

In the case of a heteroaryl that is bicyclic it should be understood that one ring may be aryl while the other is heteroaryl and both may be independently substituted or unsubstituted.

"Hetero atom" means an atom selected from N, O and S.

"Heterocycle" or "heterocyclic ring" means a substituted or unsubstituted 5 to 10 membered, mono- or bicyclic, non-aromatic hydrocarbon, wherein 1 to 3 carbon atoms are replaced by a hetero atom selected from nitrogen, oxygen or sulfur atom. Examples include pyrrolidinyl, including pyrrolidin-1-yl, pyrrolidin-2-yl and pyrrolidin-3-yl; piperazinyl; piperidinyl; morpholinyl, including morpholin-4-yl; and the like, which in turn can be substituted. Particular examples of heterocyle are piperidinyl, piperazinyl, pyrrolidinyl and morpholinyl.

In the case of a heterocycle that is bicyclic it should be understood that one ring may be heterocycle while the other is cycloalkyl, and either or both may be independently substituted. An example of such a bicyclic heterocycle is 8-oxa-3-aza-bicyclo[3.2.1]octane.

Hydroxy or hydroxyl is a prefix indicating the presence of a monovalent —O—H group.

"$IC_{50}$" refers to the concentration of a particular compound required to inhibit 50% of a specific measured activity. $IC_{50}$ can be measured, inter alia, as is described subsequently in Examples 94 and 95.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Substituted," as in substituted alkyl, means that the substitution can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent.

In one embodiment, the present invention relates to compounds of formula I

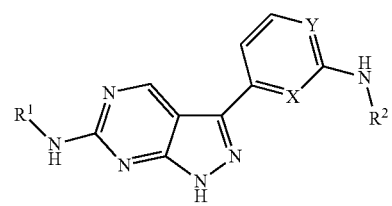

wherein

X and Y are independently selected from CH and N;

$R^1$ is selected from the group consisting of
(a) H,
(b) $C_{1-4}$ alkyl,
(c) $C_{1-4}$ alkyl substituted with up to 3 groups selected from cycloalkyl, heterocycle, $OR^3$, $NR^3R^4$ and CN,
(d) Aryl,
(e) Aryl substituted with up to three groups selected from $C_{1-4}$ alkyl, $OR^5$, $NR^5R^6$, halogen and CN,
(f) Heterocycle,
(g) Heterocycle substituted with up to three groups selected from $C_{1-4}$ alkyl, $OR^5$, $NR^5R^6$ and CN,
(h) Cycloalkyl, and
(i) Cycloalkyl substituted with up to three groups selected from $C_{1-4}$ alkyl, $OR^5$, $NR^5R^6$, halogen and CN;

$R^2$ is selected from the group consisting of
(a) $C_{1-6}$ alkyl and
(b) $C_{1-6}$ alkyl substituted by up to 3 groups selected from
aryl,
aryl substituted with Cl, F, $CH_3$, or $CF_3$,
heteroaryl,
cycloalkyl,
heterocycle,
OH,
$OCH_3$,
$NR^5R^6$, and
CN;

$R^3$ and $R^4$ are independently selected from the group
(a) H,
(b) $C_{1-4}$ alkyl, and
(c) $C_{1-4}$ alkyl substituted with up to three groups selected from cycloalkyl, heterocycle, OH, $OCH_3$, $NR^5R^6$ and CN; and $R^5$ and $R^6$ are independently selected from the group
(a) H and
(b) $C_{1-4}$ alkyl;
or a pharmaceutically acceptable salt thereof.

In another embodiment, the invention relates to compounds of formula Ia having the structure

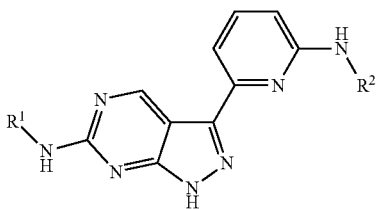

Ia wherein R¹ and R² are as defined above, or a pharmaceutically acceptable salt thereof.

In another embodiment, the invention relates to compounds of formula Ib having the structure

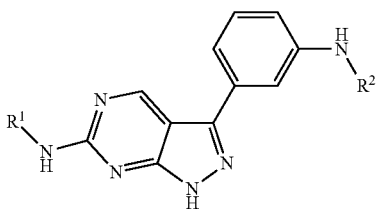

Ib wherein R¹ and R² are as defined above, or a pharmaceutically acceptable salt thereof.

In another embodiment, the invention relates to compounds of formula Ic

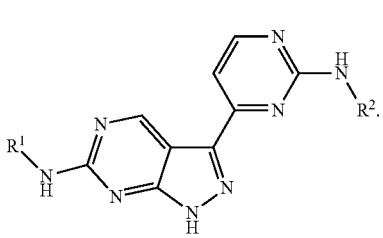

Ic

In another embodiment, the invention relates to compounds of formula I, including compounds of formulas Ia, Ib and Ic, wherein R¹ is $C_{1-4}$ alkyl, or a pharmaceutically acceptable salt thereof.

In another embodiment, the invention relates to compounds of formula I, including compounds of formulas Ia, Ib and Ic, wherein R¹ is $C_{1-4}$ alkyl that optionally is substituted with heterocycle, or a pharmaceutically acceptable salt thereof.

In another embodiment, the invention relates to compounds of formula I, including compounds of formulas Ia, Ib and Ic, wherein R¹ is $C_{1-4}$ alkyl that optionally is substituted with $OR^3$ or $NR^5R^6$, and R³ is H or $CH_3$, and R⁵ and R⁶ are independently $C_{1-4}$ alkyl, or a pharmaceutically acceptable salt thereof.

In another embodiment, the invention relates to compounds of formula I, including compounds of formulas Ia, Ib and Ic, wherein R¹ is cyclolakyl that optionally is substituted with $NR^5R^6$, specifically $NH_2$, or a pharmaceutically acceptable salt thereof.

Another embodiment of the invention relates to compounds of Formula I, including compounds of formulas Ia, Ib and Ic, wherein R¹ is as defined immediately above and R² is $C_{1-6}$ alkyl that optionally is substituted with aryl that itself optionally is substituted with Cl, F or $CF_3$, or a pharmaceutically acceptable salt thereof. In one embodiment the aryl is phenyl that optionally is substituted with Cl.

Another embodiment of the invention relates to compounds of Formula I, including compounds of formulas Ia, Ib and Ic, wherein R¹ is as defined immediately above and R² is $C_{1-6}$ alkyl that optionally is substituted with heteroaryl, including specifically a thiophene, or a pharmaceutically acceptable salt thereof.

Another embodiment of the invention relates to compounds of Formula I, including compounds of formulas Ia, Ib and Ic, wherein R¹ is as defined immediately above and R² is $C_{1-6}$ alkyl that optionally is substituted with heterocycle, or a pharmaceutically acceptable salt thereof.

Another embodiment of the invention relates to compounds of Formula I, including compounds of formulas Ia, Ib and Ic, wherein R¹ is as defined immediately above and R² is $C_{1-6}$ alkyl that optionally is substituted with $NR^5R^6$, or a pharmaceutically acceptable salt thereof. In one embodiment R⁵ and R⁶ are H.

Another embodiment of the invention relates to compounds of Formula I, including compounds of formulas Ia, Ib and Ic, wherein R¹ and R² are as defined immediately above and R³ and R⁴ are H or $CH_3$, or a pharmaceutically acceptable salt thereof.

Another embodiment of the invention relates to compounds of Formula I, including compounds of formulas Ia, Ib and Ic, wherein R¹, R², R³ and R⁴ are as defined immediately above and R⁵ and R⁶ are H or $CH_3$, or a pharmaceutically acceptable salt thereof.

It is contemplated herein that salts of compounds of formula I such as hydrochloride or trifluoroacetic acid salts include salts with multiple conjugates such as mono HCl, di-HCl, etc.

Compounds according to the invention include:

[3-(6-Benzylamino-pyridin-2-yl)-1H-pyrazolo[3,4-d]pyrimidin-6-yl]-(2-piperidin-1-yl-ethyl)-amine (Example 44);

[3-(6-Benzylamino-pyridin-2-yl)-1H-pyrazolo[3,4-d]pyrimidin-6-yl]-(2-morpholin-4-yl-ethyl)-amine (Example 45);

[3-(3-Benzylamino-phenyl)-1H-pyrazolo[3,4-d]pyrimidin-6-yl]-(2-morpholin-4-yl-ethyl)-amine (Example 46);

{3-[6-(3-Chloro-benzylamino)-pyridin-2-yl]-1H-pyrazolo[3,4-d]pyrimidin-6-yl}-(2-morpholin-4-yl-ethyl)-amine (Example 47);

{3-[6-(4-Chloro-benzylamino)-pyridin-2-yl]-1H-pyrazolo[3,4-d]pyrimidin-6-yl}-(2-morpholin-4-yl-ethyl)-amine (Example 48);

N-[3-(6-Benzylamino-pyridin-2-yl)-1H-pyrazolo[3,4-d]pyrimidin-6-yl]-cyclohexane-1,4-diamine (Example 49);

{3-[3-(4-Chloro-benzylamino)-phenyl]-1H-pyrazolo[3,4-d]pyrimidin-6-yl}-(2-morpholin-4-yl-ethyl)-amine (Example 50);

(2-Morpholin-4-yl-ethyl)-(3-{3-[(thiophen-3-ylmethyl)-amino]-phenyl}-1H-pyrazolo[3,4-d]pyrimidin-6-yl)-amine (Example 51);

N-[3-(3-Benzylamino-phenyl)-1H-pyrazolo[3,4-d]pyrimidin-6-yl]-cyclohexane-1,4-diamine (Example 52);

N-(3-{3-[(Thiophen-2-ylmethyl)-amino]-phenyl}-1H-pyrazolo[3,4-d]pyrimidin-6-yl)-cyclohexane-1,4-diamine (Example 53);

(2-Morpholin-4-yl-ethyl)-(3-{3-[(thiophen-2-ylmethyl)-amino]-phenyl}-1H-pyrazolo[3,4-d]pyrimidin-6-yl)-amine (Example 54);

N-{3-[3-(4-Chloro-benzylamino)-phenyl]-1H-pyrazolo[3,4-d]pyrimidin-6-yl}-cyclohexane-1,4-diamine (Example 55);
N-{3-[3-(2-Chloro-benzylamino)-phenyl]-1H-pyrazolo[3,4-d]pyrimidin-6-yl}-cyclohexane-1,4-diamine (Example 56);
{3-[3-(2-Chloro-benzylamino)-phenyl]-1H-pyrazolo[3,4-d]pyrimidin-6-yl}-(2-morpholin-4-yl-ethyl)-amine (Example 57);
N-(3-{3-[(Thiophen-3-ylmethyl)-amino]-phenyl}-1H-pyrazolo[3,4-d]pyrimidin-6-yl)-cyclohexane-1,4-diamine (Example 58);
{3-[6-(2-Chloro-benzylamino)-pyridin-2-yl]-1H-pyrazolo[3,4-d]pyrimidin-6-yl}-(2-morpholin-4-yl-ethyl)-amine (Example 59);
(2-Morpholin-4-yl-ethyl)-(3-{6-[(thiophen-3-ylmethyl)-amino]-pyridin-2-yl}-1H-pyrazolo[3,4-d]pyrimidin-6-yl)-amine (Example 60);
[3-(2-Benzylamino-pyrimidin-4-yl)-1H-pyrazolo[3,4-d]pyrimidin-6-yl]-(2-morpholin-4-yl-ethyl)-amine; hydrochloride (Example 61);
{3-[2-(3-Chloro-benzylamino)-pyrimidin-4-yl]-1H-pyrazolo[3,4-d]pyrimidin-6-yl}-(2-morpholin-4-yl-ethyl)-amine; hydrochloride (Example 62);
{3-[2-(2-Chloro-benzylamino)-pyrimidin-4-yl]-1H-pyrazolo[3,4-d]pyrimidin-6-yl}-(2-morpholin-4-yl-ethyl)-amine; hydrochloride (Example 63);
{3-[2-(4-Chloro-benzylamino)-pyrimidin-4-yl]-1H-pyrazolo[3,4-d]pyrimidin-6-yl}-(2-morpholin-4-yl-ethyl)-amine; hydrochloride (Example 64);
N-(3-{6-[(Thiophen-3-ylmethyl)-amino]-pyridin-2-yl}-1H-pyrazolo[3,4-d]pyrimidin-6-yl)-cyclohexane-1,4-diamine; hydrochloride (Example 65);
N-(3-{2-[(Thiophen-3-ylmethyl)-amino]-pyrimidin-4-yl}-1H-pyrazolo[3,4-d]pyrimidin-6-yl)-cyclohexane-1,4-diamine; hydrochloride (Example 66);
N-{3-[2-(2-Amino-1-phenyl-ethylamino)-pyrimidin-4-yl]-1H-pyrazolo[3,4-d]pyrimidin-6-yl}-cyclohexane-1,4-diamine; hydrochloride (Example 67);
N-{3-[2-(3-Amino-1-phenyl-propylamino)-pyrimidin-4-yl]-1H-pyrazolo[3,4-d]pyrimidin-6-yl}-cyclohexane-1,4-diamine; hydrochloride (Example 68);
N-{3-[6-(3-Amino-1-phenyl-propylamino)-pyridin-2-yl]-1H-pyrazolo[3,4-d]pyrimidin-6-yl}-cyclohexane-1,4-diamine; hydrochloride (Example 69);
N-[3-(2-Benzylamino-pyrimidin-4-yl)-1H-pyrazolo[3,4-d]pyrimidin-6-yl]-cyclohexane-1,4-diamine; hydrochloride (Example 70);
N-{3-[2-(3-Chloro-benzylamino)-pyrimidin-4-yl]-1H-pyrazolo[3,4-d]pyrimidin-6-yl}-cyclohexane-1,4-diamine; hydrochloride (Example 71);
N-{3-[2-(4-Chloro-benzylamino)-pyrimidin-4-yl]-1H-pyrazolo[3,4-d]pyrimidin-6-yl}-cyclohexane-1,4-diamine; hydrochloride (Example 72);
N1-{3-[6-(2-Morpholin-4-yl-ethylamino)-1H-pyrazolo[3,4-d]pyrimidin-3-yl]-phenyl}-1-phenyl-propane-1,3-diamine; hydrochloride (Example 73);
N-{3-[6-(2-Amino-1-phenyl-ethylamino)-pyridin-2-yl]-1H-pyrazolo[3,4-d]pyrimidin-6-yl}-cyclohexane-1,4-diamine; hydrochloride (Example 74);
N1-{6-[6-(2-Morpholin-4-yl-ethylamino)-1H-pyrazolo[3,4-d]pyrimidin-3-yl]-pyridin-2-yl}-1-phenyl-propane-1,3-diamine; hydrochloride (Example 75);
1-(3-Chloro-phenyl)-N1-{4-[6-(2-morpholin-4-yl-ethylamino)-1H-pyrazolo[3,4-d]pyrimidin-3-yl]-pyrimidin-2-yl}-ethane-1,2-diamine; hydrochloride (Example 76);
(2-Morpholin-4-yl-ethyl)-(3-{2-[(thiophen-3-ylmethyl)-amino]-pyrimidin-4-yl}-1H-pyrazolo[3,4-d]pyrimidin-6-yl)-amine; hydrochloride (Example 77);
N-(3-{2-[2-Amino-1-(3-chloro-phenyl)-ethylamino]-pyrimidin-4-yl}-1H-pyrazolo[3,4-d]pyrimidin-6-yl)-cyclohexane-1,4-diamine; hydrochloride (Example 78);
N-{3-[3-(3-Amino-1-phenyl-propylamino)-phenyl]-1H-pyrazolo[3,4-d]pyrimidin-6-yl}-cyclohexane-1,4-diamine; hydrochloride (Example 79);
N-(3-{2-[3-Amino-1-(3-chloro-phenyl)-propylamino]-pyrimidin-4-yl}-1H-pyrazolo[3,4-d]pyrimidin-6-yl)-cyclohexane-1,4-diamine; hydrochloride (Example 80);
N1-{4-[6-(2-Morpholin-4-yl-ethylamino)-1H-pyrazolo[3,4-d]pyrimidin-3-yl]-pyrimidin-2-yl}-1-phenyl-propane-1,3-diamine; hydrochloride (Example 81);
N1-{4-[6-(2-Morpholin-4-yl-ethylamino)-1H-pyrazolo[3,4-d]pyrimidin-3-yl]-pyrimidin-2-yl}-1-thiophen-3-yl-ethane-1,2-diamine; hydrochloride (Example 82);
N1-{4-[6-(2-Morpholin-4-yl-ethylamino)-1H-pyrazolo[3,4-d]pyrimidin-3-yl]-pyrimidin-2-yl}-1-phenyl-ethane-1,2-diamine; hydrochloride (Example 83);
N-{3-[2-(3-Trifluoromethyl-benzylamino)-pyrimidin-4-yl]-1H-pyrazolo[3,4-d]pyrimidin-6-yl}-cyclohexane-1,4-diamine; hydrochloride (Example 84);
N-{3-[2-(3-Fluoro-benzylamino)-pyrimidin-4-yl]-1H-pyrazolo[3,4-d]pyrimidin-6-yl}-cyclohexane-1,4-diamine; hydrochloride (Example 85);
{3-[2-(3-Chloro-benzylamino)-pyrimidin-4-yl]-1H-pyrazolo[3,4-d]pyrimidin-6-yl}-piperidin-4-yl-amine; hydrochloride (Example 86);
N-{3-[2-(3-Chloro-benzylamino)-pyrimidin-4-yl]-1H-pyrazolo[3,4-d]pyrimidin-6-yl}-N',N'-dimethyl-ethane-1,2-diamine; hydrochloride (Example 87);
{3-[2-(3-Chloro-benzylamino)-pyrimidin-4-yl]-1H-pyrazolo[3,4-d]pyrimidin-6-yl}-piperidin-4-ylmethyl-amine; hydrochloride (Example 88);
N-{3-[2-(3-Chloro-benzylamino)-pyrimidin-4-yl]-1H-pyrazolo[3,4-d]pyrimidin-6-yl}-cyclohexane-1,4-diamine; hydrochloride (Example 89);
{3-[2-(3-Chloro-benzylamino)-pyrimidin-4-yl]-1H-pyrazolo[3,4-d]pyrimidin-6-yl}-(2-pyrrolidin-1-yl-ethyl)-amine; hydrochloride (Example 90);
2-{3-[2-(3-Chloro-benzylamino)-pyrimidin-4-yl]-1H-pyrazolo[3,4-d]pyrimidin-6-ylamino}-ethanol; hydrochloride (Example 91);
{3-[2-(3-Chloro-benzylamino)-pyrimidin-4-yl]-1H-pyrazolo[3,4-d]pyrimidin-6-yl}-(2-piperazin-1-yl-ethyl)-amine; hydrochloride (Example 92);
{3-[2-(3-Chloro-benzylamino)-pyrimidin-4-yl]-1H-pyrazolo[3,4-d]pyrimidin-6-yl}-(2-piperazin-1-yl-ethyl)-amine; hydrochloride (Example 93);
and the pharmaceutically acceptable salts of the foregoing compounds.

The compounds of formula I, as well as their salts, that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

Dosages

The compounds of the present invention that are inhibitors of DYRK1B are useful in the treatment, amelioration or control of cell proliferative disorders, in particular chemoprevention of cancer. Chemoprevention is defined as inhibiting the development of invasive cancer by either blocking the initiating mutagenic event or by blocking the progression of premalignant cells that have already suffered an insult of inhibiting tumor relapse. These compounds and formulations containing said compounds are anticipated to be particularly useful in the treatment or control of solid tumors, such as, for example, lung, pancreas, colon, breast, bone and prostate tumors.

Compounds that are inhibitors of DYRK1A are useful in the treatment, amelioration or control of Down syndrome and Alzheimer's disease.

A "therapeutically effective amount" or "effective amount" of a compound in accordance with this invention means an amount of compound that is effective to alleviate, ameliorate or control symptoms of disease or prolong the survival of the subject being treated.

The therapeutically effective amount or dosage of a compound according to this invention can vary within wide limits. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration; it may be given as continuous infusion.

Compositions/Formulations

In an alternative embodiment, the present invention includes pharmaceutical compositions comprising at least one compound of formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

The pharmaceutical preparations of the invention can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

General Synthesis of the Compounds According to the Invention

The present invention also provides methods for the synthesis of the pyrazolo[3,4-d]pyrimidines of the invention.

The compounds of the invention can be prepared by processes known in the art. Suitable processes for synthesizing these compounds are also provided in the examples. Generally, compounds of formula I can be synthesized according to one of the below described synthetic routes.

The starting materials are either commercially available or can be synthesized by methods known to those of ordinary skill in the art. For compounds of formula Ic where both X and Y are N, in accordance to Scheme 1 below, 5-bromo-2,4-dichloro-pyrimidine (1) is reacted with 2-methylsulfanyl-pyrimidine-4-carbaldehyde (2) by a Grignard reaction and the resulting coupled alcohol is oxidized by manganese dioxide to give the corresponding ketone. This ketone is reacted with hydrazine to form 6-chloro-3-(2-methylsulfanyl-pyrimidin-4-yl)-1H-pyrazolo[3,4d]pyrimidine. The remaining chloro group can then be replaced by reacting with the appropriate amine and the sulfide group can be oxidized with peracid followed by displacement with the required amine to give compounds Ic of this invention.

In cases of certain amines that contained additional functional groups, appropriate protecting groups (for example tert-butoxy-carbonyl group) may be employed to facilitate synthesis. If such protecting groups are employed, the removal of such protecting groups to generate the compounds of the invention can be accomplished by standard methods known to those skilled in the art of organic synthesis.

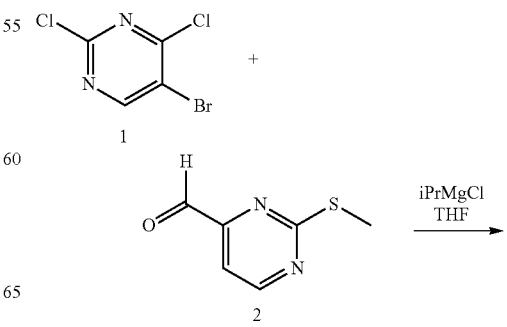

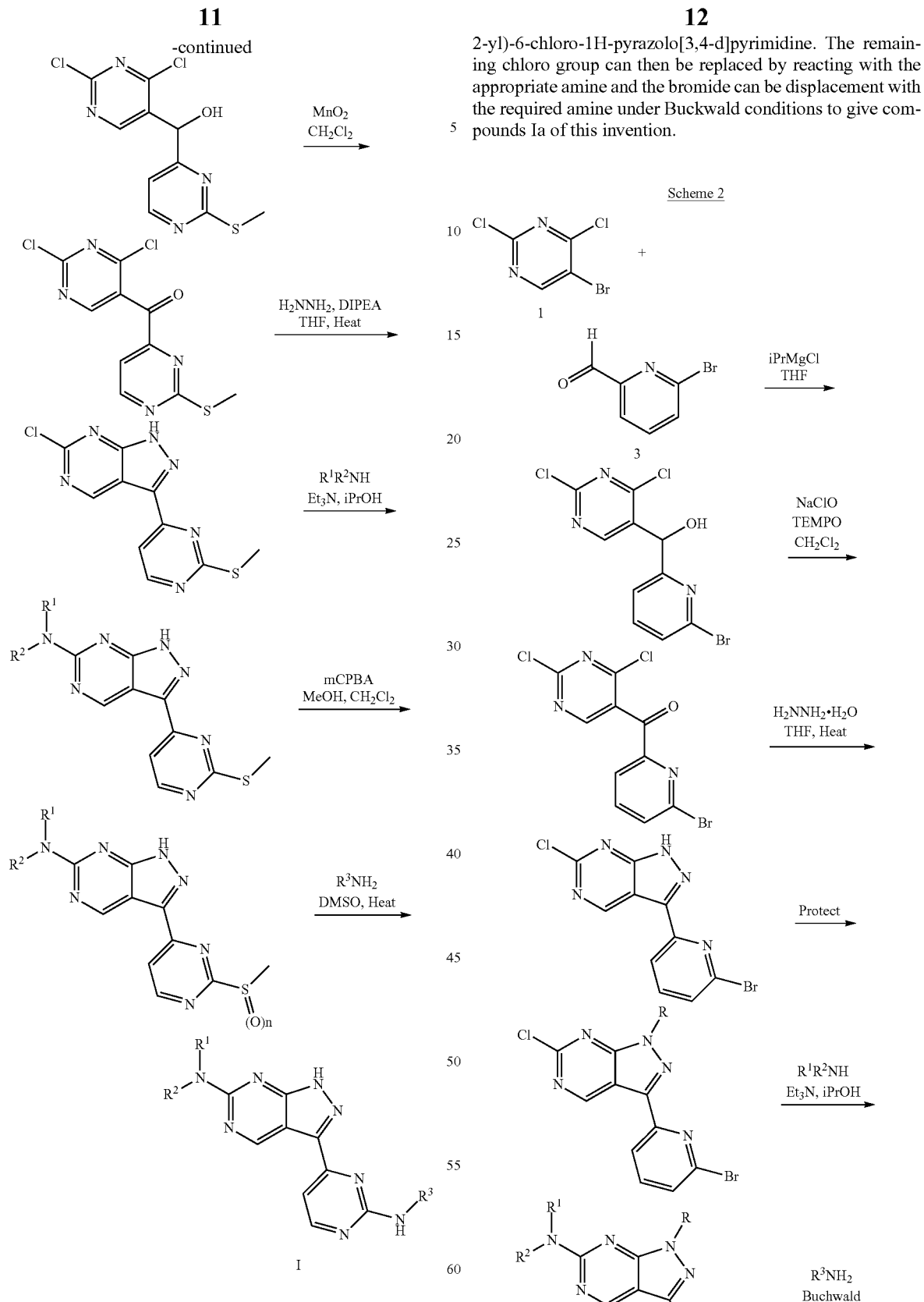

2-yl)-6-chloro-1H-pyrazolo[3,4-d]pyrimidine. The remaining chloro group can then be replaced by reacting with the appropriate amine and the bromide can be displacement with the required amine under Buckwald conditions to give compounds Ia of this invention.

Alternatively, for compounds of formula Ia where X is N and Y is CH, in accordance to Scheme 2 below, 5-bromo-2,4-dichloro-pyrimidine (1) is reacted with 6-bromo-pyridine-2-carbaldehyde (3) by a Grignard reaction and the corresponding coupled alcohol is oxidized to the ketone. The ketone is reacted with hydrazine to give 3-(6-bromo-pyridin-

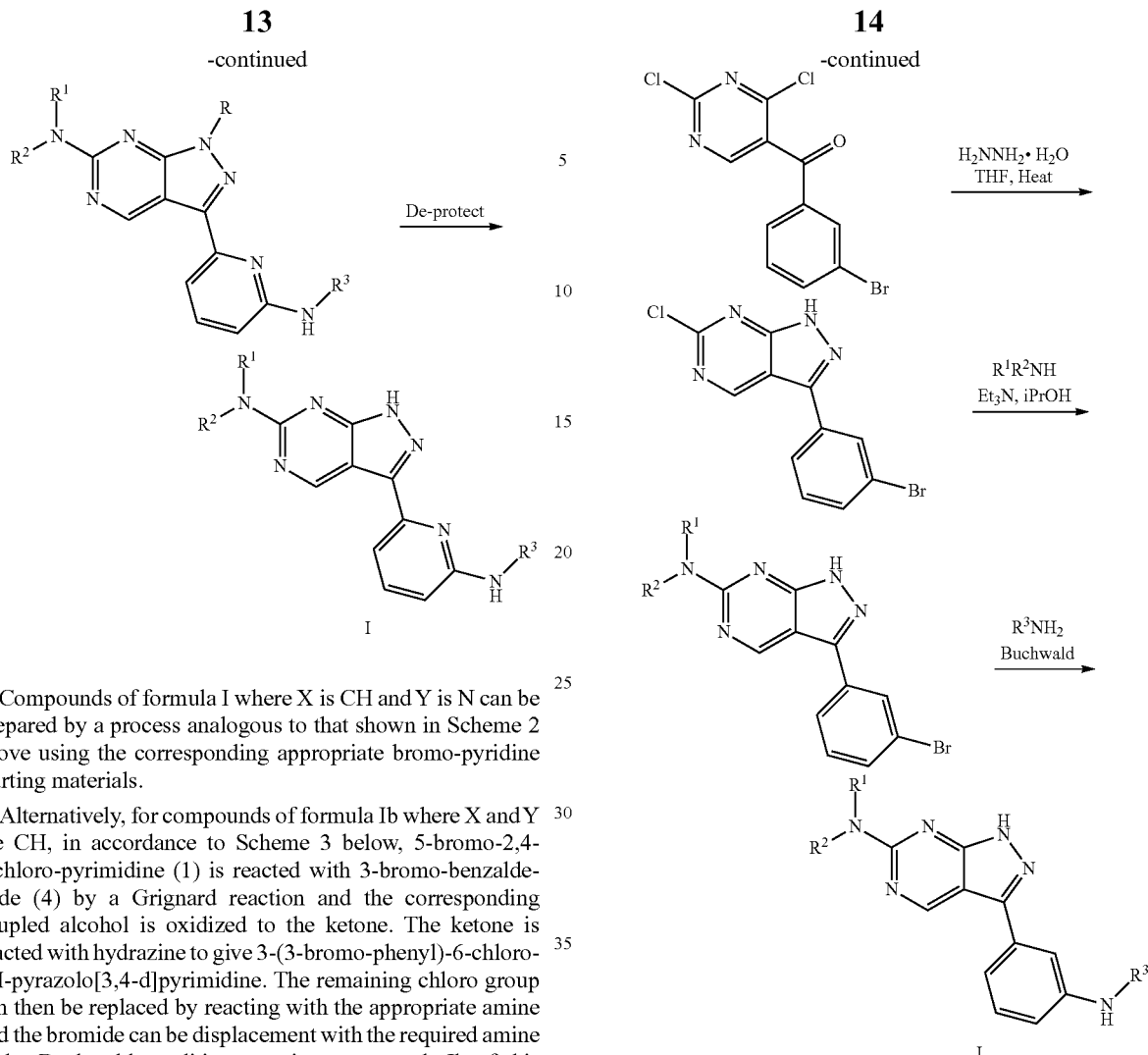

Compounds of formula I where X is CH and Y is N can be prepared by a process analogous to that shown in Scheme 2 above using the corresponding appropriate bromo-pyridine starting materials.

Alternatively, for compounds of formula Ib where X and Y are CH, in accordance to Scheme 3 below, 5-bromo-2,4-dichloro-pyrimidine (1) is reacted with 3-bromo-benzaldehyde (4) by a Grignard reaction and the corresponding coupled alcohol is oxidized to the ketone. The ketone is reacted with hydrazine to give 3-(3-bromo-phenyl)-6-chloro-1H-pyrazolo[3,4-d]pyrimidine. The remaining chloro group can then be replaced by reacting with the appropriate amine and the bromide can be displacement with the required amine under Buckwald conditions to give compounds Ib of this invention.

Scheme 3

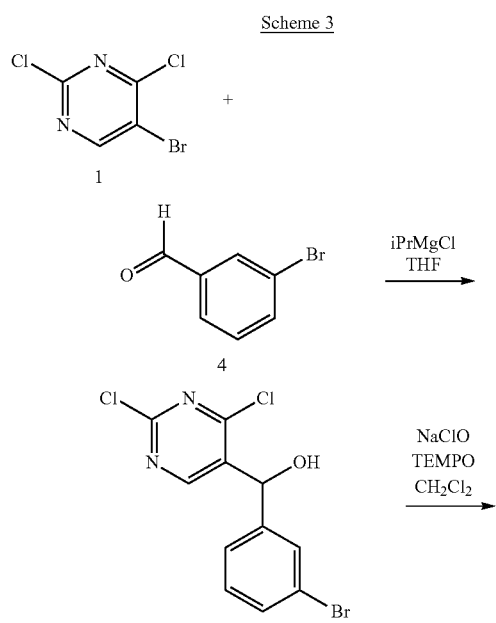

Crystal Forms

When the compounds of the invention are solids, it is understood by those skilled in the art that these compounds, and their salts, may exist in different crystal or polymorphic forms, all of which are intended to be within the scope of the present invention and specified formulas.

EXAMPLES

The compounds of the present invention may be synthesized according to known techniques. The following examples and references are provided to aid the understanding of the present invention. The examples are not intended, however, to limit the invention, the true scope of which is set forth in the appended claims. The names of the final products in the examples were generated using AutoNom 2000 Add-in v4.0 SP2, (function in ISIS Draw, Elsevier/MDL), or AutoNom 2000 TT v4.01.305 (Elsevier/MDL), or functions available in ChemDraw Pro Control 11.0.2 (CambridgeSoft Corp.).

Abbreviations Used in the Examples:
Ac$_2$O acetic anhydride
Boc$_2$O di-tert-butyl dicarbonate
Bu$_4$NI tetrabutyl ammonium iodide BuOH butanol
tBuONa sodium t-butoxide
CDCl$_3$ chloroform-d
CD$_3$OD methanol-d$_4$
CF$_3$CO$_2$H trifluoroacetic acid
CH$_2$Cl$_2$ dichloromethane
CH$_3$CN acetonitrile
CH$_2$(CO$_2$CH$_3$)$_2$ dimethyl malonate
C$_2$H$_5$OH ethanol
m-CPBA meta-chloroperbenzoic acid
Dave-PHOS 2-(2-dicyclohexylphosphanylphenyl)-N,N-dimethylaniline
DCM dichloromethane
DEAD diethyl azodicarboxylate
DIPEA N,N-diisopropylethylamine
DMF N,N-dimethylformamide
DMSO dimethylsulfoxide
D$_2$O deuterium oxide
Et$_3$N triethylamine
EtOAc ethyl acetate
(EtO)$_3$CH triethyl orthoformate
EtOH ethanol
HATU O-(7-azabenzotriazol-1-yl)-N,N,N',N'-tetramethyluronium hexafluorophosphate
HBTU O-(benzotriazol-1-yl)-N,N,N',N'-tetramethyluronium hexafluorophosphate
HCl hydrogen chloride
HCO$_2$NH$_4$ ammonium formate
H$_2$O water
HOAc acetic acid
HPLC high performance liquid chromatography
H$_2$SO$_4$ sulfuric acid
IPA 2-propanol
LAH lithium aluminum hydride
LC-MS or HPLC-MS liquid chromatography-mass spectroscopy
LiAlH$_4$ lithium aluminum hydride
LiOH lithium hydroxide
KCN potassium cyanide
K$_2$CO$_3$ potassium carbonate
K$_3$PO$_4$ potassium phosphate
MeCN acetonitrile
MeOH methanol
MgSO$_4$ magnesium sulfate
MnO$_2$ manganese dioxide
NaClO sodium hypochlorite
NaH sodium hydride
NaHCO$_3$ sodium bicarbonate
NaOH sodium hydroxide
Na$_2$SO$_4$ sodium sulfate
NH$_3$ ammonia
NH$_4$Cl ammonium chloride
Pd$_2$(dba)$_3$ tris(dibenzylideneacetone)dipalladium(0)
Pd(OAc)$_2$ palladium(II) acetate
POCl$_3$ phosphorous oxychloride
i-PrMgCl isopropyl magnesium chloride
PPh$_3$ triphenylphosphine
SEM-Cl 2-(trimethylsilyl)ethoxymethyl chloride
TBAB tetrabutyl ammonium bromide
TEA triethylamine
TEMPO 2,2,6,6-tetramethylpiperidine 1-oxyl
TFA trifluoroacetic acid
THF tetrahydrofuran
TLC thin layer chromatography The following starting materials were purchased from the sources listed below.

2-Amino-1-phenylethanol Alfa Aesar China (Tianjin) Co., Ltd.
Isopropylmagnesium chloride Sigma-Aldrich (Shanghai) Trading Co., Ltd
6-Bromopicolinaldehyde Alfa Aesar China (Tianjin) Co., Ltd.
X-Phos Alfa Aesar China (Tianjin) Co., Ltd.
Dave-phos Alfa Aesar China (Tianjin) Co., Ltd.
Hydrazine hydrate Alfa Aesar China (Tianjin) Co., Ltd.
Sodium t-butoxide Alfa Aesar China (Tianjin) Co., Ltd.
tris(Dibenzylideneacetone)dipalladium Alfa Aesar China (Tianjin) Co., Ltd.
2-Morpholinoethanamine Sigma-Aldrich (Shanghai) Trading Co., Ltd
2-Thiophenemethylamine Alfa Aesar China (Tianjin) Co., Ltd.
Benzoylacetonitrile Alfa Aesar China (Tianjin) Co., Ltd.
Trityl chloride Alfa Aesar China (Tianjin) Co., Ltd.
3-(Trifluoromethyl)benzylamine Beijing Huagong
3-Fluorobenzylamine Beijing Huagong
Phthalimide Beijing Huagong
Potassium cyanide Beijing Huagong
2-Chlorobenzylamine Alfa Aesar China (Tianjin) Co., Ltd.
3-Chlorobenzylamine Alfa Aesar China (Tianjin) Co., Ltd.
4-Chlorobenzylamine Alfa Aesar China (Tianjin) Co., Ltd.
5-Bromo-2,4-dichloropyrimidine Beijing Huagong
4-Amino-1-boc-piperidine Alfa Aesar China (Tianjin) Co., Ltd.
1-Boc-piperazine Alfa Aesar China (Tianjin) Co., Ltd.
1-N-Boc-cis-1,4-cyclohexyldiamine Alfa Aesar China (Tianjin) Co., Ltd.
Palladium diacetate Shanghai Aopudishi Huaxue
Tetrakis(triphenylphosphine)platinum(0) Shanghai Aopudishi Huaxue
[1,1'-bis(Diphenylphosphino)ferrocene]dichloropalladium(II) Shanghai Aopudishi Huaxue Example 1

(2-Amino-2-phenyl-ethyl)-carbamic acid tert-butyl ester

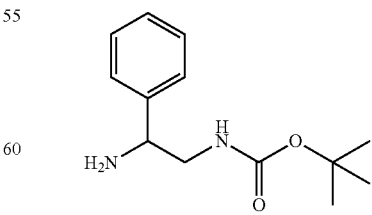

(2-Amino-2-phenyl-ethyl)-carbamic acid tert-butyl ester was prepared according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A (2-Hydroxy-2-phenyl-ethyl)-carbamic acid tert-butyl ester

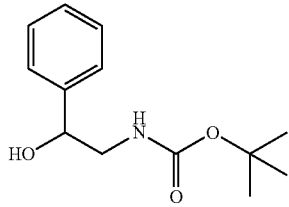 [SMILES: CC(C)(C)OC(=O)NCC(O)c1ccccc1]

To a stirred solution of 2-amino-1-phenylethanol (20 g, 145.8 mmol) in THF (300 mL) was added the solution of Boc$_2$O (31.1 g, 153.1 mmol) in THF (100 mL) at 0° C. After addition, the mixture was stirred at room temperature for 0.5 hour. This mixture was concentrated to give the pure (2-hydroxy-2-phenyl-ethyl)-carbamic acid tert-butyl ester as a white solid. (Yield 34.4 g, 100%).

Step B

[2-(1,3-Dioxo-1,3-dihydro-isoindol-2-yl)-2-phenyl-ethyl]-carbamic acid tert-butyl ester

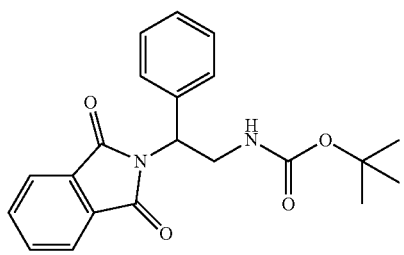 [SMILES: CC(C)(C)OC(=O)NCC(c1ccccc1)N1C(=O)c2ccccc2C1=O]

To a solution of (2-hydroxy-2-phenyl-ethyl)-carbamic acid tert-butyl ester (34.4 g, 145.0 mmol), phthalimide (21.3 g, 145 mmol), and PPh$_3$ (49.4 g, 188.5 mmol) was added drop-wise DEAD (32.8 g, 188.5 mmol) under stirring at 0° C. After addition, the mixture was stirred at room temperature for an additional 1 hour. The mixture was concentrated under reduced pressure. The residue was purified by column chromatography on silica gel (petroleum ether:ethyl acetate, 20:1 to 5:1) to give [2-(1,3-dioxo-1,3-dihydro-isoindol-2-yl)-2-phenyl-ethyl]-carbamic acid tert-butyl ester as a white solid. (Yield 39 g, 74%).

$^1$H NMR (300 MHz, CDCl$_3$): δ 7.88-7.80 (m, 2H), 7.74-7.68 (m, 2H), 7.49-7.47 (m, 2H), 7.38-7.26 (m, 3H), 5.56-5.50 (m, 1H), 4.83 (brs, 1H), 4.28-4.22 (m, 1H), 3.93-3.87 (m, 1H), 1.35 (s, 9H). LC-MS: [M-Boc+H]$^+$ 267.

Step C (2-Amino-2-phenyl-ethyl)-carbamic acid tert-butyl ester

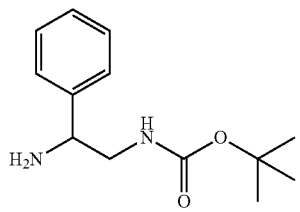 [SMILES: CC(C)(C)OC(=O)NCC(N)c1ccccc1]

To a solution of [2-(1,3-dioxo-1,3-dihydro-isoindol-2-yl)-2-phenyl-ethyl]-carbamic acid tert-butyl ester (23 g, 63 mmol) in THF (180 mL) and MeOH (180 mL) was added 85% hydrazine hydrate (37 mL, 630 mmol) slowly. The resulting mixture was heated at 65° C. for 15 hours. The reaction mixture was cooled to room temperature, then concentrated to dryness. The residue was purified by column chromatography on silica gel (dichloromethane:MeOH, 100:1, 1% NH$_3$H$_2$O) to give (2-amino-2-phenyl-ethyl)-carbamic acid tert-butyl ester as a white solid. (Yield 7.4 g, 50%).

$^1$H NMR (300 MHz, CDCl$_3$): δ 7.35-7.24 (m, 5H), 4.81 (brs, 1H), 4.08-4.03 (m, 1H), 3.38-3.21 (m, 2H), 1.44 (s, 9H). LC-MS: [M+H]$^+$ 237.

Example 2

(3-Amino-3-phenyl-propyl)-carbamic acid tert-butyl ester

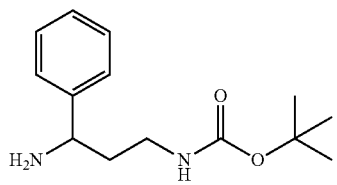 [SMILES: CC(C)(C)OC(=O)NCCC(N)c1ccccc1]

(3-Amino-3-phenyl-propyl)-carbamic acid tert-butyl ester was prepared according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A

3-Amino-1-phenyl-propan-1-ol

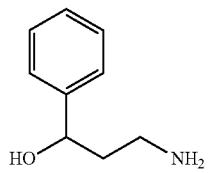

To a stirred suspension of LAH (20 g, 517 mmol) in dry THF (500 mL) was added a solution of 3-oxo-3-phenylpropanenitrile (30 g, 207 mmol) in dry THF (300 mL) drop-wise at 0° C. under nitrogen atmosphere.

The mixture was warmed to 25° C. and then heated at 70° C. for 2 hours. After cooling to 0° C., a saturated solution of sodium hydroxide was added drop-wise and extracted with dichloromethane (200 mL). The organic solution was dried over anhydrous sodium sulfate and concentrated to dryness. The residue was purified by column chromatography (methanol:dichloromethane, 1:10) to afford 3-amino-1-phenyl-propan-1-ol. (Yield 30 g, crude).

LC-MS: [M+H]$^+$ 152.

Step B (3-Hydroxy-3-phenyl-propyl)-carbamic acid tert-butyl ester

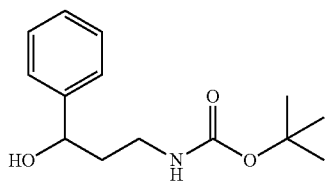 [SMILES: CC(C)(C)OC(=O)NCCC(O)c1ccccc1]

Et$_3$N (1.36 g, 14 mmol) was added to a solution of 3-amino-1-phenyl-propan-1-ol (1.7 g, 11.3 mmol) in THF (20 mL) under stirring. Boc$_2$O (3.0 g, 13.7 mmol) in THF (20 mL) was added dropwise to the solution at 0° C. Then the resulting mixture was warmed to room temperature and stirred for an additional 2 hours. The mixture was concentrated under reduced pressure. The residue was purified by column chromatography on silica gel (petroleum ether:ethyl acetate, 3:1) to give (3-hydroxy-3-phenyl-propyl)-carbamic acid tert-butyl ester. (Yield 1.7 g, 60%).

LC-MS: [M+23]$^+$ 274.

Step C

[3-(1,3-Dioxo-1,3-dihydro-isoindol-2-yl)-3-phenyl-propyl]-carbamic acid tert-butyl ester

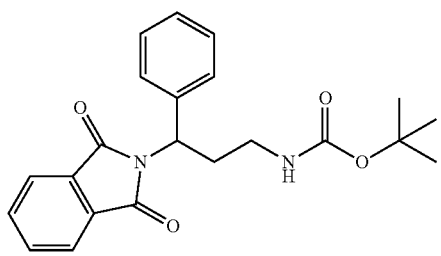 [SMILES: CC(C)(C)OC(=O)NCCC(c1ccccc1)N1C(=O)c2ccccc2C1=O]

To a solution of (3-hydroxy-3-phenyl-propyl)-carbamic acid tert-butyl ester (10.4 g, 41.4 mmol), phthalimide (5.2 g, 36.6 mmol), and PPh$_3$ (14.6 g, 55.5 mmol) in THF (204 mL) was added dropwise DEAD (8.9 mL, 55 mmol) with stirring at 0° C. Then the resulting mixture was warmed to room temperature for an additional 2 hours. The mixture was concentrated under reduced pressure. The residue was purified by column chromatography on silica gel (petroleum ether:ethyl acetate, 3:1) to give [3-(1,3-dioxo-1,3-dihydro-isoindol-2-yl)-3-phenyl-propyl]-carbamic acid tert-butyl ester. (Yield 10.5 g, 66.8%).

$^1$H NMR (300 MHz, CDCl$_3$): δ 7.81-7.75 (m, 2H), 7.69-7.64 (m, 2H), 7.53-7.50 (m, 2H), 7.34-7.23 (m, 3H), 5.44-5.38 (m, 1H), 4.74 (brs, 1H), 3.29-3.07 (m, 2H), 2.83-2.75 (m, 1H), 2.51-2.42 (m, 1H), 1.42 (s, 9H). LC-MS: [M-Boc+H]$^+$ 281.

Step D (3-Amino-3-phenyl-propyl)-carbamic acid tert-butyl ester

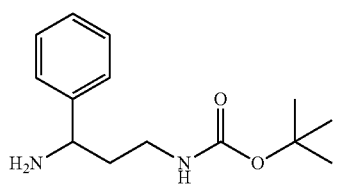 [SMILES: CC(C)(C)OC(=O)NCCC(N)c1ccccc1]

85% Hydrazine hydrate (5.1 mL, 74 mmol) was added to a solution of [3-(1,3-dioxo-1,3-dihydro-isoindol-2-yl)-3-phenyl-propyl]-carbamic acid tert-butyl ester (2.8 g, 7.4 mmol) in THF (25 mL) and MeOH (25 mL). The resulting mixture was heated at 65° C. for 6 hours. Then the precipitate was filtered, and the filtrate was concentrated under reduced pressure to give crude product which was purified by column chromatography on silica gel (dichloromethane:MeOH, 100:1, 1% NH$_3$H$_2$O) to give (3-amino-3-phenyl-propyl)-carbamic acid tert-butyl ester as an off-white solid. (Yield 1.7 g, 92%).

$^1$H NMR (300 MHz, CDCl$_3$): δ 7.31-7.18 (m, 5H), 6.82 (brs, 1H), 3.78-3.74 (m, 1H), 2.92 (brs, 2H), 1.82 (s, 2H), 1.63-1.61 (m, 2H), 1.37 (s, 9H). LC-MS: [M+H]$^+$ 251.

Example 3

[3-Amino-3-(3-chloro-phenyl)-propyl]-carbamic acid tert-butyl ester

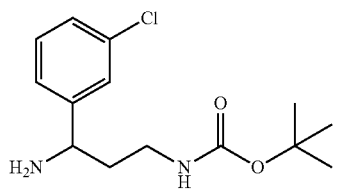 [SMILES: CC(C)(C)OC(=O)NCCC(N)c1cccc(Cl)c1]

[3-Amino-3-(3-chloro-phenyl)-propyl]-carbamic acid tert-butyl ester was prepared in an analogous process according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A

3-Amino-1-(3-chloro-phenyl)-propan-1-ol

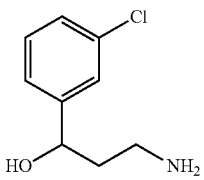 [SMILES: NCCC(O)c1cccc(Cl)c1]

To a stirred suspension of LAH (16 g, 90 mmol) in dry THF (200 mL) was added a solution of 3-(3-chlorophenyl)-3-oxo-propanenitrile (10.4 g, 270 mmol) in dry THF (200 mL) dropwise at 0° C. under nitrogen atmosphere. The mixture was warmed to 25° C. and then heated at 60° C. for 3 hours. After cooling to 0° C., a saturated solution of sodium hydroxide was added dropwise and extracted with ethyl acetate (200 mL). The solution was dried over anhydrous sodium sulfate and concentrated to dryness. The crude 3-amino-1-(3-chloro-phenyl)-propan-1-ol obtained was used in the next step without further purification. (Yield 14.5 g, crude).
LC-MS: [M+H]$^+$ 186.

Step B

[3-(3-Chloro-phenyl)-3-hydroxy-propyl]-carbamic acid tert-butyl ester

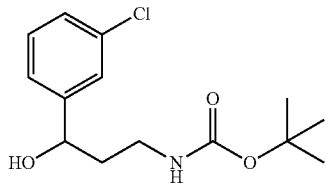 [SMILES: CC(C)(C)OC(=O)NCCC(O)c1cccc(Cl)c1]

To a stirred solution of crude 3-amino-1-(3-chloro-phenyl)-propan-1-ol (29 g, 156 mmol) in THF (300 mL) was added Boc$_2$O (40.5 g, 187 mmol). After 0.5 hour, the mixture was concentrated to dryness. The residue was purified by column chromatography (ethyl acetate:petroleum ether, 1:20) to afford [3-(3-chloro-phenyl)-3-hydroxy-propyl]-carbamic acid tert-butyl ester. (Yield 23 g, 52%). LC-MS: [M+Na]$^+$ 308.

Step C

[3-(3-Chloro-phenyl)-3-(1,3-dioxo-1,3-dihydro-isoindol-2-yl)-propyl]-carbamic acid tert-butyl ester

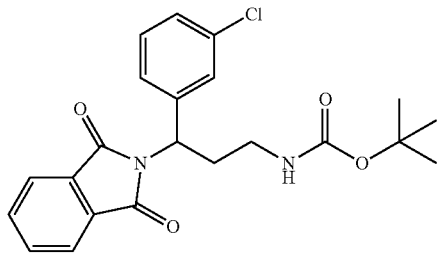 [SMILES: CC(C)(C)OC(=O)NCCC(c1cccc(Cl)c1)N1C(=O)c2ccccc2C1=O]

To a stirred solution of [3-(3-chloro-phenyl)-3-hydroxy-propyl]-carbamic acid tert-butyl ester (12 g, 42 mmol), phthalimide (6.2 g, 42 mmol), and PPh$_3$ (14.3 g, 55 mmol) in THF (150 mL) was added DEAD (9.0 mL, 55 mmol) dropwise at about 5° C. After 1 hour, the mixture was concentrated to dryness. The residue was purified by column chromatography (ethyl acetate:petroleum ether, 1:8) to afford [3-(3-chloro-phenyl)-3-(1,3-dioxo-1,3-dihydro-isoindol-2-yl)-propyl]-carbamic acid tert-butyl ester. (Yield 15.65 g, 90%).
LC-MS: [M+H]$^+$ 415.

Step D

[3-Amino-3-(3-chloro-phenyl)-propyl]-carbamic acid tert-butyl ester

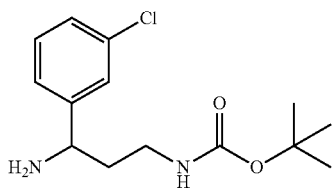 [SMILES: CC(C)(C)OC(=O)NCCC(N)c1cccc(Cl)c1]

To a stirred solution of [3-(3-chloro-phenyl)-3-(1,3-dioxo-1,3-dihydro-isoindol-2-yl)-propyl]-carbamic acid tert-butyl ester (0.15 g, 0.36 mmol) in THF (2 mL) and methanol (2 mL) was added hydrazine hydrate (0.18 g, 3.6 mmol). The mixture was heated at 55° C. for 2 hours. Then the reaction mixture was concentrated and extracted with ethyl acetate (10 mL). The organic mixture was washed with water (3×1 mL), brine (1 mL), dried over anhydrous sodium sulfate and concentrated to dryness. The residue was purified by column chromatography (methanol:dichloromethane, 1:100) to afford [3-amino-3-(3-chloro-phenyl)-propyl]-carbamic acid tert-butyl ester. (Yield 0.061 g, 60%). LC-MS: [M+H]$^+$ 285.

Example 4

[2-Amino-2-(3-chloro-phenyl)-ethyl]-carbamic acid tert-butyl ester

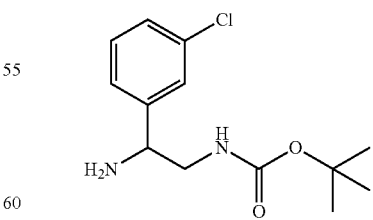

[2-Amino-2-(3-chloro-phenyl)-ethyl]-carbamic acid tert-butyl ester was prepared in an analogous process according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A (3-Chloro-phenyl)-hydroxy-acetonitrile

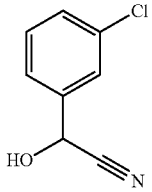 [SMILES: N#CC(O)c1cccc(Cl)c1]

To a stirred suspension of potassium cyanide (5.04 g, 78 mmol) in methanol (20 mL) was added 3-chlorobenzaldehyde (7.0 g, 50 mmol) at 0° C. under nitrogen atmosphere. Then acetic acid (4.4 mL) was added dropwise at 0° C. After 30 minutes, the mixture was warmed to 15° C. and stirred for 5 hours. Then the reaction mixture was concentrated to dryness and extracted with ethyl acetate (200 mL). The organic solution was washed with water (3×25 mL), brine (25 mL), dried over anhydrous sodium sulfate and concentrated to dryness. The resulting residue was purified by column chromatography (ethyl acetate:petroleum ether, 1:15) to afford (3-chloro-phenyl)-hydroxy-acetonitrile. (Yield 8.2 g, 97%).

LC-MS: [M+Na]$^+$ 190.

Step B

2-Amino-1-(3-chloro-phenyl)-ethanol

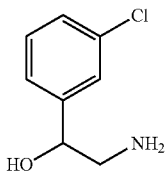

To a stirred suspension of LAH (2.36 g, 59 mmol) in dry THF (70 mL) was added a solution of (3-chloro-phenyl)-hydroxy-acetonitrile (4.0 g, 24 mmol) in dry THF (55 mL) dropwise at 0° C. under nitrogen atmosphere. The mixture was warmed to 25° C. and then heated at 60° C. for 2 hours. After cooling to 0° C., a saturated solution of sodium hydroxide was added dropwise and extracted with dichloromethane (200 mL). The organic solution was dried over anhydrous sodium sulfate and concentrated to dryness. The residue was purified by column chromatography (methanol:dichloromethane, 1:10) to afford 2-amino-1-(3-chloro-phenyl)-ethanol. (Yield 2.86 g, 70%).

LC-MS: [M+H]$^+$ 172.

Step C

[2-(3-Chloro-phenyl)-2-hydroxy-ethyl]-carbamic acid tert-butyl ester

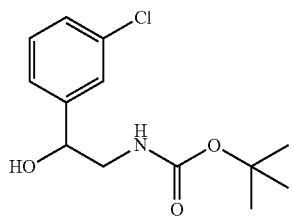 [SMILES: CC(C)(C)OC(=O)NCC(O)c1cccc(Cl)c1]

To a stirred solution of 2-amino-1-(3-chloro-phenyl)-ethanol (2.86 g, 16.7 mmol) in THF (100 mL) was added Boc$_2$O (4.3 g, 20 mmol). After 1 hour, the mixture was concentrated to dryness. The residue was purified by column chromatography (methanol:dichloromethane, 1:100) to afford [2-(3-chloro-phenyl)-2-hydroxy-ethyl]-carbamic acid tert-butyl ester. (Yield 3.9 g, 72%).

LC-MS: [M+Na]$^+$ 294.

Step D

[2-(3-Chloro-phenyl)-2-(1,3-dioxo-1,3-dihydro-isoindol-2-yl)-ethyl]-carbamic acid tert-butyl ester

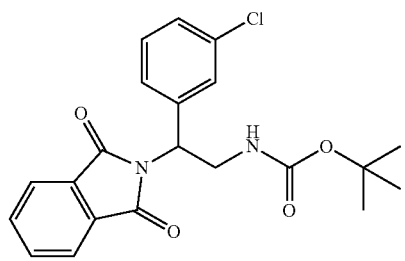 [SMILES: CC(C)(C)OC(=O)NCC(c1cccc(Cl)c1)N1C(=O)c2ccccc2C1=O]

To a stirred solution of [2-(3-chloro-phenyl)-2-hydroxy-ethyl]-carbamic acid tert-butyl ester (20 g, 73.5 mmol), phthalimide (11.1 g, 73.5 mmol) and PPh$_3$ (25.1 g, 95.5 mmol) in THF (500 mL) was added DEAD (11.4 mL, 95.5 mmol) dropwise at −5 to 0° C. The reaction mixture was stirred at room temperature for 3 hours. Then the mixture was concentrated to dryness. The residue was purified by column chromatography (ethyl acetate:petroleum ether, 1:10) to afford [2-(3-chloro-phenyl)-2-(1,3-dioxo-1,3-dihydro-isoindol-2-yl)-ethyl]-carbamic acid tert-butyl ester. (Yield 20 g, 69%).

LC-MS: [M+H]$^+$ 401.

Step E

[2-Amino-2-(3-chloro-phenyl)-ethyl]-carbamic acid tert-butyl ester

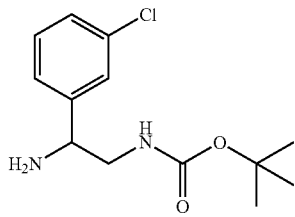 [SMILES: CC(C)(C)OC(=O)NCC(N)c1cccc(Cl)c1]

To a stirred solution of [2-(3-chloro-phenyl)-2-(1,3-dioxo-1,3-dihydro-isoindol-2-yl)-ethyl]-carbamic acid tert-butyl ester (2.5 g, 6.2 mmol) in THF (10 mL) and methanol (10 mL) was added hydrazine hydrate (3.1 g, 62 mmol). The mixture was heated at 55° C. for 1 hour. Then it was concentrated to dryness, dissolved in H$_2$O (5 mL) and extracted with ethyl acetate (50 mL). The organic mixture was concentrated and purified by column chromatography (methanol:dichloromethane, 1:100) to afford [2-amino-2-(3-chloro-phenyl)-ethyl]-carbamic acid tert-butyl ester. (Yield 1.325 g, 79%). LC-MS: [M+H]$^+$ 271.

Example 5

(3-Amino-3-thiophen-3-yl-propyl)-carbamic acid tert-butyl ester

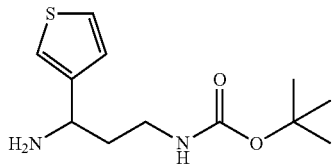 [SMILES: CC(C)(C)OC(=O)NCCC(N)c1ccsc1]

(3-Amino-3-thiophen-3-yl-propyl)-carbamic acid tert-butyl ester was prepared in an analogous process according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A

3-Amino-1-thiophen-3-yl-propan-1-ol

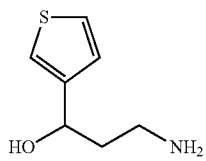

To a stirred suspension of LAH (1.45 g, 38.1 mmol) in dry THF (120 mL) was added a solution of 3-oxo-3-(thiophen-3-yl)propanenitrile (4.8 g, 31.8 mmol) in dry THF (40 mL) dropwise at 0° C. under nitrogen atmosphere. The mixture was warmed to 25° C. and then heated at 65° C. for 6 hours. After cooling to 0° C., a saturated solution of sodium hydroxide (2 mL) was added dropwise and the mixture was filtered. The filtrate was concentrated to dryness to give crude 3-amino-1-thiophen-3-yl-propan-1-ol which was used in next step without further purification.

$^1$H NMR (300 MHz, CDCl$_3$): δ 7.29-7.26 (m, 2H), 7.05 (dd, 1H, J$_1$=4.8 Hz, J$_2$=1.2 Hz), 5.04 (dd, 1H, J$_1$=8.1 Hz, J$_2$=3.0 Hz), 3.10-3.05 (m, 2H), 1.82-1.77 (m, 2H).

Step B (3-Hydroxy-3-thiophen-3-yl-propyl)-carbamic acid tert-butyl ester

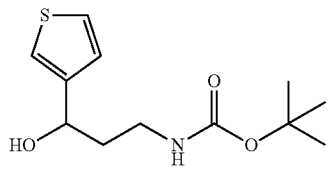 [SMILES: CC(C)(C)OC(=O)NCCC(O)c1ccsc1]

To a stirred solution of crude 3-amino-1-thiophen-3-yl-propan-1-ol (23 g) in THF (100 mL) was added Boc$_2$O (31.6 g, 146.3 mmol). The mixture was stirred at room temperature for 1 hour and then concentrated to dryness. The residue was purified by column chromatography (ethyl acetate:petroleum ether, 1:10) to afford (3-hydroxy-3-thiophen-3-yl-propyl)-carbamic acid tert-butyl ester. (Yield 21.5 g, 51% for two steps).

$^1$H NMR (300 MHz, CDCl$_3$): δ 8.08-8.06 (m, 1H), 7.55-7.53 (m, 1H), 7.34-7.30 (m, 1H), 5.10 (s, 1H), 3.52-3.48 (m, 2H), 3.13-3.09 (m, 2H), 1.42 (s, 9H). LC-MS: [M+Na]$^+$ 280.

Step C 3-(1,3-Dioxo-1,3-dihydro-isoindol-2-yl)-3-thiophen-3-yl-propyl]-carbamic acid tert-butyl ester

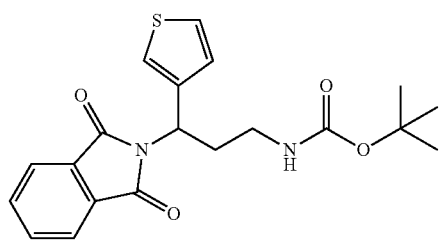 [SMILES: CC(C)(C)OC(=O)NCCC(c1ccsc1)N1C(=O)c2ccccc2C1=O]

To a stirred solution of (3-hydroxy-3-thiophen-3-yl-propyl)-carbamic acid tert-butyl ester (21.5 g, 83.6 mmol), phthalimide (12.3 g, 83.6 mmol), and PPh$_3$ (28.5 g, 108.6 mmol) in THF (400 mL) was added DEAD (17.6 mL, 108.6 mmol) dropwise at 25° C. The mixture was stirred at room temperature for 14 hours, then concentrated. The residue was purified by column chromatography (ethyl acetate:petroleum ether, 1:6) to afford 3-(1,3-dioxo-1,3-dihydro-isoindol-2-yl)-3-thiophen-3-yl-propyl]-carbamic acid tert-butyl ester. (Yield 12 g, 38%).

$^1$H NMR (300 MHz, CDCl$_3$): δ 7.82-7.77 (m, 2H), 7.72-7.68 (m, 2H), 7.36 (d, 1H, J=1.8 Hz), 7.26-7.18 (m, 2H), 5.50 (dd, 1H, J$_1$=9.6 Hz, J$_2$=6 Hz), 4.65 (brs, 1H), 3.24-3.07 (m, 2H), 2.72-2.67 (m, 1H), 2.47-2.40 (m, 1H), 1.40 (s, 9H). LC-MS: [M+H-Boc]$^+$ 287.

Step D (3-Amino-3-thiophen-3-yl-propyl)-carbamic acid tert-butyl ester

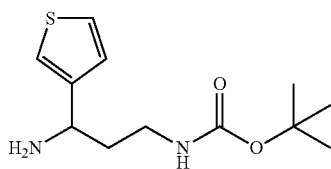 [SMILES: CC(C)(C)OC(=O)NCCC(N)c1ccsc1]

To a stirred solution of 3-(1,3-dioxo-1,3-dihydro-isoindol-2-yl)-3-thiophen-3-yl-propyl]-carbamic acid tert-butyl ester (12 g, 31.1 mmol) in methanol (150 mL) was added hydrazine hydrate (18 mL, 85% aqueous). The mixture was heated at reflux for 14 hours. After cooling to room temperature, the reaction mixture was filtered. The filtrate was concentrated and the residue was purified by column chromatography (methanol:dichloromethane, 1:50 to 1:20, 0.1% $NH_3H_2O$) to afford (3-amino-3-thiophen-3-yl-propyl)-carbamic acid tert-butyl ester. (Yield 7.6 g, 95%).

$^1$H NMR (300 MHz, $CDCl_3$): δ 7.49 (s, 1H), 7.25-7.08 (m, 2H), 6.82 (brs, 1H), 3.85 (t, 1H, J=6.0 Hz), 3.18-2.95 (m, 4H), 1.75-1.62 (m, 2H), 1.37 (s, 9H). LC-MS: $[M+H]^+$ 257.

Example 6

(2-Amino-2-thiophen-3-yl-ethyl)-carbamic acid tert-butyl ester

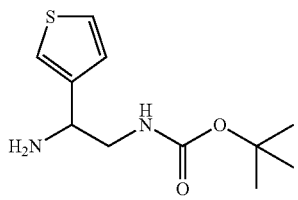 [SMILES: CC(C)(C)OC(=O)NCC(N)c1ccsc1]

(2-Amino-2-thiophen-3-yl-ethyl)-carbamic acid tert-butyl ester was prepared in an analogous process according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A

Hydroxy-thiophen-3-yl-acetonitrile

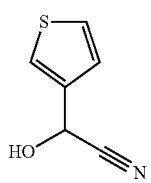

To a stirred suspension of KCN (18.6 g, 286 mmol) in methanol (100 mL) was added thiophene-3-carbaldehyde (20 mL, 178 mmol) at 0° C. under nitrogen atmosphere. Then acetic acid (4.4 mL) was added dropwise at 0° C. After 30 minutes, the mixture was warmed to 15° C. and stirred for 20 hours. $NaHCO_3$ (15 g) was added. The mixture was concentrated and extracted with ethyl acetate (200 mL). The organic mixture was washed with water (3×25 mL), brine (25 mL), dried over anhydrous sodium sulfate and concentrated to dryness. The residue was purified by column chromatography (ethyl acetate:petroleum ether, 1:10) to afford hydroxy-thiophen-3-yl-acetonitrile. (Yield 15 g, 60%).

LC-MS: $[M+Na]^+$ 162.

Step B

2-Amino-1-thiophen-3-yl-ethanol

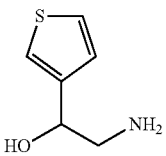

To a stirred suspension of LAH (8.7 g, 225 mmol) in dry THF (300 mL) was added a solution of hydroxy-thiophen-3-yl-acetonitrile (12.5 mL, 90 mmol) in dry THF (50 mL) dropwise at 0° C. under nitrogen atmosphere. Then the mixture was warmed to 25° C. and stirred overnight. After cooling to 10° C., $H_2O$ (8.7 mL) was added to the solution, followed by NaOH solution (8.7 mL, 15%), then $H_2O$ (26 mL). The reaction mixture was filtered and the filtration was concentrated to dryness to afford crude 2-amino-1-thiophen-3-yl-ethanol. (Yield 12.9 g, crude).

LC-MS: $[M+H]^+$ 144.

Step C (2-Hydroxy-2-thiophen-3-yl-ethyl)-carbamic acid tert-butyl ester

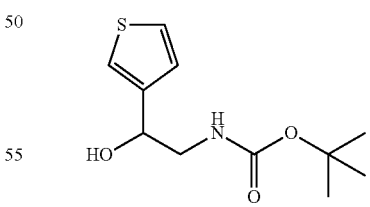

To a stirred solution of crude 2-amino-1-thiophen-3-yl-ethanol (12.9 g, crude) in THF (150 mL) was added $Boc_2O$ (21.6 g, 99 mmol). After stirring for 1 hour, the mixture was concentrated to dryness which was purified by column chromatography (ethyl acetate:petroleum ether, 1:5) to afford (2-hydroxy-2-thiophen-3-yl-ethyl)-carbamic acid tert-butyl ester. (Yield 15.3 g, 70%).

LC-MS: $[M+Na]^+$ 266.

Step D

[2-(1,3-Dioxo-1,3-dihydro-isoindol-2-yl)-2-thiophen-3-yl-ethyl]-carbamic acid tert-butyl ester

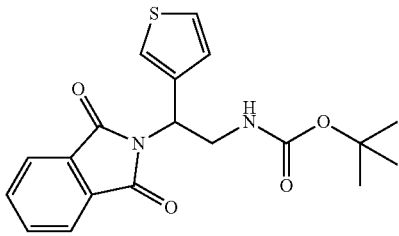 [SMILES: CC(C)(C)OC(=O)NCC(c1ccsc1)N1C(=O)c2ccccc2C1=O]

To a stirred solution of (2-hydroxy-2-thiophen-3-yl-ethyl)-carbamic acid tert-butyl ester (15.3 g, 63 mmol), pathalimide (9.5 g, 63 mmol), PPh₃ (21.4 g, 82 mmol) in THF (400 mL) was added DEAD (12.6 mL, 82 mmol) dropwise at 25° C. After 20 hours, the mixture was concentrated to dryness. The residue was purified by column chromatography (ethyl acetate:petroleum ether, 1:6) to afford [2-(1,3-dioxo-1,3-dihydro-isoindol-2-yl)-2-thiophen-3-yl-ethyl]-carbamic acid tert-butyl ester. (Yield 23 g, crude).

LC-MS: [M+Na]$^+$ 395.

Step E (2-Amino-2-thiophen-3-yl-ethyl)-carbamic acid tert-butyl ester

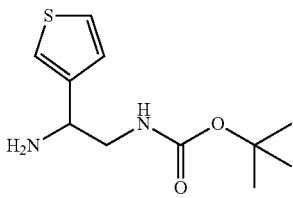 [SMILES: CC(C)(C)OC(=O)NCC(N)c1ccsc1]

To a stirred solution of [2-(1,3-dioxo-1,3-dihydro-isoindol-2-yl)-2-thiophen-3-yl-ethyl]-carbamic acid tert-butyl ester (23 g, crude) in THF (100 mL) and methanol (100 mL) was added hydrazine hydrate (63 g, 1.26 mol). The mixture was heated at 60° C. for 2 hours and then cooled to 20° C. The reaction mixture was filtered and the filtration was concentrated to dryness. The residue was purified by column chromatography (methanol:dichloromethane, 1:50) to afford (2-amino-2-thiophen-3-yl-ethyl)-carbamic acid tert-butyl ester. (Yield 8.6 g, 57% for the two steps).

LC-MS: [M+H]$^+$ 243.

Example 7

6-Chloro-3-(2-methylsulfanyl-pyrimidin-4-yl)-1H-pyrazolo[3,4-d]pyrimidine

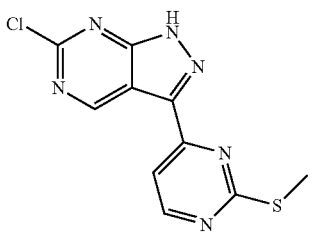 [SMILES: CSc1nccc(-c2n[nH]c3nc(Cl)ncc23)n1]

Step A (2,4-Dichloro-pyrimidin-5-yl)-(2-methylsulfanyl-pyrimidin-4-yl)-methanol

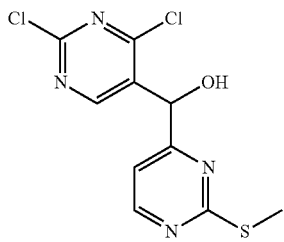 [SMILES: CSc1nccc(C(O)c2cnc(Cl)nc2Cl)n1]

To a stirred solution of 5-bromo-2,4-dichloropyrimidine (14.83 g, 65 mmol) in THF (200 mL) was added isopropyl-magnesium chloride (78 mL, 1M, 78 mmol) dropwise at −30° C. After 30 minutes, 2-(methylthio)pyrimidine-4-carbaldehyde (10 g, 65 mmol) was added to the mixture. The mixture was warmed to 0° C. and stirred for 1 hour. Then the reaction mixture was quenched with saturated ammonium chloride solution (20 mL) and extracted with ethyl acetate (200 mL). The filtrate was washed with water (3×25 mL), brine (25 mL), dried over anhydrous sodium sulfate, filtered, and concentrated to dryness. The residue was purified by column chromatography (silica, 20 g, 200-300 mesh, eluting with methanol:dichloromethane, 1:50) to afford (2,4-dichloro-pyrimidin-5-yl)-(2-methylsulfanyl-pyrimidin-4-yl)-methanol. (Yield 13.85 g, 71%).

LC-MS: [M+H]$^+$ 303.

Step B (2,4-Dichloro-pyrimidin-5-yl)-(2-methylsulfanyl-pyrimidin-4-yl)-methanone

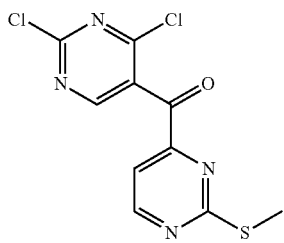 [SMILES: CSc1nccc(C(=O)c2cnc(Cl)nc2Cl)n1]

To a stirred solution of (2,4-dichloro-pyrimidin-5-yl)-(2-methylsulfanyl-pyrimidin-4-yl)-methanol (13.6 g, 45 mmol) in dichloromethane (160 mL) and methanol (40 mL) was added MnO₂ (55 g, 632 mmol), The mixture was heated at reflux for 16 hours. After cooling to room temperature, the precipitate was removed off by filtration. The filtrate was concentrated and the residue was purified by column chromatography (silica, 20 g, 200-300 mesh, eluting with methanol:dichloromethane, 1:200) to afford (2,4-dichloro-pyrimidin-5-yl)-(2-methylsulfanyl-pyrimidin-4-yl)-methanone. (Yield 9.52 g, 71%).

LC-MS: [M+H]$^+$ 300.9.

Step C

6-Chloro-3-(2-methylsulfanyl-pyrimidin-4-yl)-1H-pyrazolo[3,4-d]pyrimidine

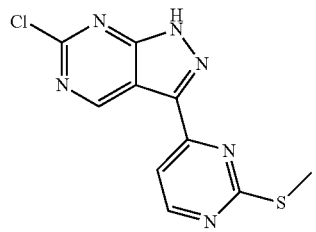 [SMILES: CSc1nccc(-c2n[nH]c3nc(Cl)ncc23)n1]

To a solution of (2,4-dichloro-pyrimidin-5-yl)-(2-methylsulfanyl-pyrimidin-4-yl)-methanone (9.52 g, 31.6 mmol) in THF (100 mL) was added hydrazine hydrate (2.3 g, 46 mmol) and DIPEA (5.9 g, 45.7 mmol). The mixture was heated at 50° C. for 4 hours, then concentrated to dryness. The resulting precipitate was collected by filtration and washed with water to give 6-chloro-3-(2-methylsulfanyl-pyrimidin-4-yl)-1H-pyrazolo[3,4-d]pyrimidine as a yellow solid. (Yield 7.8 g, 88%).

LC-MS: [M+H]+ 279.

Example 8

{4-[3-(2-Methylsulfanyl-pyrimidin-4-yl)-1H-pyrazolo[3,4-d]pyrimidin-6-ylamino]-cyclohexyl}-carbamic acid tert-butyl ester

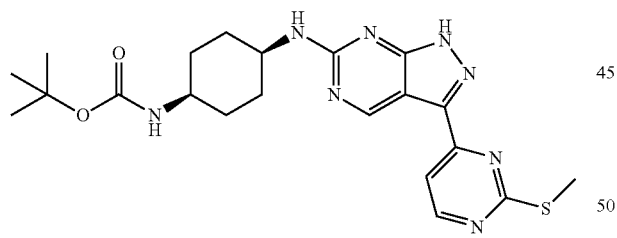

To a solution of 6-chloro-3-(2-methylsulfanyl-pyrimidin-4-yl)-1H-pyrazolo[3,4-d]pyrimidine (from Example 7 supra) (2.5 g, 9.0 mmol) in 2-propanol (100 mL) was added trans-tert-butyl 4-aminocyclohexylcarbamate (2.2 g, 9.9 mmol) followed by triethylamine (1.0 g, 9.9 mmol). The reaction mixture was stirred and heated at reflux for 15 hours. The solvent was then removed under reduced pressure. The residue was extracted with dichloromethane (200 mL) and washed with water (3×25 mL), dried over anhydrous sodium sulfate, filtered and concentrated to afford {4-[3-(2-methylsulfanyl-pyrimidin-4-yl)-1H-pyrazolo[3,4-d]pyrimidin-6-ylamino]-cyclohexyl}-carbamic acid tert-butyl ester. (Yield 2.5 g, 61.0%).

LC-MS: [M+H]+ 457.

Example 9

{4-[3-(2-Methanesulfinyl-pyrimidin-4-yl)-1H-pyrazolo[3,4-d]pyrimidin-6-ylamino]-cyclohexyl}-carbamic acid tert-butyl ester

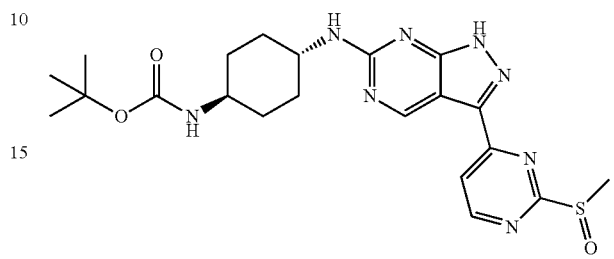

To a solution of {4-[3-(2-methylsulfanyl-pyrimidin-4-yl)-1H-pyrazolo[3,4-d]pyrimidin-6-ylamino]-cyclohexyl}-carbamic acid tert-butyl ester (from Example 8 supra) (800 mg, 1.8 mmol) in a mixture of dichloromethane and methanol (200 mL, 1:1) was added m-CPBA (710 mg, 1.8 mmol) slowly. The reaction mixture was stirred at room temperature for 25 minutes. The solvent was then removed under reduced pressure and the residue was purified by column chromatography (silica gel, 10 g, 200-300 mesh, eluting with dichloromethane:methanol, 50:1) to afford {4-[3-(2-Methanesulfinyl-pyrimidin-4-yl)-1H-pyrazolo[3,4-d]pyrimidin-6-ylamino]-cyclohexyl}-carbamic acid tert-butyl ester. (Yield 440 mg, 53.1%).

LC-MS: [M+H]+ 473.

Example 10

[3-(2-Methylsulfanyl-pyrimidin-4-yl)-1H-pyrazolo[3,4-d]pyrimidin-6-yl]-(2-morpholin-4-yl-ethyl)-amine

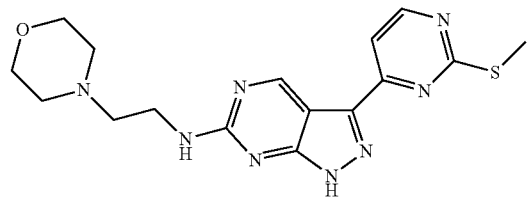 [SMILES: CSc1nccc(-c2n[nH]c3nc(NCCN4CCOCC4)ncc23)n1]

To a solution of 6-chloro-3-(2-methylsulfanyl-pyrimidin-4-yl)-1H-pyrazolo[3,4-d]pyrimidine (from Example 7 supra) (2 g, 7.19 mmol) in 2-propanol (100 mL) was added 2-morpholinoethanamine (1.0 g, 7.9 mmol) followed by triethylamine (800 mg, 7.9 mmol). The reaction mixture was stirred with heating at reflux for 6 hours. The solvent was then removed under reduced pressure. The residue was washed with 2-propanol and water to afford [3-(2-methylsulfanyl-pyrimidin-4-yl)-1H-pyrazolo[3,4-d]pyrimidin-6-yl]-(2-morpholin-4-yl-ethyl)-amine. (Yield 2.1 g, 80%).

LC-MS: [M+H]+ 373.

Example 11

[3-(2-Methanesulfonyl-pyrimidin-4-yl)-1H-pyrazolo[3,4-d]pyrimidin-6-yl]-(2-morpholin-4-yl-ethyl)-amine

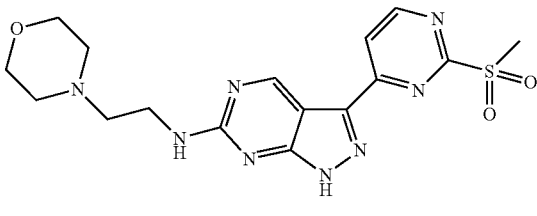 [SMILES: CS(=O)(=O)c1nccc(-c2n[nH]c3nc(NCCN4CCOCC4)ncc23)n1]

m-CPBA (873 mg, 4.3 mmol) was added slowly to a solution of [3-(2-methylsulfanyl-pyrimidin-4-yl)-1H-pyrazolo[3,4-d]pyrimidin-6-yl]-(2-morpholin-4-yl-ethyl)-amine (from Example 10 supra) (800 mg, 2.15 mmol) in mixture of dichloromethane and methanol (200 mL, 1:1). The reaction mixture was stirred at room temperature for 30 minutes. The solvent was then removed under reduced pressure and the solid was purified by column chromatography (silica gel, 20 g, 200-300 mesh, eluting with dichloromethane:methanol 8:1 to 4:1) to afford [3-(2-methanesulfonyl-pyrimidin-4-yl)-1H-pyrazolo[3,4-d]pyrimidin-6-yl]-(2-morpholin-4-yl-ethyl)-amine. (Yield 810 mg, 93.4%).

LC-MS: $[M+H]^+$ 405.

Example 12

4-[3-(2-Methylsulfanyl-pyrimidin-4-yl)-1H-pyrazolo[3,4-d]pyrimidin-6-ylamino]-piperidine-1-carboxylic acid tert-butyl ester

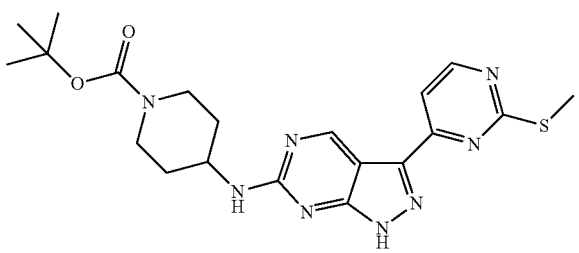 [SMILES: CSc1nccc(-c2n[nH]c3nc(NC4CCN(C(=O)OC(C)(C)C)CC4)ncc23)n1]

To a solution of 6-chloro-3-(2-methylsulfanyl-pyrimidin-4-yl)-1H-pyrazolo[3,4-d]pyrimidine (from Example 7 supra) (500 mg, 1.8 mmol) in 2-propanol (40 mL) was added tert-butyl 4-aminopiperidine-1-carboxylate (395 mg, 2.0 mmol) followed by triethylamine (198 mg, 2.0 mmol). The reaction mixture was stirred with heating at reflux for 15 hours. The solvent was then removed under reduced pressure. The residue was extracted with dichloromethane (3×30 mL), washed with water (5 mL), dried over anhydrous sodium sulfate, filtered, and concentrated to afford 4-[3-(2-methylsulfanyl-pyrimidin-4-yl)-1H-pyrazolo[3,4-d]pyrimidin-6-ylamino]-piperidine-1-carboxylic acid tert-butyl ester. (Yield 700 mg, 88.2%).

LC-MS: $[M+H]^+$ 443.

Example 13

4-[3-(2-Methanesulfinyl-pyrimidin-4-yl)-1H-pyrazolo[3,4-d]pyrimidin-6-ylamino]-piperidine-1-carboxylic acid tert-butyl ester

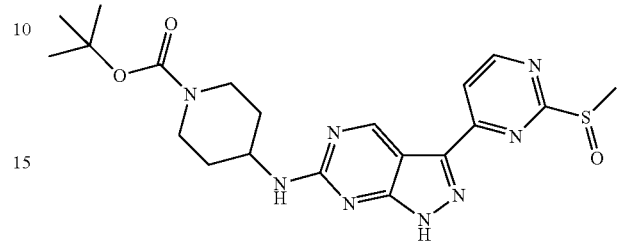

m-CPBA (428 mg, 2.4 mmol) was added slowly to a solution of 4-[3-(2-methylsulfanyl-pyrimidin-4-yl)-1H-pyrazolo[3,4-d]pyrimidin-6-ylamino]-piperidine-1-carboxylic acid tert-butyl ester (from Example 12 supra) (550 mg, 1.2 mmol) in a mixture of dichloromethane and methanol (100 mL, 1:1). The reaction mixture was stirred at room temperature for 20 minutes. The solvent was then removed under reduced pressure and the solid was purified by column chromatography (silica gel, 10 g, 200-300 mesh, eluting with dichloromethane:methanol, 50:1) to afford 4-[3-(2-methanesulfinyl-pyrimidin-4-yl)-1H-pyrazolo[3,4-d]pyrimidin-6-ylamino]-piperidine-1-carboxylic acid tert-butyl ester. (Yield 180 mg, 31.5%).

LC-MS: $[M+Na]^+$ 481.

Example 14

4-{[3-(2-Methylsulfanyl-pyrimidin-4-yl)-1H-pyrazolo[3,4-d]pyrimidin-6-ylamino]-methyl}-piperidine-1-carboxylic acid tert-butyl ester

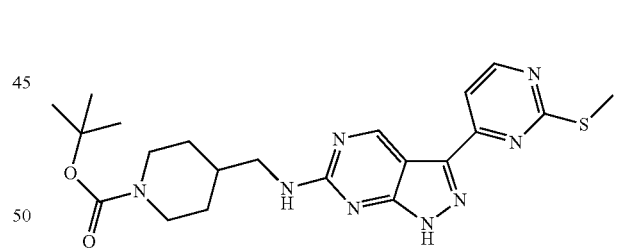

To a solution of 6-chloro-3-(2-methylsulfanyl-pyrimidin-4-yl)-1H-pyrazolo[3,4-d]pyrimidine (from Example 7 supra) (500 mg, 1.8 mmol) in 2-propanol (40 mL) was added tert-butyl 4-(aminomethyl)piperidine-1-carboxylate (420 mg, 2.0 mmol) followed by triethylamine (200 mg, 2.0 mmol). The reaction mixture was stirred at reflux for 15 hours. The solvent was then removed under reduced pressure. The residue was extracted with dichloromethane (3×30 mL), washed with water (5 mL), dried over anhydrous sodium sulfate, filtered, and concentrated to afford 4-{[3-(2-methylsulfanyl-pyrimidin-4-yl)-1H-pyrazolo[3,4-d]pyrimidin-6-ylamino]-methyl}-piperidine-1-carboxylic acid tert-butyl ester. (Yield 700 mg, 85.3%)

LC-MS: $[M+H]^+$ 457. .

Example 15

4-{[3-(2-Methanesulfinyl-pyrimidin-4-yl)-1H-pyrazolo[3,4-d]pyrimidin-6-ylamino]-methyl}-piperidine-1-carboxylic acid tert-butyl ester

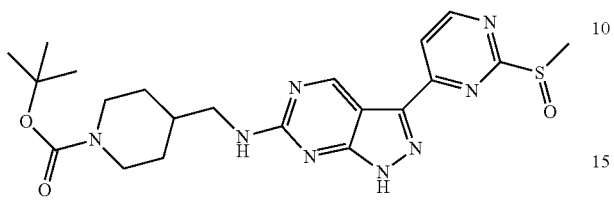

m-CPBA (339 mg, 1.98 mmol) was added slowly to a solution of 4-{[3-(2-methylsulfanyl-pyrimidin-4-yl)-1H-pyrazolo[3,4-d]pyrimidin-6-ylamino]-methyl}-piperidine-1-carboxylic acid tert-butyl ester (from Example 14 supra) (450 mg, 0.99 mmol) in a mixture of dichloromethane and methanol (80 mL, 1:1). The reaction mixture was stirred at room temperature for 20 minutes. The solvent was then removed under reduced pressure and the solid was purified by column chromatography (silica gel, 15 g, 200-300 mesh, eluting with dichloromethane:methanol, 50:1 to 30:1) to afford 4-{[3-(2-methanesulfinyl-pyrimidin-4-yl)-1H-pyrazolo[3,4-d]pyrimidin-6-ylamino]-methyl}-piperidine-1-carboxylic acid tert-butyl ester. (Yield 150 mg, 32.3%).

LC-MS: [M+H]$^+$ 473; [M+Na]$^+$ 495.

Example 16

[3-(2-Methylsulfanyl-pyrimidin-4-yl)-1H-pyrazolo[3,4-d]pyrimidin-6-yl]-(2-pyrrolidin-1-yl-ethyl)-amine

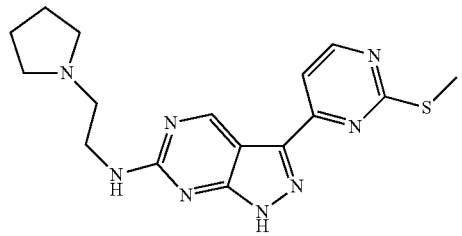 [SMILES: CSc1nccc(-c2n[nH]c3nc(NCCN4CCCC4)ncc23)n1]

To a solution of 6-chloro-3-(2-methylsulfanyl-pyrimidin-4-yl)-1H-pyrazolo[3,4-d]pyrimidine (from Example 7 supra) (500 mg, 1.8 mmol) in 2-propanol (40 mL) was added 2-(pyrrolidin-1-yl)ethanamine (226 mg, 2.0 mmol) followed by triethylamine (200 mg, 2.0 mmol). The reaction mixture was stirred at reflux for 15 hours and the solvent was removed under reduced pressure. The residue was extracted with dichloromethane (3×30 mL), washed with water (5 mL), dried over anhydrous sodium sulfate, filtered, and concentrated to afford [3-(2-methylsulfanyl-pyrimidin-4-yl)-1H-pyrazolo[3,4-d]pyrimidin-6-yl]-(2-pyrrolidin-1-yl-ethyl)-amine. (Yield 500 mg, 78.1%).

LC-MS: [M+H]$^+$ 357.

Example 17

[3-(2-Methanesulfonyl-pyrimidin-4-yl)-1H-pyrazolo[3,4-d]pyrimidin-6-yl]-(2-pyrrolidin-1-yl-ethyl)-amine

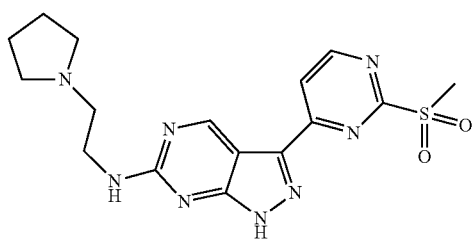 [SMILES: CS(=O)(=O)c1nccc(-c2n[nH]c3nc(NCCN4CCCC4)ncc23)n1]

m-CPBA (200 mg, 1.1 mmol) was added slowly to a solution of [3-(2-methylsulfanyl-pyrimidin-4-yl)-1H-pyrazolo[3,4-d]pyrimidin-6-yl]-(2-pyrrolidin-1-yl-ethyl)-amine (from Example 16 supra) (200 mg, 0.56 mmol) in a mixture of dichloromethane and methanol (40 mL, 1:1). The reaction mixture was stirred at room temperature for 25 minutes, then the solvent was removed under reduced pressure and the solid was purified by column chromatography (silica gel, 10 g, 200-300 mesh, eluting with dichloromethane:methanol, 50:1) to afford [3-(2-methanesulfonyl-pyrimidin-4-yl)-1H-pyrazolo[3,4-d]pyrimidin-6-yl]-(2-pyrrolidin-1-yl-ethyl)-amine. (Yield 70 mg, 32.1%).

LC-MS: [M+H]$^+$ 389.

Example 18

{4-[3-(2-Methylsulfanyl-pyrimidin-4-yl)-1H-pyrazolo[3,4-d]pyrimidin-6-ylamino]-cyclohexyl}-carbamic acid tert-butyl ester

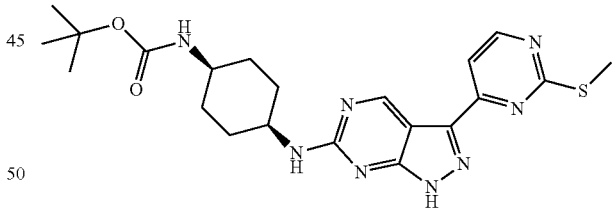

To a solution of 6-chloro-3-(2-methylsulfanyl-pyrimidin-4-yl)-1H-pyrazolo[3,4-d]pyrimidine (from Example 7 supra) (500 mg, 1.80 mmol) in 2-propanol (50 mL) was added cis-tert-butyl 4-aminocyclohexylcarbamate (425 mg, 1.98 mmol) followed by triethylamine (200 mg, 1.98 mmol). The reaction mixture was stirred at reflux for 15 hours and the solvent was then removed under reduced pressure. The residue was suspended in dichloromethane (50 mL), washed with water (3×25 mL), dried over anhydrous sodium sulfate, filtered, and concentrated to afford {4-[3-(2-methylsulfanyl-pyrimidin-4-yl)-1H-pyrazolo[3,4-d]pyrimidin-6-ylamino]-cyclohexyl}-carbamic acid tert-butyl ester. (Yield 550 mg, 67.1%).

LC-MS: [M+H]$^+$ 457.

Example 19

{4-[3-(2-Methanesulfinyl-pyrimidin-4-yl)-1H-pyrazolo[3,4-d]pyrimidin-6-ylamino]-cyclohexyl}-carbamic acid tert-butyl ester

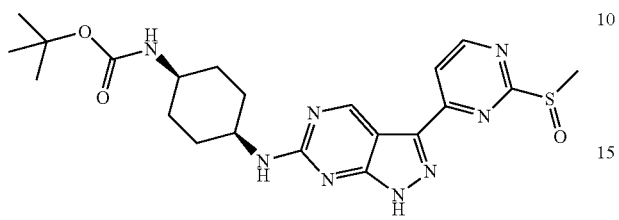

m-CPBA (490 mg, 2.41 mmol) was added slowly to a solution of {-4-[3-(2-methylsulfanyl-pyrimidin-4-yl)-1H-pyrazolo[3,4-d]pyrimidin-6-ylamino]-cyclohexyl}-carbamic acid tert-butyl ester (from Example 18 supra) (550 mg, 1.21 mmol) in a mixture of dichloromethane and methanol (20 mL, 1:1). The reaction mixture was stirred at room temperature for 25 minutes. The solvent was then removed under reduced pressure and the solid was purified by column chromatography (silica gel, 20 g, 200-300 mesh, eluting with dichloromethane:methanol, 5:1) to afford {4-[3-(2-methanesulfinyl-pyrimidin-4-yl)-1H-pyrazolo[3,4-d]pyrimidin-6-ylamino]-cyclohexyl}-carbamic acid tert-butyl ester. (Yield 300 mg, 52.9%).

LC-MS: [M+H]$^+$ 473.

Example 20

2-[3-(2-Methylsulfanyl-pyrimidin-4-yl)-1H-pyrazolo[3,4-d]pyrimidin-6-ylamino]-ethanol

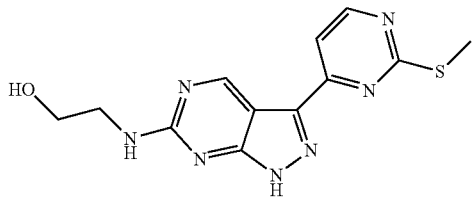 [SMILES: CSc1nccc(-c2n[nH]c3nc(NCCO)ncc23)n1]

To a solution of 6-chloro-3-(2-methylsulfanyl-pyrimidin-4-yl)-1H-pyrazolo[3,4-d]pyrimidine (from Example 7 supra) (590 mg, 2.12 mmol) in 2-propanol (20 mL) was added 2-aminoethanol (142 mg, 2.33 mmol) followed by triethylamine (235 mg, 2.33 mmol). The reaction mixture was stirred at reflux for 16 hours and the solvent was then removed under reduced pressure. The residue was washed with 2-propanol (1 mL) and dried by evaporation to afford 2-[3-(2-methylsulfanyl-pyrimidin-4-yl)-1H-pyrazolo[3,4-d]pyrimidin-6-ylamino]-ethanol. (Yield 0.7 g, crude). LC-MS: [M+H]$^+$ 304.

Example 21

2-[3-(2-Methanesulfinyl-pyrimidin-4-yl)-1H-pyrazolo[3,4-d]pyrimidin-6-ylamino]-ethanol

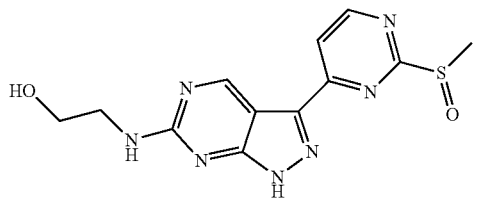 [SMILES: CS(=O)c1nccc(-c2n[nH]c3nc(NCCO)ncc23)n1]

m-CPBA (797 mg, 4.62 mmol) was added slowly to a solution of 2-[3-(2-Methylsulfanyl-pyrimidin-4-yl)-1H-pyrazolo[3,4-d]pyrimidin-6-ylamino]-ethanol (from Example 20 supra) (0.7 g, crude) in a mixture of dichloromethane and methanol (40 mL, 1:1). The reaction mixture was stirred at room temperature for 30 minutes. The solvent was then removed under reduced pressure and the solid was purified by column chromatography (silica gel, 10 g, 200-300 mesh, eluting with dichloromethane:methanol, 5:1) to afford 2-[3-(2-methanesulfinyl-pyrimidin-4-yl)-1H-pyrazolo[3,4-d]pyrimidin-6-ylamino]-ethanol (Yield 1.9 g, crude). LC-MS: [M+H]$^+$ 320.

Example 22

N,N-Dimethyl-N'-[3-(2-methylsulfanyl-pyrimidin-4-yl)-1H-pyrazolo[3,4-d]pyrimidin-6-yl]-ethane-1,2-diamine

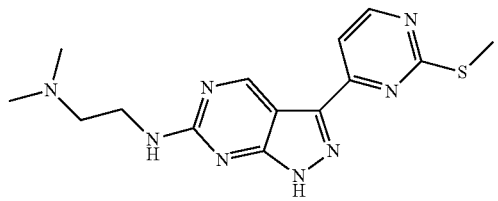

To a solution of 6-chloro-3-(2-methylsulfanyl-pyrimidin-4-yl)-1H-pyrazolo[3,4-d]pyrimidine (from Example 7 supra) (400 mg, 1.43 mmol) in 2-propanol (40 mL) was added N,N-dimethylethane-1,2-diamine (139 mg, 1.58 mmol) followed by triethylamine (159 mg, 1.57 mmol). The reaction mixture was stirred at reflux for 15 hours and the solvent was then removed under reduced pressure. The residue was extracted with dichloromethane (3×30 mL), washed with water (5 mL), dried over anhydrous sodium sulfate, filtered, and concentrated to afford N,N-dimethyl-N'-[3-(2-methylsulfanyl-pyrimidin-4-yl)-1H-pyrazolo[3,4-d]pyrimidin-6-yl]-ethane-1,2-diamine (Yield 356 mg, 75%).

LC-MS: [M+H]$^+$ 331.

Example 23

N'-[3-(2-Methanesulfonyl-pyrimidin-4-yl)-1H-pyrazolo[3,4-d]pyrimidin-6-yl]-N,N-dimethyl-ethane-1,2-diamine

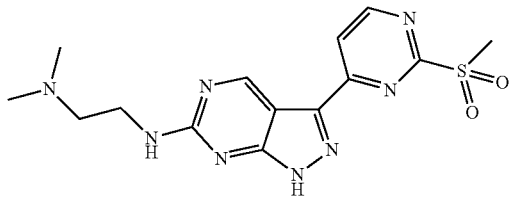 [SMILES: CN(C)CCNc1ncc2c(-c3ccnc(S(C)(=O)=O)n3)n[nH]c2n1]

m-CPBA (371 mg, 2.16 mmol) was added slowly to a solution of N,N-dimethyl-N'-[3-(2-methylsulfanyl-pyrimidin-4-yl)-1H-pyrazolo[3,4-d]pyrimidin-6-yl]-ethane-1,2-diamine (from Example 22 supra) (356 mg, 1.08 mmol) in a mixture of dichloromethane and methanol (40 mL, 1:1). The reaction mixture was stirred at room temperature for 25 minutes. The solvent was then removed under reduced pressure and the solid was purified by column chromatography (silica gel, 10 g, 200-300 mesh, eluting with dichloromethane:methanol, 3:1) to afford N'-[3-(2-methanesulfonyl-pyrimidin-4-yl)-1H-pyrazolo[3,4-d]pyrimidin-6-yl]-N,N-dimethyl-ethane-1,2-diamine. (Yield 160 mg, crude).

LC-MS: [M+H]$^+$ 363.

Example 24

[3-(2-Methylsulfanyl-pyrimidin-4-yl)-1H-pyrazolo[3,4-d]pyrimidin-6-yl]-(2-piperidin-1-yl-ethyl)-amine

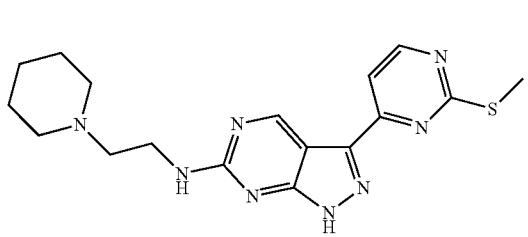 [SMILES: CSc1nccc(-c2n[nH]c3nc(NCCN4CCCCC4)ncc23)n1]

To a solution of 6-chloro-3-(2-methylsulfanyl-pyrimidin-4-yl)-1H-pyrazolo[3,4-d]pyrimidine (from Example 7 supra) (450 mg, 1.61 mmol) in 2-propanol (40 mL) was added 2-(piperidin-1-yl)ethanamine (227 mg, 1.77 mmol) followed by triethylamine (160 mg, 1.58 mmol). The reaction mixture was stirred at reflux for 15 hours and the solvent was then removed under reduced pressure. The residue was extracted with dichloromethane (3×30 mL), washed with water (5 mL), dried over anhydrous sodium sulfate, filtered and concentrated to afford [3-(2-methylsulfanyl-pyrimidin-4-yl)-1H-pyrazolo[3,4-d]pyrimidin-6-yl]-(2-piperidin-1-yl-ethyl)-amine. (Yield 411 mg, crude).

LC-MS: [M+H]$^+$ 371.

Example 25

[3-(2-Methanesulfonyl-pyrimidin-4-yl)-1H-pyrazolo[3,4-d]pyrimidin-6-yl]-(2-piperidin-1-yl-ethyl)-amine

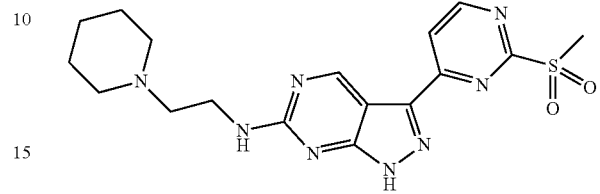

m-CPBA (341 mg, 1.98 mmol) was added portion wise to the solution of [3-(2-methylsulfanyl-pyrimidin-4-yl)-1H-pyrazolo[3,4-d]pyrimidin-6-yl]-(2-piperidin-1-yl-ethyl)-amine (from Example 24 supra) (367 mg, 0.99 mmol) in a mixture of dichloromethane and methanol (40 mL, 1:1). The reaction mixture was stirred at room temperature for 30 minutes. The solvent was then removed under reduced pressure and the solid was purified by column chromatography (silica gel, 10 g, 100-200 mesh, eluting with dichloromethane:methanol, 10:1) to afford [3-(2-methanesulfonyl-pyrimidin-4-yl)-1H-pyrazolo[3,4-d]pyrimidin-6-yl]-(2-piperidin-1-yl-ethyl)-amine. (Yield 196 mg, 49%).

LC-MS: [M+H]$^+$ 403.

Example 26

4-{2-[3-(2-Methylsulfanyl-pyrimidin-4-yl)-1H-pyrazolo[3,4-d]pyrimidin-6-ylamino]-ethyl}-piperazine-1-carboxylic acid tert-butyl ester

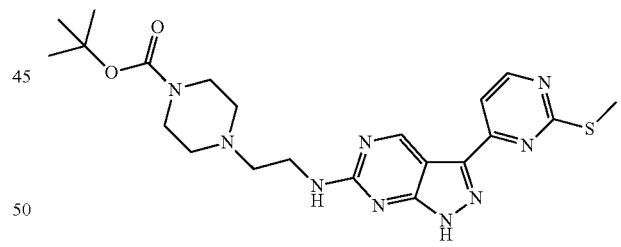

To a solution of 6-chloro-3-(2-methylsulfanyl-pyrimidin-4-yl)-1H-pyrazolo[3,4-d]pyrimidine (from Example 7 supra) (500 mg, 1.79 mmol) in 2-propanol (40 mL) was added tert-butyl 4-(2-aminoethyl)piperazine-1-carboxylate (613 mg, 1.97 mmol) followed by triethylamine (200 mg, 1.98 mmol). The reaction mixture was stirred at reflux for 15 hours and the solvent was then removed under reduced pressure. The residue was extracted with dichloromethane (3×30 mL), washed with water (5 mL), dried over anhydrous sodium sulfate, filtered, and concentrated to afford 4-{2-[3-(2-methylsulfanyl-pyrimidin-4-yl)-1H-pyrazolo[3,4-d]pyrimidin-6-ylamino]-ethyl}-piperazine-1-carboxylic acid tert-butyl ester. (Yield 600 mg, crude).

LC-MS: [M+H]$^+$ 472.

Example 27

4-{2-[3-(2-Methanesulfonyl-pyrimidin-4-yl)-1H-pyrazolo[3,4-d]pyrimidin-6-ylamino]-ethyl}-piperazine-1-carboxylic acid tert-butyl ester

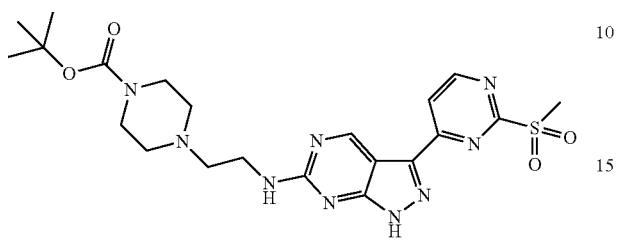

m-CPBA (365 mg, 2.12 mmol) was added portion wise to a solution of 4-{2-[3-(2-methylsulfanyl-pyrimidin-4-yl)-1H-pyrazolo[3,4-d]pyrimidin-6-ylamino]-ethyl}-piperazine-1-carboxylic acid tert-butyl ester (from Example 26 supra) (500 mg, 1.06 mmol) in a mixture of dichloromethane and methanol (40 mL, 1:1). The reaction mixture was stirred at room temperature for 30 minutes. The solvent was then removed under reduced pressure and the solid was purified by column chromatography (silica gel, 10 g, 100-200 mesh, eluting with dichloromethane:methanol, 10:1) to afford 4-{2-[3-(2-methanesulfonyl-pyrimidin-4-yl)-1H-pyrazolo[3,4-d]pyrimidin-6-ylamino]-ethyl}-piperazine-1-carboxylic acid tert-butyl ester. (Yield 153 mg, 28.6%).

LC-MS: [M+H]+ 504.

Example 28

(6-Bromo-pyridin-2-yl)-(2,4-dichloro-pyrimidin-5-yl)-methanol

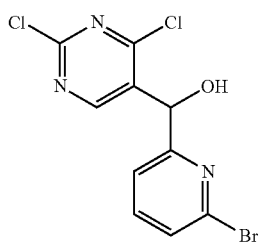 [SMILES: OC(c1cccc(Br)n1)c1cnc(Cl)nc1Cl]

To a stirred solution of 5-bromo-2,4-dichloropyrimidine (11.4 g, 50 mmol) in THF (200 mL) at −30° C., was added dropwise isopropyl magnesium chloride (25 mL, 2 M in THF, 50 mmol) and the mixture was stirred at −30° C. for 20 minutes. Then a solution of 6-bromopicolinaldehyde (9.3 g, 50 mmol) in THF (10 mL) was added and the mixture was warmed to 0° C. and stirred for another 40 minutes. The reaction was quenched by adding saturated aqueous NH4Cl solution and the resulting mixture was extracted with ethyl acetate (3×300 mL). The organic solutions were then washed with brine. The organic phase was dried with anhydrous MgSO4, filtered and concentrated under reduced pressure to give crude (6-bromo-pyridin-2-yl)-(2,4-dichloro-pyrimidin-5-yl)-methanol as a light yellow oil. (Yield 16.1 g)

1H NMR (300 MHz, CDCl3): δ 8.70 (s, 1H), 7.61-7.56 (m, 1H), 7.50-7.48 (m, 1H), 7.28-7.26 (m, 1H), 6.09 (d, 1H, J=4.8 Hz), 4.55 (d, 1H, J=5.1 Hz). LC-MS: [M+H]+ 334.

Example 29

(6-Bromo-pyridin-2-yl)-(2,4-dichloro-pyrimidin-5-yl)-methanone

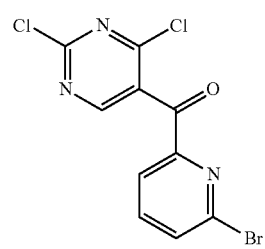 [SMILES: O=C(c1cccc(Br)n1)c1cnc(Cl)nc1Cl]

To a stirred solution of crude (6-bromo-pyridin-2-yl)-(2,4-dichloro-pyrimidin-5-yl)-methanol (from Example 28 supra) (16.1 g, crude) in dichloromethane (200 mL), water (20 mL) was added followed by NaHCO3 (2.1 g, 25 mmol), TBAB (485 mg, 1.5 mmol) and TEMPO (90 mg, 0.5 mmol). The mixture was then cooled to 0° C. and NaClO (70 mL, active chloride >6.0%) was added slowly and the resulting mixture was stirred for 30 minutes. The mixture was poured into water and extracted with dichloromethane. The organic phase was dried over anhydrous MgSO4, filtered and concentrated. The residue was purified by column chromatography (silica gel, eluting with ethyl acetate:petroleum ether, 1:20) to give (6-bromo-pyridin-2-yl)-(2,4-dichloro-pyrimidin-5-yl)-methanone as a white solid. (Yield 12.7 g, 76% over two steps).

1H NMR (300 MHz, CDCl3): δ 8.79 (s, 1H), 8.19 (dd, 1H, J1=7.2 Hz, J2=1.2 Hz), 7.87-7.76 (m, 1H). LC-MS: [M+H]+ 332.

Example 30

3-(6-Bromo-pyridin-2-yl)-6-chloro-1H-pyrazolo[3,4-d]pyrimidine

To a stirred solution of (6-bromo-pyridin-2-yl)-(2,4-dichloro-pyrimidin-5-yl)-methanone (from Example 29 supra) (2.42 g, 7.54 mmol) in THF (30 mL) was added hydrazine (454 mg, 9.08 mmol) and the mixture was stirred for 30 minutes at room temperature and then at 50° C. for 1 hour. The solvent was then removed and the solid was washed with water and dried to give crude 3-(6-bromo-pyridin-2-yl)-6-chloro-1H-pyrazolo[3,4-d]pyrimidine as a yellow solid. (Yield 1.7 g, crude).

$^1$H NMR (300 MHz, $d_6$-DMSO): δ 14.71 (brs, 1H), 9.59 (s, 1H), 8.23-8.20 (m, 1H), 7.98-7.93 (m, 1H), 7.78-7.75 (m, 1H). LC-MS: [M+H]$^+$ 310.

Example 31

3-(6-Bromo-pyridin-2-yl)-6-chloro-1-(2-trimethylsilanyl-ethoxymethyl)-1H-pyrazolo[3,4-d]pyrimidine

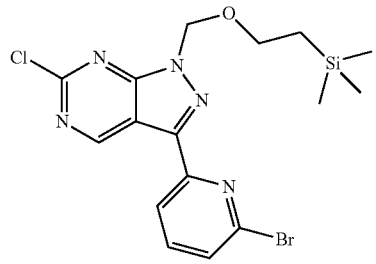 [SMILES: C[Si](C)(C)CCOCn1nc(-c2cccc(Br)n2)c2cnc(Cl)nc21]

To a mixture of NaH (1.3 mg, 37.6 mmol, 60%) in DMF (80 mL) was added slowly the solution of crude 3-(6-bromo-pyridin-2-yl)-6-chloro-1H-pyrazolo[3,4-d]pyrimidine (from Example 30 supra) (5.83 g, 18.8 mmol) in DMF (40 mL) at 5° C. The ice-bath was removed and the mixture was stirred for 20 minutes. Then (2-(chloromethoxy)ethyl)trimethylsilane (4.06 g, 24.4 mmol) was added. This solution was stirred for 12 hours at room temperature. The solvent was removed under reduced pressure. The residue was partitioned between saturated aqueous NH$_4$Cl and dichloromethane (3×20 mL). The combined organics was dried over anhydrous MgSO$_4$, filtered and concentrated under reduced pressure. The residue was purified by column chromatography (silica gel, 60 g, 200-300 mesh, eluting with ethyl acetate:petroleum ether, 1:10) to give 3-(6-bromo-pyridin-2-yl)-6-chloro-1-(2-trimethylsilanyl-ethoxymethyl)-1H-pyrazolo[3,4-d]pyrimidine as a white solid. (Yield 4.9 g, 84%).

$^1$H NMR (300 MHz, CDCl$_3$): δ 9.81 (s, 1H), 8.20-8.17 (m, 1H), 7.71-7.66 (m, 1H), 7.56-7.53 (m, 1H), 5.84 (s, 2H), 3.74-3.68 (m, 2H), 1.00-0.94 (m, 2H), −0.03 (s, 9H).

Example 32

[3-(6-Bromo-pyridin-2-yl)-1-(2-trimethylsilanyl-ethoxymethyl)-1H-pyrazolo[3,4-d]pyrimidin-6-yl]-(2-morpholin-4-yl-ethyl)-amine

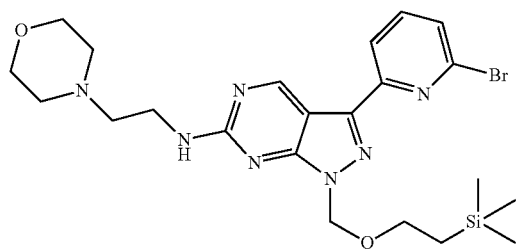 [SMILES: C[Si](C)(C)CCOCn1nc(-c2cccc(Br)n2)c2cnc(NCCN3CCOCC3)nc21]

SEM-Cl (5.15 g, 30.9 mmol) was added dropwise to a solution of 3-(6-bromo-pyridin-2-yl)-6-chloro-1H-pyrazolo[3,4-d]pyrimidine (from Example 30 supra) (8.0 g, 25.8 mmol) and TEA (10.4 g, 103 mmol) in DMF (170 mL). The reaction was stirred at room temperature for 40 minutes. Then 2-morpholinoethanamine (4.03 g, 30.9 mmol) was added dropwise to the above solution. The mixture was heated at 55° C. for 12 hours. After cooling to room temperature, the reaction mixture was poured into water (500 mL) and extracted with ethyl acetate. Ethyl acetate solution was evaporated and purified by chromatography (silica gel, dichloromethane:MeOH, 50:1) to afford [3-(6-bromo-pyridin-2-yl)-1-(2-trimethylsilanyl-ethoxymethyl)-1H-pyrazolo[3,4-d]pyrimidin-6-yl]-(2-morpholin-4-yl-ethyl)-amine as yellow solid. (Yield 5.6 g, 41%).

LC-MS: [M+H]$^+$ 535.

Example 33

{4-[3-(6-Bromo-pyridin-2-yl)-1-(2-trimethylsilanyl-ethoxymethyl)-1H-pyrazolo[3,4-d]pyrimidin-6-ylamino]-cyclohexyl}-carbamic acid tert-butyl ester

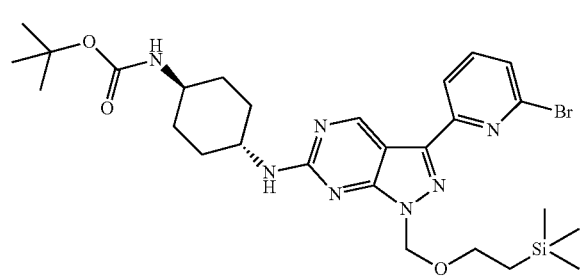 [SMILES: CC(C)(C)OC(=O)N[C@H]1CC[C@H](Nc2ncc3c(-c4cccc(Br)n4)nn(COCC[Si](C)(C)C)c3n2)CC1]

The mixture of 3-(6-bromo-pyridin-2-yl)-6-chloro-1-(2-trimethylsilanyl-ethoxymethyl)-1H-pyrazolo[3,4-d]pyrimidine (from Example 31 supra) (2.65 g, 6.01 mmol), tert-butyl (1r,4r)-4-aminocyclohexylcarbamate (1.53 g, 7.14 mmol) and Et$_3$N (1.4 mL, 9.7 mmol) in IPA (60 mL) was heated at reflux for 16 hours. After cooling to room temperature, the reaction mixture was filtered and solid dried to give {4-[3-(6-bromo-pyridin-2-yl)-1-(2-trimethylsilanyl-ethoxymethyl)-1H-pyrazolo[3,4-d]pyrimidin-6-ylamino]-cyclohexyl}-carbamic acid tert-butyl ester as white powder. (Yield 3.3 g, 89%).

Example 34

3-(6-Bromo-pyridin-2-yl)-6-chloro-1-trityl-1H-pyrazolo[3,4-d]pyrimidine

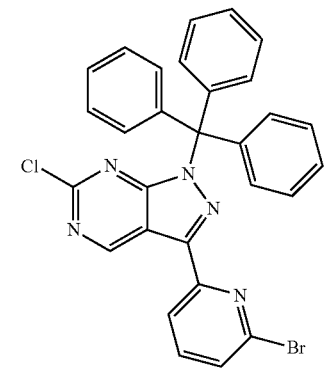

A solution of trityl chloride (8.5 g, 30.5 mmol) in DMF (80 mL) was added dropwise to the solution of 3-(6-bromo-pyridin-2-yl)-6-chloro-1H-pyrazolo[3,4-d]pyrimidine (from Example 30 supra) (8.0 g, 25.7 mmol) and Et₃N (12 mL, 83.2 mmol) in DMF (100 mL) at room temperature. The reaction mixture was stirred at room temperature for 2 hours then poured into water and extracted with ethyl acetate. The organic solution was dried with anhydrous Na₂SO₄. After filtration and concentration, the residue was purified by column chromatography (silica gel, petroleum ether:ethyl acetate, 20:1) to give 3-(6-bromo-pyridin-2-yl)-6-chloro-1-trityl-1H-pyrazolo[3,4-d]pyrimidine as a white powder. (Yield 3.8 g, 27%).

Example 35

{4-[3-(6-Bromo-pyridin-2-yl)-1-trityl-1H-pyrazolo [3,4-d]pyrimidin-6-ylamino]-cyclohexyl}-carbamic acid tert-butyl ester

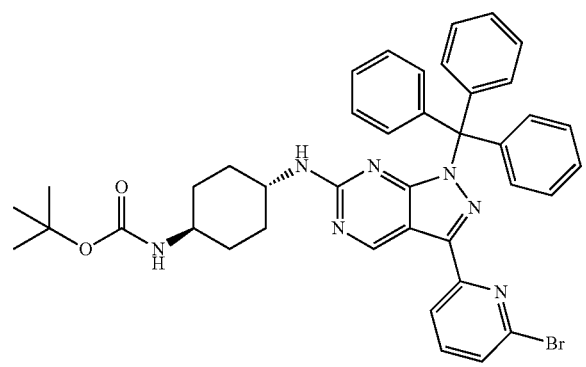 [SMILES: CC(C)(C)OC(=O)N[C@H]1CC[C@H](Nc2ncc3c(-c4cccc(Br)n4)nn(C(c4ccccc4)(c4ccccc4)c4ccccc4)c3n2)CC1]

The mixture of 3-(6-bromo-pyridin-2-yl)-6-chloro-1-trityl-1H-pyrazolo[3,4-d]pyrimidine (from Example 34 supra) (3.8 g, 6.89 mmol), tert-butyl (1r,4r)-4-aminocyclohexylcarbamate (1.8 g, 8.40 mmol) and Et₃N (1.2 mL, 8.3 mmo,) in IPA (80 mL) was stirred at 90° C. for 15 hours. The reaction was cooled to room temperature and the precipitate was collected by filtration to give {-4-[3-(6-bromo-pyridin-2-yl)-1-trityl-1H-pyrazolo[3,4-d]pyrimidin-6-ylamino]-cyclohexyl}-carbamic acid tert-butyl ester as white powder. (Yield 1.5 g, 30%).

Example 36

(3-Bromo-phenyl)-(2,4-dichloro-pyrimidin-5-yl)-methanol

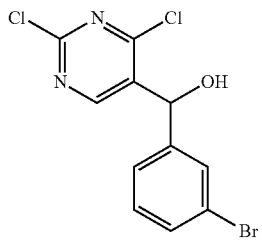 [SMILES: OC(c1cccc(Br)c1)c1cnc(Cl)nc1Cl]

To the solution of 5-bromo-2,4-dichloropyrimidine (22.8 g, 0.10 mol) in dry THF (150 mL), i-PrMgCl (50 mL, 0.10 mol, 2M in THF) was added dropwise at −35° C. under N₂ atmosphere. After addition, the mixture was stirred for another one hour. Then 3-bromobenzaldehyde (18.5 g, 0.10 mol) was added in one portion. The resulting mixture was stirred for another two hours at −35° C. The reaction was quenched by water (10 mL), and filtered. The filtrate was extracted with ethyl acetate (3×300 mL). The combined organic phase was washed with water (300 mL), brine (200 mL) and dried over Na₂SO₄. The drying agent was removed by filtration and the residue was evaporated to give (3-bromo-phenyl)-(2,4-dichloro-pyrimidin-5-yl)-methanol as yellow oil. (Yield 33 g, 98.8%).

$^1$H NMR (300 MHz, CDCl₃): δ 8.86 (s, 1H), 7.54-7.46 (m, 2H), 7.35-7.22 (m, 2H), 6.04 (s, 1H), 2.72 (d, 1H, J=3.6 Hz). LC-MS: [M+H]$^+$ 332.9.

Example 37

(3-Bromo-phenyl)-(2,4-dichloro-pyrimidin-5-yl)-methanone

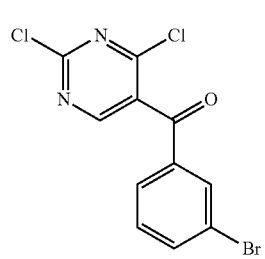 [SMILES: O=C(c1cccc(Br)c1)c1cnc(Cl)nc1Cl]

To the solution of (3-bromo-phenyl)-(2,4-dichloro-pyrimidin-5-yl)-methanol (from Example 36 supra) (33 g, 0.098 mol) in dichloromethane (300 mL) was added water (30 mL), NaHCO₃ (3.8 g, 0.045 mol), TEMPO (156 mg, 1 mmol) and Bu₄NI (1 g, 2.7 mmol) successively. The mixture was cooled to 0° C. and then aqueous NaClO (146 mL) was added dropwise. The resulting mixture was stirred for another two hours. The organic phase was separated and washed with water (100 mL), brine (100 mL) and dried over Na₂SO₄. The drying agent was removed by filtration and the residue was evaporated to give crude (3-bromo-phenyl)-(2,4-dichloro-pyrimidin-5-yl)-methanone as yellow solid. (Yield 30.2 g, 92%).

$^1$H NMR (300 MHz, CDCl₃): δ 8.63 (s, 1H), 7.96-7.95 (m, 1H), 7.84-7.80 (m, 1H), 7.70-7.56 (m, 1H), 7.42 (t, 1H, J=7.8 Hz).

Example 38

3-(3-Bromo-phenyl)-6-chloro-1H-pyrazolo[3,4-d] pyrimidine

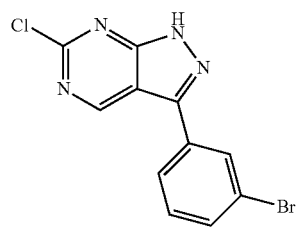 [SMILES: Clc1ncc2c(-c3cccc(Br)c3)n[nH]c2n1]

To a solution of crude (3-bromo-phenyl)-(2,4-dichloro-pyrimidin-5-yl)-methanone (from Example 37 supra) (1 g, 3.0 mmol) in THF (70 mL), 85% hydrazine (0.45 g, 7.64 mmol) was added dropwise at room temperature. The mixture was stirred for additional 20 minutes at room temperature and then heated at 50° C. for another 20 minutes. The solvent was removed under reduced pressure, and the residue was washed with water (5 mL), petroleum ether (10 mL) and dried to give 3-(3-bromo-phenyl)-6-chloro-1H-pyrazolo[3,4-d]pyrimidine as yellow solid. (Yield 0.848 g, 91.3%).

$^1$H NMR (300 MHz, DMSO): δ 14.55 (s, 1H), 9.63 (s, 1H), 8.25 (s, 1H), 8.20-8.10 (m, 1H), 7.77-7.69 (m, 1H), 7.52 (t, 1H, J=7.8 Hz). LC-MS: [M+H]$^+$ 308.9.

Example 39

{4-[3-(3-Bromo-phenyl)-1-(2-trimethylsilanyl-ethoxymethyl)-1H-pyrazolo[3,4-d]pyrimidin-6-ylamino]-cyclohexyl}-carbamic acid tert-butyl ester

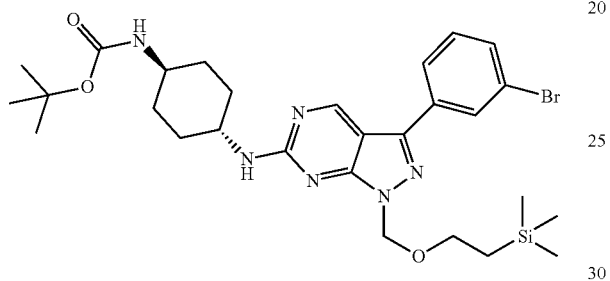

To a solution of 3-(3-bromo-phenyl)-6-chloro-1H-pyrazolo[3,4-d]pyrimidine (from Example 38 supra) (3.0 g, 9.7 mmol), Et$_3$N (5.4 mL, 38.8 mmol) in DMF (50 mL), (2-(chloromethoxy)-ethyl)trimethylsilane (SEM-Cl, 2.0 mL, 11.6 mmol) was added in one portion. The resultant mixture was stirred for 30 minutes at room temperature. To this solution, N-Boc-trans-1,4-cyclohexanediamine (2.48 g, 11.6 mmol) was added. The resulting mixture was stirred for one hour at room temperature. The reaction was then poured into water (200 mL) and extracted with EtOAc (3×200 mL). The EtOAc extract was dried over Na$_2$SO$_4$, filtered and concentrated. The crude product was purified by chromatography (silica gel, 200-300 mesh, EtOAc) to give {4-[3-(3-bromo-phenyl)-1-(2-trimethylsilanyl-ethoxymethyl)-1H-pyrazolo[3,4-d]pyrimidin-6-ylamino]-cyclohexyl}-carbamic acid tert-butyl ester as yellow oil. (Yield 2.2 g, 37.3%).

Example 40

[3-(3-Bromo-phenyl)-1-(2-trimethylsilanyl-ethoxymethyl)-1H-pyrazolo[3,4-d]pyrimidin-6-yl]-(2-morpholin-4-yl-ethyl)-amine

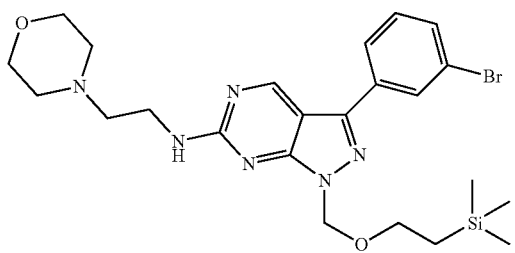 [SMILES: C[Si](C)(C)CCOCn1nc(-c2cccc(Br)c2)c2cnc(NCCN3CCOCC3)nc21]

To a solution of 3-(3-bromo-phenyl)-6-chloro-1H-pyrazolo[3,4-d]pyrimidine (from Example 38 supra) (3.0 g, 9.7 mmol), Et$_3$N (5.4 mL, 38.8 mmol) in DMF (50 mL), (2-(chloromethoxy)-ethyl)trimethylsilane (SEM-Cl, 2.0 mL, 11.6 mmol) was added in one portion. The resultant mixture was stirred for 30 minutes at room temperature. To this solution, 2-morpholino-ethanamine (1.51 g, 11.6 mmol) was added. The resulting mixture was stirred for one hour at room temperature. The reaction was poured into water (200 mL), extracted with EtOAc (3×200 mL), dried over Na$_2$SO$_4$, filtered and concentrated. The crude product was purified by chromatography (silica gel, 200-300 mesh, EtOAc) to give [3-(3-bromo-phenyl)-1-(2-trimethylsilanyl-ethoxymethyl)-1H-pyrazolo[3,4-d]pyrimidin-6-yl]-(2-morpholin-4-yl-ethyl)-amine as yellow oil. (Yield 1.7 g, 32.7%).

Example 41

[3-(6-Bromo-pyridin-2-yl)-1-(2-trimethylsilanyl-ethoxymethyl)-1H-pyrazolo[3,4-d]pyrimidin-6-yl]-(2-piperidin-1-yl-ethyl)-amine

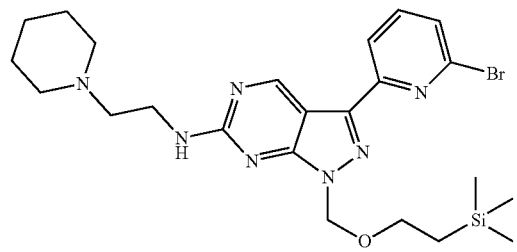 [SMILES: C[Si](C)(C)CCOCn1nc(-c2cccc(Br)n2)c2cnc(NCCN3CCCCC3)nc21]

A mixture of 3-(6-bromo-pyridin-2-yl)-6-chloro-1-(2-trimethylsilanyl-ethoxymethyl)-1H-pyrazolo[3,4-d]pyrimidine (from Example 31 supra) (1.0 g, 2.3 mmol), 2-(piperidin-1-yl)ethanamine (324 mg, 2.53 mmol) and TEA (256 mg, 2.53 mmol) in IPA (30 mL) was stirred at reflux for 16 hours. After cooling to room temperature, the solvent was removed under reduced pressure, and the residue was purified by column chromatography (a silica gel, MeOH:dichloromethane, 1:100) to give [3-(6-bromo-pyridin-2-yl)-1-(2-trimethylsilanyl-ethoxymethyl)-1H-pyrazolo[3,4-d]pyrimidin-6-yl]-(2-piperidin-1-yl-ethyl)-amine as a white solid. (Yield 285 mg, 23.3%).

LC-MS: [M+H]$^+$ 532.

Example 42

3-(3-Bromo-phenyl)-6-chloro-1-trityl-1H-pyrazolo[3,4-d]pyrimidine

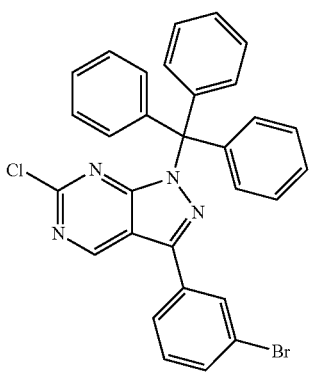 [SMILES: Clc1ncc2c(-c3cccc(Br)c3)nn(C(c3ccccc3)(c3ccccc3)c3ccccc3)c2n1]

To a mixture of 3-(3-bromo-phenyl)-6-chloro-1H-pyrazolo[3,4-d]pyrimidine (from Example 38 supra) (4.0 g, 12.9 mmol) and Et$_3$N (2.6 g, 25.8 mmol) in DMF (40 mL) was added the solution of trityl chloride (4.3 g, 15.5 mmol) in DMF (40 mL) at room temperature. This mixture was stirred at room temperature for 2 hours. The reaction solution was then poured into water (400 mL), and the yellow precipitate was collected by filtration. This crude product was purified by chromatography (silica gel, dichloromethane:petroleum ether, 1:1) to give 3-(3-bromo-phenyl)-6-chloro-1-trityl-1H-pyrazolo[3,4-d]pyrimidine as a light yellow solid. (Yield 3.5 g, 30%).

Example 43

{4-[3-(3-Bromo-phenyl)-1-trityl-1H-pyrazolo[3,4-d]pyrimidin-6-ylamino]-cyclohexyl}-carbamic acid tert-butyl ester

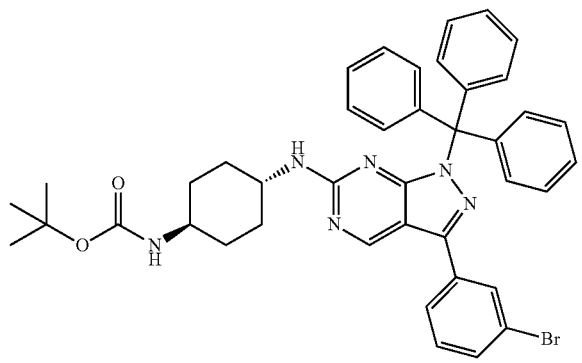 [SMILES: CC(C)(C)OC(=O)N[C@H]1CC[C@H](Nc2ncc3c(-c4cccc(Br)c4)nn(C(c4ccccc4)(c4ccccc4)c4ccccc4)c3n2)CC1]

To a solution of 3-(3-bromo-phenyl)-6-chloro-1-trityl-1H-pyrazolo[3,4-d]pyrimidine (from Example 42 supra) (1.10 g, 2.0 mmol) in DMF (20 mL) was add DIPEA (0.39 g, 2.8 mmol) and (4-amino-cyclohexyl)-carbamic acid tert-butyl ester (0.60 g, 2.8 mmol). This mixture was stirred at 120° C. for 12 hours. After cooling to room temperature, the reaction mixture was poured into water (100 mL) and the resulting precipitate was collected by filtration. The obtained yellow solid was purified by chromatography (silica gel, MeOH: dichloromethane, 1:100) to give a light solid which was washed with ether (4 mL) to give {4-[3-(3-bromo-phenyl)-1-trityl-1H-pyrazolo[3,4-d]pyrimidin-6-ylamino]-cyclohexyl}-carbamic acid tert-butyl ester as a white solid. (Yield 730 mg, 50.1%).

Example 44

[3-(6-Benzylamino-pyridin-2-yl)-1H-pyrazolo[3,4-d]pyrimidin-6-yl]-(2-piperidin-1-yl-ethyl)-amine

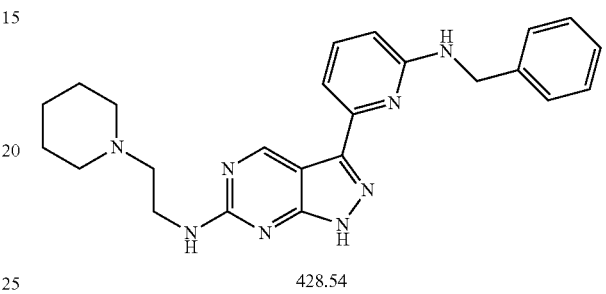

428.54

Step A

[3-(6-Benzylamino-pyridin-2-yl)-1-(2-trimethylsilanyl-ethoxymethyl)-1H-pyrazolo[3,4-d]pyrimidin-6-yl]-(2-piperidin-1-yl-ethyl)-amine

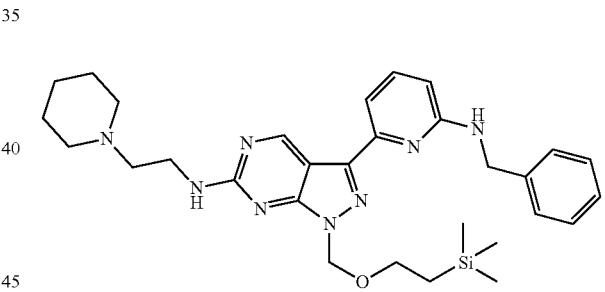

A sealed tube was charged with [3-(6-bromo-pyridin-2-yl)-1-(2-trimethylsilanyl-ethoxymethyl)-1H-pyrazolo[3,4-d]pyrimidin-6-yl]-(2-piperidin-1-yl-ethyl)-amine (from Example 41 supra) (285 mg, 0.54 mmol), benzylamine (69 mg, 0.65 mmol), Pd$_2$(dba)$_3$ (20 mg), DavePhos (30 mg), tBuONa (61 mg, 0.65 mmol) and dioxane (10 mL). This mixture was stirred at 105° C. under an atmosphere of N$_2$ for 16 hours. After cooling to room temperature, the solvent was removed under reduced pressure. The residue was partitioned between water and dichloromethane. The water layer was extracted with dichloromethane twice. The combined organics was dried over anhydrous MgSO$_4$, filtered and concentrated under reduced pressure. The residue was purified by a column chromatography (silica gel, 8 g, 200-300 mesh, eluting with MeOH:dichloromethane, 1:100 to 1:50 to give [3-(6-benzylamino-pyridin-2-yl)-1-(2-trimethylsilanyl-ethoxymethyl)-1H-pyrazolo[3,4-d]pyrimidin-6-yl]-(2-piperidin-1-yl-ethyl)-amine as a light-yellow oil. (Yield 131 mg, 43.4%)

LC-MS: [M+H]$^+$ 559. .

Step B

[3-(6-Benzylamino-pyridin-2-yl)-1H-pyrazolo[3,4-d]
pyrimidin-6-yl]-(2-piperidin-1-yl-ethyl)-amine

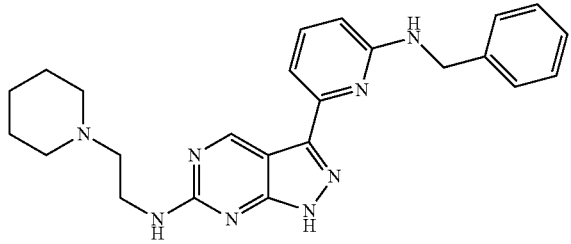 [SMILES: c1ccc(CNc2cccc(-c3n[nH]c4nc(NCCN5CCCCC5)ncc34)n2)cc1]

To a mixture of [3-(6-benzylamino-pyridin-2-yl)-1-(2-trimethylsilanyl-ethoxymethyl)-1H-pyrazolo[3,4-d]pyrimidin-6-yl]-(2-piperidin-1-yl-ethyl)-amine (133 mg, 0.24 mmol) in dichloromethane (2 mL) was added CF$_3$CO$_2$H (3 mL). This mixture was stirred at room temperature for 3 hours. The reaction was quenched by adding saturated aqueous NaHCO$_3$ to pH about 9, and then extracted with dichloromethane (3×20 mL). The combined organic phase was dried over anhydrous MgSO$_4$, filtered and concentrated under reduced pressure. The residue was washed with EtOAc (4 mL) and dried to give [3-(6-benzylamino-pyridin-2-yl)-1H-pyrazolo[3,4-d]pyrimidin-6-yl]-(2-piperidin-1-yl-ethyl)-amine as a white solid. (Yield 78 mg, 76%).

$^1$H NMR (300 MHz, DMSO): δ 9.21 (brs, 1H), 7.54-7.19 (m, 9H), 6.71 (t, 1H, J=6.6 Hz), 6.57 (d, 1H, J=5.4 Hz), 5.54 (d, 2H, J=6.6 Hz), 4.60 (d, 2H, J=6.0 Hz), 3.53 (brs, 2H), 2.53 (brs, 4H), 1.56-1.42 (m, 6H). LC-MS: [M+H]$^+$ 429; [M−H]$^+$ 427.

Example 45

[3-(6-Benzylamino-pyridin-2-yl)-1H-pyrazolo[3,4-d]
pyrimidin-6-yl]-(2-morpholin-4-yl-ethyl)-amine

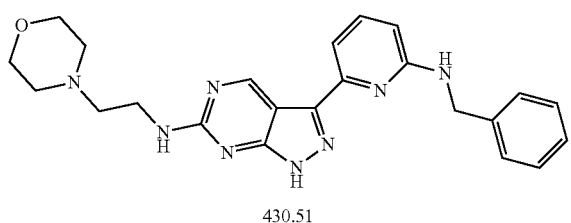 [SMILES: c1ccc(CNc2cccc(-c3n[nH]c4nc(NCCN5CCOCC5)ncc34)n2)cc1]

430.51

Step A

[3-(6-Benzylamino-pyridin-2-yl)-1-(2-trimethylsilanyl-ethoxymethyl)-1H-pyrazolo[3,4-d]pyrimidin-6-yl]-(2-morpholin-4-yl-ethyl)-amine

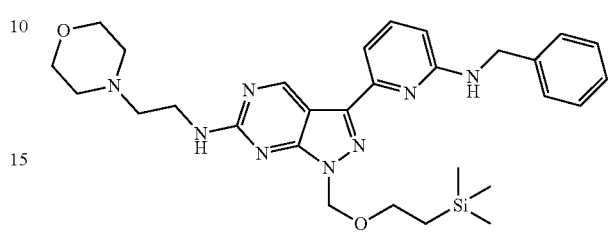

A sealed tube was charged with [3-(6-bromo-pyridin-2-yl)-1-(2-trimethylsilanyl-ethoxymethyl)-1H-pyrazolo[3,4-d]pyrimidin-6-yl]-(2-morpholin-4-yl-ethyl)-amine (from Example 32 supra) (150 mg, 0.28 mmol), benzylamine (42 mg, 0.39 mmol), Pd$_2$(dba)$_3$ (16 mg, 10% mmol), DavePhos (22 mg, 20% mmol), t-BuONa (37 mg, 0.39 mmol) and dioxane (10 mL). The mixture was stirred at 130° C. under an atmosphere of N$_2$ for 6 hours. After cooling to room temperature, the mixture was filtered and concentrated under reduced pressure. The residue was purified by column chromatography (silica gel, dichloromethane: MeOH, 100:1) to give [3-(6-benzylamino-pyridin-2-yl)-1-(2-trimethylsilanyl-ethoxymethyl)-1H-pyrazolo[3,4-d]pyrimidin-6-yl]-(2-morpholin-4-yl-ethyl)-amine. (Yield 90 mg, 57%).

Step B

[3-(6-Benzylamino-pyridin-2-yl)-1H-pyrazolo[3,4-d]
pyrimidin-6-yl]-(2-morpholin-4-yl-ethyl)-amine To a solution of [3-(6-benzylamino-pyridin-2-yl)-1-(2-trimethylsilanyl-ethoxymethyl)-1H-pyrazolo[3,4-d]pyrimidin-6-yl]-(2-morpholin-4-yl-ethyl)-amine (95 mg, 0.17 mmol) in dichloromethane (2 mL) was added TFA (2 mL). The reaction mixture was stirred for 2 hours at room temperature. The mixture was adjusted to about pH 8 with saturated NaHCO$_3$ solution. The resulting mixture was extracted with dichloromethane. The organic layer was dried and concentrated under reduced pressure. The residue was purified by prep-HPLC to give [3-(6-benzylamino-pyridin-2-yl)-1H-pyrazolo[3,4-d]pyrimidin-6-yl]-(2-morpholin-4-yl-ethyl)-amine. (Yield 18 mg, 25%).

$^1$H NMR (300 MHz, DMSO): δ 10.95 (brs, 1H), 9.45 (s, 1H), 7.55-7.27 (m, 7H), 6.44 (d, 1H, J=8.1 Hz), 6.00 (brs, 1H), 4.92 (brs, 1H), 4.67 (d, 2H, J=5.7 Hz), 3.74 (t, 4H, J=4.8 Hz), 3.64-3.59 (m, 2H), 2.68 (t, 2H, J=6.0 Hz), 2.55-2.53 (m, 5H). LC-MS: [M+H]+ 431.2.

Example 46

[3-(3-Benzylamino-phenyl)-1H-pyrazolo[3,4-d]pyrimidin-6-yl]-(2-morpholin-4-yl-ethyl)-amine

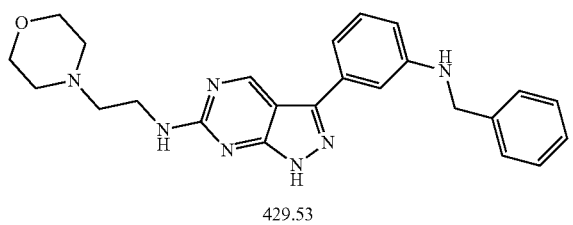 [SMILES: c1ccc(CNc2cccc(-c3n[nH]c4nc(NCCN5CCOCC5)ncc34)c2)cc1]

429.53

Step A

[3-(3-Benzylamino-phenyl)-1-(2-trimethylsilanyl-ethoxymethyl)-1H-pyrazolo[3,4-d]pyrimidin-6-yl]-(2-morpholin-4-yl-ethyl)-amine

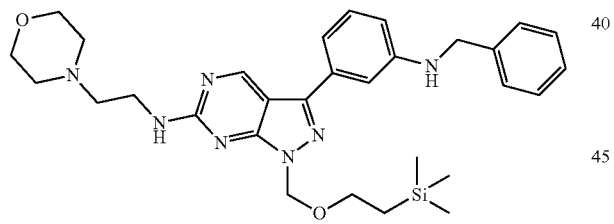

To a stirred solution of [3-(3-bromo-phenyl)-1-(2-trimethylsilanyl-ethoxymethyl)-1H-pyrazolo[3,4-d]pyrimidin-6-yl]-(2-morpholin-4-yl-ethyl)-amine (from Example 40 supra) (250 mg, 0.46 mmol), benzylamine (75 mg, 0.70 mmol), DavePhos (30 mg, 0.076 mmol) and t-BuONa (70 mg, 0.73 mmol) in 1,4-dioxane (10 mL), Pd$_2$(dba)$_3$ (42 mg, 0.073 mmol) was added in one portion under N$_2$ atmosphere. The resultant mixture was stirred at 100° C. for 16 hours. The mixture was cooled and filtered; the filtrate was evaporated under reduced pressure to give the crude product. It was purified by chromatography (silica gel, 200-300 mesh, dichloromethane:MeOH, 100:1, v/v) to give a mixture of [3-(3-benzylamino-phenyl)-1-(2-trimethylsilanyl-ethoxymethyl)-1H-pyrazolo[3,4-d]pyrimidin-6-yl]-(2-morpholin-4-yl-ethyl)-amine and (2-morpholin-4-yl-ethyl)-[3-phenyl-1-(2-trimethylsilanyl-ethoxymethyl)-1H-pyrazolo[3,4-d]pyrimidin-6-yl]-amine. (Yield 210 mg).

LC-MS: [M+H]+ 560.3.

Step B

[3-(3-Benzylamino-phenyl)-1H-pyrazolo[3,4-d]pyrimidin-6-yl]-(2-morpholin-4-yl-ethyl)-amine

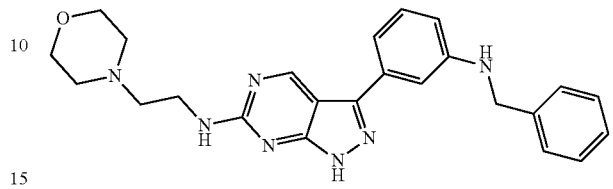

To a stirred solution of a mixture of [3-(3-benzylamino-phenyl)-1-(2-trimethylsilanyl-ethoxymethyl)-1H-pyrazolo[3,4-d]pyrimidin-6-yl]-(2-morpholin-4-yl-ethyl)-amine and (2-morpholin-4-yl-ethyl)-[3-phenyl-1-(2-trimethylsilanyl-ethoxymethyl)-1H-pyrazolo[3,4-d]pyrimidin-6-yl]-amine (210 mg, crude) in dichloromethane (5 mL) was added TFA (5 mL) at room temperature. The resulting mixture was stirred for another three hours at this temperature. The solvent was evaporated under reduced pressure and the residue was treated with saturated aqueous NaHCO$_3$ (3 mL) and extracted with EtOAc (10 mL). The organic phase was washed with brine (5 mL) and dried to give crude product. It was purified by prep-HPLC to give [3-(3-benzylamino-phenyl)-1H-pyrazolo[3,4-d]pyrimidin-6-yl]-(2-morpholin-4-yl-ethyl)-amine as yellow solid. (Yield 24 mg, 14.9%).

$^1$H NMR (300 MHz, CD$_3$OD): δ 8.93 (s, 1H), 7.46-7.30 (m, 8H), 6.98-6.95 (m, 1H), 4.50 (s, 2H), 3.93-3.48 (m, 12H). LC-MS: [M+H]+ 430.

Example 47

{3-[6-(3-Chloro-benzylamino)-pyridin-2-yl]-1H-pyrazolo[3,4-d]pyrimidin-6-yl}-(2-morpholin-4-yl-ethyl)-amine

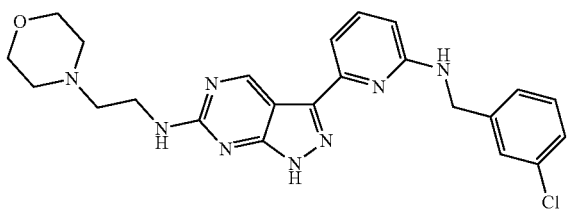

464.96

Step A

[3-[6-(3-Chloro-benzylamino)-pyridin-2-yl]-1-(2-trimethylsilanyl-ethoxymethyl)-1H-pyrazolo[3,4-d]pyrimidin-6-yl]-(2-morpholin-4-yl-ethyl)-amine

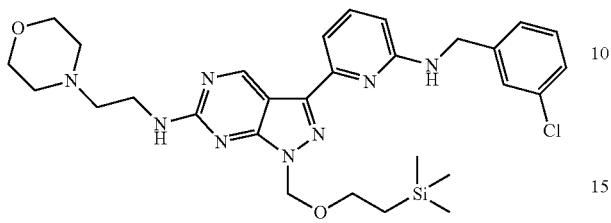

A sealed tube was charged with [3-(6-bromo-pyridin-2-yl)-1-(2-trimethylsilanyl-ethoxymethyl)-1H-pyrazolo[3,4-d]pyrimidin-6-yl]-(2-morpholin-4-yl-ethyl)-amine (from Example 32 supra) (200 mg, 0.37 mmol), 3-chlorobenzylamine (74 mg, 0.52 mmol), Pd$_2$(dba)$_3$ (21 mg, 10% mmol), DavePhos (29 mg, 20% mmol), t-BuONa (50 mg, 0.52 mmol) and dioxane (10 mL). The mixture was stirred at 120° C. under an atmosphere of N$_2$ for 6 hours. After cooling to room temperature, the mixture was filtered and concentrated under reduced pressure. The residue was purified by column chromatography (silica gel, dichloromethane:MeOH, 100:1) to give [3-[6-(3-chloro-benzylamino)-pyridin-2-yl]-1-(2-trimethylsilanyl-ethoxymethyl)-1H-pyrazolo[3,4-d]pyrimidin-6-yl]-(2-morpholin-4-yl-ethyl)-amine. (Yield 110 mg, 50%).

Step B

{3-[6-(3-Chloro-benzylamino)-pyridin-2-yl]-1H-pyrazolo[3,4-d]pyrimidin-6-yl}-(2-morpholin-4-yl-ethyl)-amine

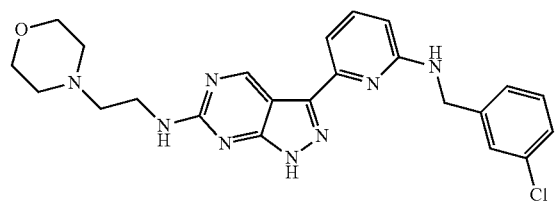 [SMILES: Clc1cccc(CNc2cccc(-c3n[nH]c4nc(NCCN5CCOCC5)ncc34)n2)c1]

To a solution of [3-[6-(3-chloro-benzylamino)-pyridin-2-yl]-1-(2-trimethylsilanyl-ethoxymethyl)-1H-pyrazolo[3,4-d]pyrimidin-6-yl]-(2-morpholin-4-yl-ethyl)-amine (110 mg, 0.185 mmol) in dichloromethane (2.5 mL) was added TFA (2.5 mL). The reaction mixture was stirred for 2 hours at room temperature. The pH of the mixture was adjusted to about 8 with saturated NaHCO$_3$ solution. The resulting mixture was extracted with ethyl acetate. The organic layer was dried and concentrated under reduced pressure. The residue was purified by column chromatography (silica gel, dichloromethane:MeOH, 20:1), then further purified by prep-HPLC to give {3-[6-(3-chloro-benzylamino)-pyridin-2-yl]-1H-pyrazolo[3,4-d]pyrimidin-6-yl}-(2-morpholin-4-yl-ethyl)-amine. (Yield 23 mg, 26%).

$^1$H NMR (300 MHz, CD$_3$OD): δ 9.19 (s, 1H), 7.54-7.24 (m, 6H), 6.58 (d, 1H, J=8.1 Hz), 4.69 (s, 2H), 3.74-3.71 (m, 4H), 3.61 (t, 2H, J=6.6 Hz), 2.68-2.56 (m, 7H). LC-MS: [M+H]$^+$ 465.

Example 48

{3-[6-(4-Chloro-benzylamino)-pyridin-2-yl]-1H-pyrazolo[3,4-d]pyrimidin-6-yl}-(2-morpholin-4-yl-ethyl)-amine

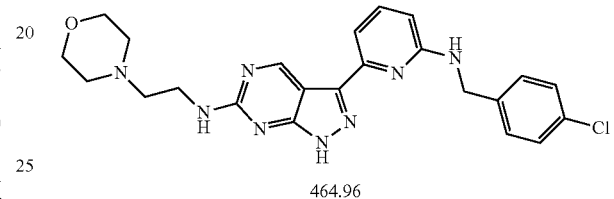

464.96

Step A

[3-[6-(4-Chloro-benzylamino)-pyridin-2-yl]-1-(2-trimethylsilanyl-ethoxymethyl)-1H-pyrazolo[3,4-d]pyrimidin-6-yl]-(2-morpholin-4-yl-ethyl)-amine

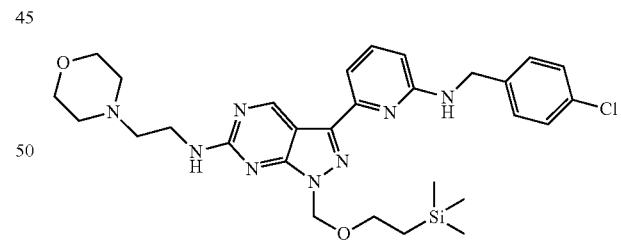

A sealed tube was charged with [3-(6-bromo-pyridin-2-yl)-1-(2-trimethylsilanyl-ethoxymethyl)-1H-pyrazolo[3,4-d]pyrimidin-6-yl]-(2-morpholin-4-yl-ethyl)-amine (from Example 32 supra) (200 mg, 0.37 mmol), 4-chlorobenzylamine (74 mg, 0.52 mmol), Pd$_2$(dba)$_3$ (21 mg, 10% mmol), DavePhos (29 mg, 20% mmol), t-BuONa (50 mg, 0.52 mmol) and dioxane (10 mL). The mixture was stirred at 130° C. under an atmosphere of N$_2$ for 6 hours. After cooling to room temperature, the mixture was filtered and concentrated under reduced pressure. The residue was purified by column chromatography (silica gel, dichloromethane:MeOH, 100:1) to give [3-[6-(4-chloro-benzylamino)-pyridin-2-yl]-1-(2-trimethylsilanyl-ethoxymethyl)-1H-pyrazolo[3,4-d]pyrimidin-6-yl]-(2-morpholin-4-yl-ethyl)-amine. (Yield 100 mg, 50%).

Step B

{3-[6-(4-Chloro-benzylamino)-pyridin-2-yl]-1H-pyrazolo[3,4-d]pyrimidin-6-yl}-(2-morpholin-4-yl-ethyl)-amine

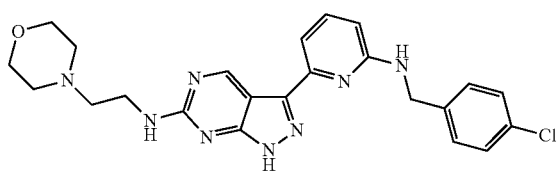 [SMILES: Clc1ccc(CNc2cccc(-c3n[nH]c4nc(NCCN5CCOCC5)ncc34)n2)cc1]

To a solution of [3-[6-(4-chloro-benzylamino)-pyridin-2-yl]-1-(2-trimethylsilanyl-ethoxymethyl)-1H-pyrazolo[3,4-d]pyrimidin-6-yl]-(2-morpholin-4-yl-ethyl)-amine (100 mg, 0.168 mmol) in dichloromethane (2 mL) was added TFA (2 mL). The reaction mixture was stirred for 2 hours at room temperature. The pH of mixture was then adjusted to about 8 with saturated NaHCO₃ solution. The resulting mixture was extracted with dichloromethane. The organic layer was dried and concentrated under reduced pressure. The residue was purified by prep-HPLC to give {3-[6-(4-Chloro-benzylamino)-pyridin-2-yl]-1H-pyrazolo[3,4-d]pyrimidin-6-yl}-(2-morpholin-4-yl-ethyl)-amine. (Yield 20 mg, 26%).

$^1$H NMR (300 MHz, CD$_3$OD): δ 9.23 (s, 1H), 7.56-7.34 (m, 6H), 6.60 (d, 1H, J=8.1 Hz), 4.72 (s, 2H), 3.81-3.67 (m, 6H), 2.85-2.79 (m, 6H). LC-MS: [M+H]$^+$ 465; [M−H]$^+$ 463.

Example 49

N-[3-(6-Benzylamino-pyridin-2-yl)-1H-pyrazolo[3,4-d]pyrimidin-6-yl]-cyclohexane-1,4-diamine

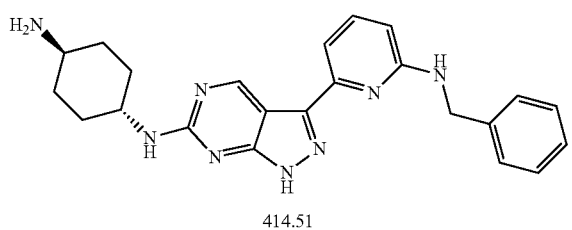 [SMILES: N[C@H]1CC[C@H](Nc2ncc3c(-c4cccc(NCc5ccccc5)n4)n[nH]c3n2)CC1]

414.51

Step A

4-[3-(6-Benzylamino-pyridin-2-yl)-1-(2-trimethylsilanyl-ethoxymethyl)-1H-pyrazolo[3,4-d]pyrimidin-6-ylamino]-cyclohexyl}-carbamic acid tert-butyl ester

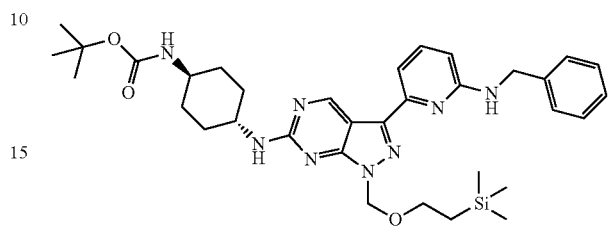

A sealed tube was charged with {4-[3-(6-bromo-pyridin-2-yl)-1-(2-trimethylsilanyl-ethoxymethyl)-1H-pyrazolo[3,4-d]pyrimidin-6-ylamino]-cyclohexyl}-carbamic acid tert-butyl ester (from Example 33 supra) (300 mg, 0.485 mmol), benzylamine (70 mg, 0.654 mmol), Pd$_2$(dba)$_3$ (29 mg, 0.05 mmol), DavePhos (38 mg, 0.096 mmol), t-BuONa (66 mg, 0.687 mmol) and dioxane (14 mL). The mixture was stirred at 102° C. under an atmosphere of N$_2$ for 14 hours. After cooling to room temperature, the mixture was filtered and concentrated under reduced pressure. The residue was purified by column chromatography (silica gel, 13 g, 200-300 mesh, eluting with dichloromethane:MeOH, 100:1) to give 4-[3-(6-benzylamino-pyridin-2-yl)-1-(2-trimethylsilanyl-ethoxymethyl)-1H-pyrazolo[3,4-d]pyrimidin-6-ylamino]-cyclohexyl}-carbamic acid tert-butyl ester. (Yield 169 mg, 54%). LC-MS: [M+H]$^+$ 645.

Step B

N-[3-(6-Benzylamino-pyridin-2-yl)-1H-pyrazolo[3,4-d]pyrimidin-6-yl]-cyclohexane-1,4-diamine

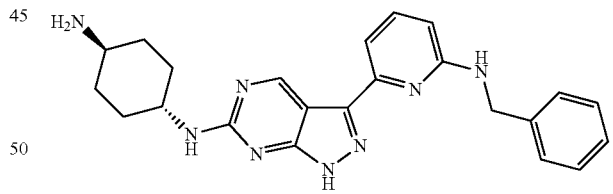

To a mixture of 4-[3-(6-benzylamino-pyridin-2-yl)-1-(2-trimethylsilanyl-ethoxymethyl)-1H-pyrazolo[3,4-d]pyrimidin-6-ylamino]-cyclohexyl}-carbamic acid tert-butyl ester (169 mg, 0.262 mmol) in dichloromethane (2 mL) was added CF$_3$COOH (2 mL). This mixture was stirred at room temperature for 1 hour. The solvent was then removed under reduced pressure. A saturated aqueous solution of NaHCO$_3$ was added to the residue, and then extracted with ethyl acetate (3×15 mL). The combined organic phase was dried over anhydrous Na$_2$SO$_4$, filtered and concentrated under reduced pressure. The residue was purified by prep-HPLC to give N-[3-(6-benzylamino-pyridin-2-yl)-1H-pyrazolo[3,4-d]pyrimidin-6-yl]-cyclohexane-1,4-diamine as a yellow solid. (Yield 66 mg, 61%).

¹H NMR (300 MHz, DMSO): δ 9.12 (s, 1H), 7.50-7.20 (m, 9H), 6.53 (d, 1H, J=8.1 Hz), 4.60 (d, 2H, J=5.4 Hz), 3.65-3.33 (m, 5H), 1.98-1.82 (m, 4H), 1.30-1.12 (m, 4H). LC-MS: [M+H]⁺ 415.

Example 50

{3-[3-(4-Chloro-benzylamino)-phenyl]-1H-pyrazolo[3,4-d]pyrimidin-6-yl}-(2-morpholin-4-yl-ethyl)-amine

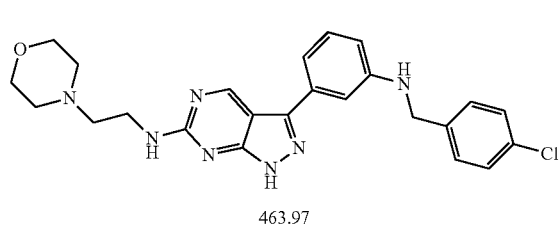 [SMILES: Clc1ccc(CNc2cccc(-c3n[nH]c4nc(NCCN5CCOCC5)ncc34)c2)cc1]

463.97

Step A

3-[3-(4-Chloro-benzylamino)-phenyl]-1-(2-trimethylsilanyl-ethoxymethyl)-1H-pyrazolo[3,4-d]pyrimidin-6-yl]-(2-morpholin-4-yl-ethyl)-amine

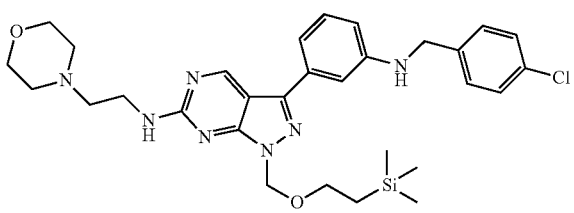

To a stirred solution of [3-(3-bromo-phenyl)-1-(2-trimethylsilanyl-ethoxymethyl)-1H-pyrazolo-[3,4-d]pyrimidin-6-yl]-(2-morpholin-4-yl-ethyl)-amine (from Example 40 supra) (250 mg, 0.468 mmol), 4-chlorobenzylamine (80 mg, 0.564 mmol), DavePhos (37 mg) and t-BuONa (54 mg, 0.564 mmol) in 1,4-dioxane (10 mL), Pd₂(dba)₃ (42 mg, 0.073 mmol) was added in one portion under N₂ atmosphere. The resultant mixture was stirred at 100° C. for 6 hours. The mixture was cooled and filtered; the filtrate was evaporated under reduced pressure to give the crude product. It was purified by chromatography (silica gel, 200-300 mesh, dichloromethane:MeOH, 100:1, v/v) to give 3-[3-(4-chloro-benzylamino)-phenyl]-1-(2-trimethylsilanyl-ethoxym-ethyl)-1H-pyrazolo[3,4-d]pyrimidin-6-yl]-(2-morpholin-4-yl-ethyl)-amine. (Yield 140 mg, 50%).

LC-MS: [M+H]⁺ 594.

Step B

{3-[3-(4-Chloro-benzylamino)-phenyl]-1H-pyrazolo[3,4-d]pyrimidin-6-yl}-(2-morpholin-4-yl-ethyl)-amine

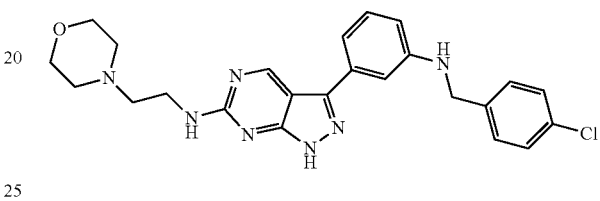

To a stirred solution of 3-[3-(4-chloro-benzylamino)-phenyl]-1-(2-trimethylsilanyl-ethoxymethyl)-1H-pyrazolo[3,4-d]pyrimidin-6-yl]-(2-morpholin-4-yl-ethyl)-amine (140 mg, 0.236 mmol) in dichloromethane (3 mL) was added TFA (3 mL) at room temperature. The resulting mixture was stirred for another three hours at this temperature. The solvent was evaporated under reduced pressure and the pH of the residue was adjusted to 8 with saturated NaHCO₃. The resulting mixture was extracted with EtOAc (10 mL). The organic layer was dried and concentrated. It was purified by prep-HPLC to give {3-[3-(4-chloro-benzylamino)-phenyl]-1H-pyrazolo[3,4-d]pyrimidin-6-yl}-(2-morpholin-4-yl-ethyl)-amine. (Yield 65 mg, 60%).

¹H NMR (300 MHz, CD₃OD): δ 8.87 (s, 1H), 7.43-7.11 (m, 7H), 6.73 (d, 1H, J=7.2 Hz), 4.41 (s, 2H), 3.88-3.79 (m, 6H), 3.24 (brs, 6H). LC-MS: [M+H]⁺ 464.

Example 51

(2-Morpholin-4-yl-ethyl)-(3-{3-[(thiophen-3-ylm-ethyl)-amino]-phenyl}-1H-pyrazolo[3,4-d]pyrimidin-6-yl)-amine

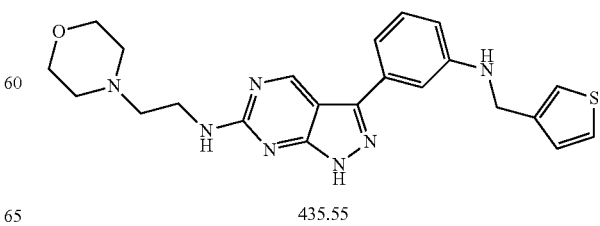

435.55

Step A (2-Morpholin-4-yl-ethyl)-[3-{3-[(thiophen-3-ylmethyl)-amino]-phenyl}-1-(2-trimethylsilanyl-ethoxymethyl)-1H-pyrazolo[3,4-d]pyrimidin-6-yl]-amine

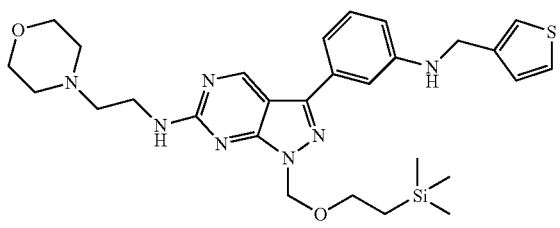 [SMILES: C[Si](C)(C)CCOCn1nc(-c2cccc(NCc3ccsc3)c2)c2cnc(NCCN3CCOCC3)nc21]

To a stirred solution of [3-(3-bromo-phenyl)-1-(2-trimethylsilanyl-ethoxymethyl)-1H-pyrazolo[3,4-d]pyrimidin-6-yl]-(2-morpholin-4-yl-ethyl)-amine (from Example 40 supra) (250 mg, 0.47 mmol), thiophen-3-yl-methylamine (54 mg, 0.564 mmol), DavePhos (37 mg, 20% mol) and t-BuONa (54 mg, 0.564 mmol) in 1,4-dioxane (10 mL), Pd$_2$(dba)$_3$ (27 mg, 10% mol) was added in one portion under N$_2$ atmosphere. The resultant mixture was stirred at 100° C. for 6 hours. The mixture was cooled and filtered; the filtrate was evaporated under reduced pressure to give the crude product. It was purified by chromatography (silica gel, 200-300 mesh, dichloromethane:MeOH, 100:1, v/v) to give (2-morpholin-4-yl-ethyl)-[3-{3-[(thiophen-3-ylmethyl)-amino]-phenyl}-1-(2-trimethylsilanyl-ethoxymethyl)-1H-pyrazolo[3,4-d]pyrimidin-6-yl]-amine. (Yield 150 mg, 56%).

LC-MS: [M+H]$^+$ 566.

Step B (2-Morpholin-4-yl-ethyl)-(3-{3-[(thiophen-3-ylmethyl)-amino]-phenyl}-1H-pyrazolo[3,4-d]pyrimidin-6-yl)-amine

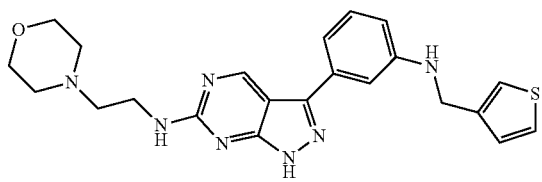 [SMILES: c1cc(NCc2ccsc2)cc(-c2n[nH]c3nc(NCCN4CCOCC4)ncc23)c1]

To the stirred solution of (2-morpholin-4-yl-ethyl)-[3-{3-[(thiophen-3-ylmethyl)-amino]-phenyl}-1-(2-trimethylsilanyl-ethoxymethyl)-1H-pyrazolo[3,4-d]pyrimidin-6-yl]-amine (150 mg, 0.265 mmol) in dichloromethane (3 mL) was added TFA (3 mL) at room temperature. The resulting mixture was stirred for another two hours at this temperature. The solvent was then evaporated under reduced pressure and the pH of the residue was adjusted to 8 with saturated NaHCO$_3$. The resulting mixture was extracted with EtOAc (10 mL). The organic layer was dried and concentrated. It was purified by prep-HPLC to give (2-morpholin-4-yl-ethyl)-(3-{3-[(thiophen-3-ylmethyl)-amino]-phenyl}-1H-pyrazolo[3,4-d]pyrimidin-6-yl)-amine. (Yield 70 mg, 61%).

$^1$H NMR (300 MHz, CD$_3$OD): δ 8.89 (s, 1H), 7.39-7.13 (m, 6H), 6.78 (d, 1H, J=8.1 Hz), 4.41 (s, 2H), 3.92-3.84 (m, 6H), 3.38 (brs, 6H). LC-MS: [M+H]$^+$ 436.

Example 52

N-[3-(3-Benzylamino-phenyl)-1H-pyrazolo[3,4-d]pyrimidin-6-yl]-cyclohexane-1,4-diamine

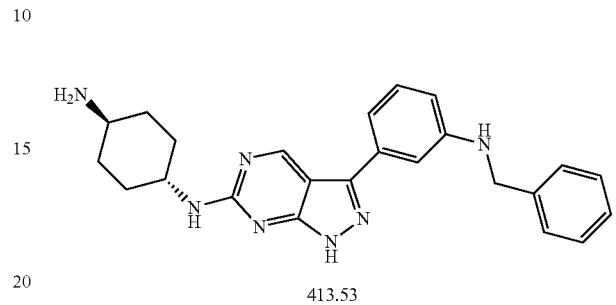

413.53

Step A

{4-[3-(3-Benzylamino-phenyl)-1-(2-trimethylsilanyl-ethoxymethyl)-1H-pyrazolo[3,4-d]pyrimidin-6-ylamino]-cyclohexyl}-carbamic acid tert-butyl ester

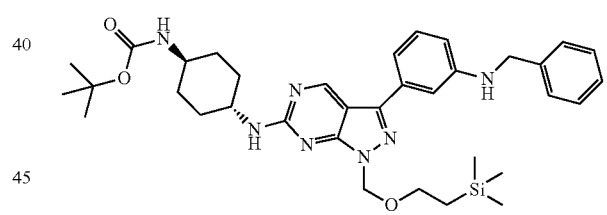

To a stirred solution of {4-[3-(3-bromo-phenyl)-1-(2-trimethylsilanyl-ethoxymethyl)-1H-pyrazolo[3,4-d]pyrimidin-6-ylamino]-cyclohexyl}-carbamic acid tert-butyl ester (from Example 39 supra) (300 mg, 0.48 mmol), benzylamine (80 mg, 0.74 mmol), DavePhos (20 mg, 0.05 mmol) and t-BuONa (56 mg, 0.58 mmol) in 1,4-dioxane (10 mL), Pd$_2$(dba)$_3$ (28 mg, 0.48 mmol) was added in one portion under N$_2$ atmosphere. The resultant mixture was stirred at 100° C. for 4 hours. The mixture was cooled and filtered. The filtrate was evaporated under reduced pressure to give the crude product. It was purified by chromatography (silica gel, 200-300 mesh, dichloromethane:MeOH, 100:1, v/v) to give a mixture of {4-[3-(3-benzylamino-phenyl)-1-(2-trimethylsilanyl-ethoxymethyl)-1H-pyrazolo[3,4-d]pyrimidin-6-ylamino]-cyclohexyl}-carbamic acid tert-butyl ester (300 mg, as a mixture with {-4-[3-phenyl-1-(2-trimethylsilanyl-ethoxymethyl)-1H-pyrazolo[3,4-d]pyrimidin-6-ylamino]-cyclohexyl}-carbamic acid tert-butyl ester)

LC-MS: [M+H]$^+$ 644.4. .

Step B

N-[3-(3-Benzylamino-phenyl)-1H-pyrazolo[3,4-d]pyrimidin-6-yl]-cyclohexane-1,4-diamine

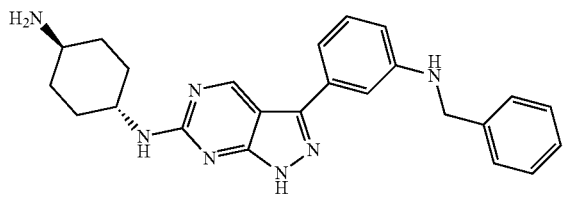 [SMILES: N[C@H]1CC[C@H](Nc2ncc3c(-c4cccc(NCc5ccccc5)c4)n[nH]c3n2)CC1]

To a stirred solution of {4-[3-phenyl-1-(2-trimethylsilanyl-ethoxymethyl)-1H-pyrazolo[3,4-d]pyrimidin-6-ylamino]-cyclohexyl}-carbamic acid tert-butyl ester) (300 mg, crude) in dichloromethane (10 mL) was added TFA (15 mL) at room temperature. The resulting mixture was stirred for another four hours at this temperature. The solvent was evaporated under reduced pressure and the residue was treated with saturated aqueous NaHCO$_3$ (5 mL) and extracted with EtOAc (2×10 mL). The organic phase was washed with brine (5 mL) and dried to give crude product. It was purified by chromatography (silica gel, 200-300 mesh, MeOH:DMC, 1:20, v/v) to give N-[3-(3-benzylamino-phenyl)-1H-pyrazolo[3,4-d]pyrimidin-6-yl]-cyclohexane-1,4-diamine as solid. (Yield 23 mg, 11.6%).

$^1$H NMR (300 MHz, CD$_3$OD): δ 8.72 (s, 1H), 7.44-7.10 (m, 8H), 6.73 (d, 1H, J=7.8 Hz), 4.41 (s, 2H), 3.85 (brs, 1H), 2.79 (brs, 1H), 2.21-1.96 (m, 4H), 1.40-1.30 (m, 4H). LC-MS: [M+H]$^+$ 414.

Example 53

N-(3-{3-[(Thiophen-2-ylmethyl)-amino]-phenyl}-1H-pyrazolo[3,4-d]pyrimidin-6-yl)-cyclohexane-1,4-diamine

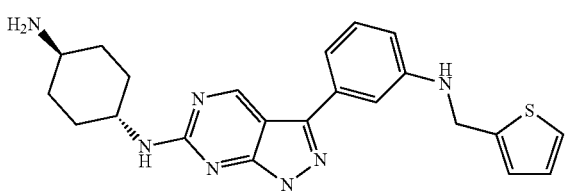

419.55

Step A

{4-[3-{3-[(Thiophen-2-ylmethyl)-amino]-phenyl}-1-(2-trimethylsilanyl-ethoxymethyl)-1H-pyrazolo[3,4-d]pyrimidin-6-ylamino]-cyclohexyl}-carbamic acid tert-butyl ester

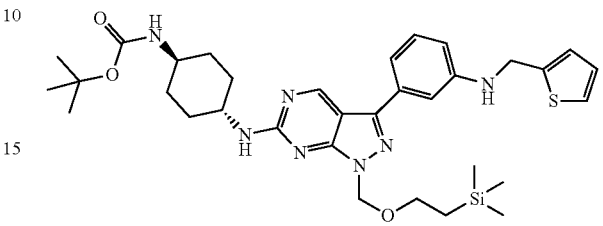

To a stirred solution of {4-[3-(3-bromo-phenyl)-1-(2-trimethylsilanyl-ethoxymethyl)-1H-pyrazolo[3,4-d]pyrimidin-6-ylamino]-cyclohexyl}-carbamic acid tert-butyl ester (from Example 39 supra) (300 mg, 0.48 mmol), thiophen-2-ylmethylamine (120 mg, 1.06 mmol), DavePhos (20 mg, 0.048 mmol) and t-BuONa (56 mg, 0.58 mmol) in 1,4-dioxane (10 mL), Pd$_2$(dba)$_3$ (28 mg, 0.48 mmol) was added in one portion under N$_2$ atmosphere. The resultant mixture was stirred at 100° C. for 4 hours. The mixture was cooled and filtered; the filtrate was evaporated under reduced pressure to give the crude product. It was purified by chromatography (silica gel, 200-300 mesh, dichloromethane:MeOH, 100:1, v/v) to give {4-[3-{3-[(thiophen-2-ylmethyl)-amino]-phenyl}-1-(2-trimethylsilanyl-ethoxymethyl)-1H-pyrazolo[3,4-d]pyrimidin-6-ylamino]-cyclohexyl}-carbamic acid tert-butyl ester. (Yield 290 mg, 92.9%).

LC-MS: [M+H]$^+$ 650.3.

Step B

N-(3-{3-[(Thiophen-2-ylmethyl)-amino]-phenyl}-1H-pyrazolo[3,4-d]pyrimidin-6-yl)-cyclohexane-1,4-diamine

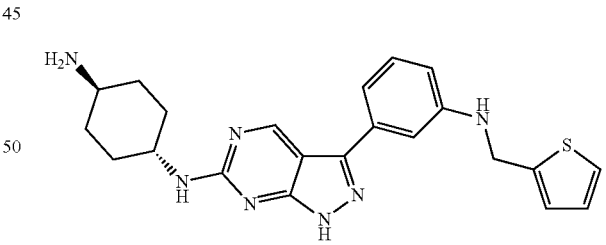

To a stirred solution of {4-[3-{3-[(thiophen-2-ylmethyl)-amino]-phenyl}-1-(2-trimethylsilanyl-ethoxymethyl)-1H-pyrazolo[3,4-d]pyrimidin-6-ylamino]-cyclohexyl}-carbamic acid tert-butyl ester (290 mg, 0.44 mmol) in dichloromethane (10 mL) was added TFA (15 mL) at room temperature. The resulting mixture was stirred for another four hours at this temperature. The solvent was evaporated under reduced pressure and the residue was treated with saturated aqueous NaHCO$_3$ (5 mL) and extracted with EtOAc (30 mL). The organic phase was washed with brine (5 mL) and dried to give crude product. It was purified by chromatography (silica gel, 200-300 mesh, MeOH.:DMC, 1:20, v/v) to give N-(3-{3-[(thiophen-2-ylmethyl)-amino]-phenyl}-1H-pyrazolo[3,4-d]pyrimidin-6-yl)-cyclohexane-1,4-diamine as solid. (Yield 27 mg, 14.6%).

$^1$H NMR (300 MHz, CD$_3$OD): δ 8.82 (s, 1H), 7.28-7.17 (m, 4H), 7.07 (d, 1H, J=2.7 Hz), 6.98 (dd, 1H, J$_j$=5.1 Hz, J$_2$=3.6 Hz), 6.78 (s, 1H, J=8.4 Hz), 4.59 (s, 2H), 3.88 (brs, 1H), 2.93 (brs, 1H), 2.21-1.96 (m, 4H), 1.44-1.30 (m, 4H). LC-MS: [M+H]$^+$ 420.

Example 54

(2-Morpholin-4-yl-ethyl)-(3-{3-[(thiophen-2-ylmethyl)-amino]-phenyl}-1H-pyrazolo[3,4-d]pyrimidin-6-yl)-amine

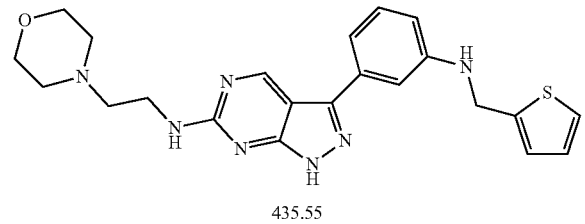 [SMILES: c1cc(NCc2cccs2)cc(-c2n[nH]c3nc(NCCN4CCOCC4)ncc23)c1]

435.55

Step A (2-Morpholin-4-yl-ethyl)-[3-{3-[(thiophen-2-ylmethyl)-amino]-phenyl}-1-(2-trimethylsilanyl-ethoxymethyl)-1H-pyrazolo[3,4-d]pyrimidin-6-yl]-amine

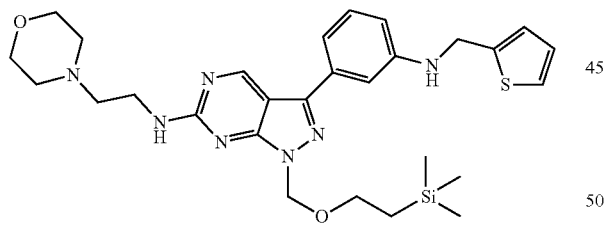

To a stirred solution of [3-(3-bromo-phenyl)-1-(2-trimethylsilanyl-ethoxymethyl)-1H-pyrazolo[3,4-d]pyrimidin-6-yl]-(2-morpholin-4-yl-ethyl)-amine (from Example 40 supra) (250 mg, 0.468 mmol), thiophen-2-yl-methylamine (80 mg, 0.70 mmol), DavePhos (30 mg, 0.076 mmol) and t-BuONa (70 mg, 0.73 mmol) in 1,4-dioxane (10 mL), Pd$_2$(dba)$_3$ (42 mg, 0.073 mmol) was added in one portion under N$_2$ atmosphere. The resultant mixture was stirred at 100° C. for 4 hours. The mixture was cooled and filtered; the filtrate was evaporated under reduced pressure to give the crude product. It was purified by chromatography (silica gel, 200-300 mesh, dichloromethane:MeOH, 100:1, v/v) to give (2-morpholin-4-yl-ethyl)-[3-{3-[(thiophen-2-ylmethyl)-amino]-phenyl}-1-(2-trimethylsilanyl-ethoxymethyl)-1H-pyrazolo[3,4-d]pyrimidin-6-yl]-amine. (Yield 170 mg, 64.2%).

LC-MS: [M+H]$^+$ 566.3.

Step B (2-Morpholin-4-yl-ethyl)-(3-{3-[(thiophen-2-ylmethyl)-amino]-phenyl}-1H-pyrazolo[3,4-d]pyrimidin-6-yl)-amine

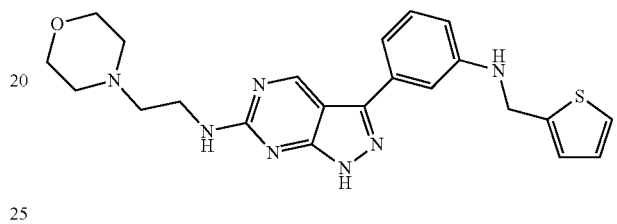

To a stirred solution of (2-morpholin-4-yl-ethyl)-[3-{3-[(thiophen-2-ylmethyl)-amino]-phenyl}-1-(2-trimethylsilanyl-ethoxymethyl)-1H-pyrazolo[3,4-d]pyrimidin-6-yl]-amine (170 mg, 0.3 mmol) in dichloromethane (10 mL) was added TFA (10 mL) at room temperature. The resulting mixture was stirred for another three hours at this temperature. The solvent was evaporated under reduced pressure and the residue was dissolved in EtOAc (10 mL). The organic phase was washed with saturated aqueous NaHCO$_3$ (3 mL), brine (5 mL) and dried over anhydrous Na$_2$SO$_4$, filtered and concentrated. It was purified by prep-HPLC to give (2-morpholin-4-yl-ethyl)-(3-{3-[(thiophen-2-ylmethyl)-amino]-phenyl}-1H-pyrazolo[3,4-d]pyrimidin-6-yl)-amine as yellow solid. (Yield 20 mg, 11.7%).

$^1$H NMR (300 MHz, CD$_3$OD): δ 9.01 (s, 1H), 7.44-7.35 (m, 4H), 7.13-6.96 (m, 3H), 4.70 (s, 2H), 4.01-3.50 (m, 12H). LC-MS: [M+H]$^+$ 436.

Example 55

N-{3-[3-(4-Chloro-benzylamino)-phenyl]-1H-pyrazolo[3,4-d]pyrimidin-6-yl}-cyclohexane-1,4-diamine

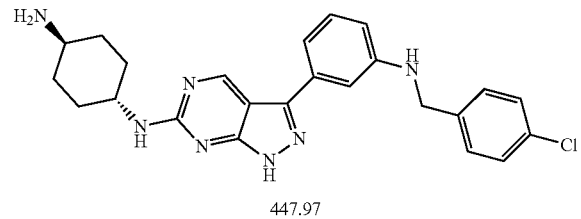 [SMILES: N[C@H]1CC[C@H](Nc2ncc3c(-c4cccc(NCc5ccc(Cl)cc5)c4)n[nH]c3n2)CC1]

447.97

Step A

{4-[3-[3-(4-Chloro-benzylamino)-phenyl]-1-(2-trimethylsilanyl-ethoxymethyl)-1H-pyrazolo[3,4-d]pyrimidin-6-ylamino]-cyclohexyl}-carbamic acid tert-butyl ester

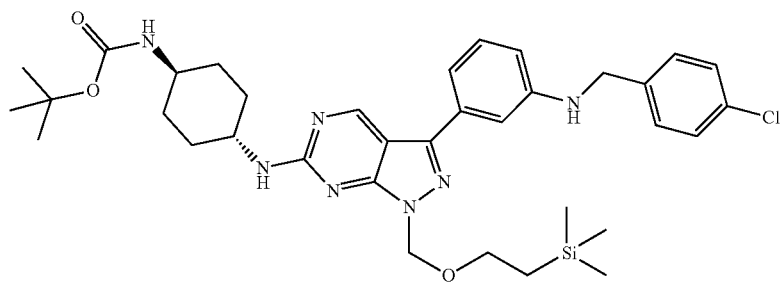 [SMILES: CC(C)(C)OC(=O)N[C@H]1CC[C@H](Nc2ncc3c(-c4cccc(NCc5ccc(Cl)cc5)c4)nn(COCC[Si](C)(C)C)c3n2)CC1]

To a stirred solution of {4-[3-(3-bromo-phenyl)-1-(2-trimethylsilanyl-ethoxymethyl)-1H-pyrazolo[3,4-d]pyrimidin-6-ylamino]-cyclohexyl}-carbamic acid tert-butyl ester (from Example 39 supra) (300 mg, 0.48 mmol), 4-chlorobenzylamine (120 mg, 1.06 mmol), DavePhos (20 mg, 0.048 mmol) and t-BuONa (56 mg, 0.58 mmol) in 1,4-dioxane (10 mL), Pd$_2$(dba)$_3$ (28 mg, 0.48 mmol) was added in one portion under N$_2$ atmosphere. The resultant mixture was stirred at 100° C. for 4 hours. The mixture was cooled and filtered; the filtrate was evaporated under reduced pressure to give the crude product. It was purified by chromatography (silica gel, 200-300 mesh, petroleum ether:EtOAc, 3:1, v/v) to give {-4-[3-[3-(4-chloro-benzylamino)-phenyl]-1-(2-trimethylsilanyl-ethoxymethyl)-1H-pyrazolo[3,4-d]pyrimidin-6-ylamino]-cyclohexyl}-carbamic acid tert-butyl ester. (Yield 120 mg, 36%).
LC-MS: [M+H]$^+$ 678.

Step B

N-{3-[3-(4-Chloro-benzylamino)-phenyl]-1H-pyrazolo[3,4-d]pyrimidin-6-yl}-cyclohexane-1,4-diamine

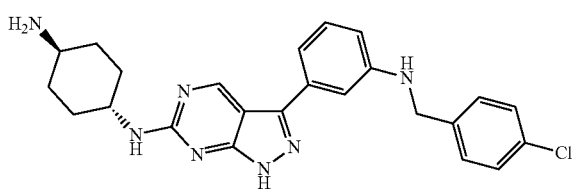 [SMILES: N[C@H]1CC[C@H](Nc2ncc3c(-c4cccc(NCc5ccc(Cl)cc5)c4)n[nH]c3n2)CC1]

To a stirred solution of {4-[3-[3-(4-chloro-benzylamino)-phenyl]-1-(2-trimethylsilanyl-ethoxymethyl)-1H-pyrazolo[3,4-d]pyrimidin-6-ylamino]-cyclohexyl}-carbamic acid tert-butyl ester (120 mg, 0.177 mmol) in dichloromethane (3 mL) was added TFA (3 mL) at room temperature. The resulting mixture was stirred for another four hours at this temperature. The solvent was evaporated under reduced pressure and the residue was treated with saturated aqueous NaHCO$_3$ (5 mL) and extracted with EtOAc (30 mL). The organic phase was washed with brine (5 mL) and dried to give crude product. It was purified by prep-HPLC to give N-{3-[3-(4-chloro-benzylamino)-phenyl]-1H-pyrazolo[3,4-d]pyrimidin-6-yl}-cyclohexane-1,4-diamine as solid. (Yield 25 mg, 31%).

$^1$H NMR (300 MHz, CD$_3$OD): δ 8.80 (s, 1H), 7.43-7.11 (m, 7H), 6.71 (d, 1H, J=7.8 Hz), 4.41 (s, 2H), 3.88-3.92 (m, 1H), 3.21-3.17 (m, 1H), 2.27-2.23 (m, 2H), 2.16-2.12 (m, 2H), 1.61-1.44 (m, 4H). LC-MS: [M+H]$^+$ 448.

Example 56

N-{3-[3-(2-Chloro-benzylamino)-phenyl]-1H-pyrazolo[3,4-d]pyrimidin-6-yl}-cyclohexane-1,4-diamine

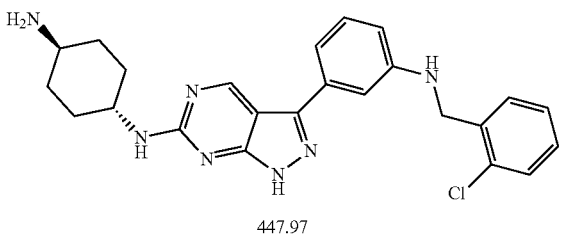 [SMILES: N[C@H]1CC[C@H](Nc2ncc3c(-c4cccc(NCc5ccccc5Cl)c4)n[nH]c3n2)CC1]

447.97

Step A

{4-[3-[3-(2-Chloro-benzylamino)-phenyl]-1-(2-trimethylsilanyl-ethoxymethyl)-1H-pyrazolo[3,4-d]pyrimidin-6-ylamino]-cyclohexyl}-carbamic acid tert-butyl ester

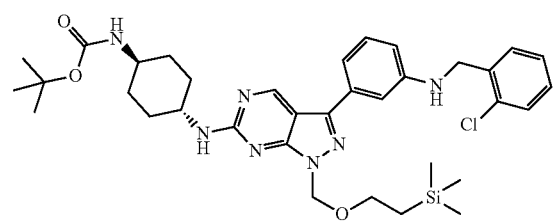 [SMILES: CC(C)(C)OC(=O)N[C@H]1CC[C@H](Nc2ncc3c(-c4cccc(NCc5ccccc5Cl)c4)nn(COCC[Si](C)(C)C)c3n2)CC1]

To a stirred solution of {4-[3-(3-bromo-phenyl)-1-(2-trimethylsilanyl-ethoxymethyl)-1H-pyrazolo[3,4-d]pyrimidin-6-ylamino]-cyclohexyl}-carbamic acid tert-butyl ester (from Example 39 supra) (300 mg, 0.486 mmol), 2-chlorobenzylamine (83 mg, 0.583 mmol), DavePhos (38 mg) and t-BuONa (56 mg, 0.58 mmol) in 1,4-dioxane (5 mL), Pd$_2$(dba)$_3$ (28 mg, 0.48 mmol) was added in one portion under N$_2$ atmosphere. The resultant mixture was stirred at 100° C. for 4 hours. The mixture was cooled and filtered; the filtrate was evaporated under reduced pressure to give the crude product. It was purified by chromatography (silica gel, 200-300 mesh, petroleum ether:EtOAc, 3:1, v/v) to give {4-[3-[3-(2-chloro-benzylamino)-phenyl]-1-(2-trimethylsilanyl-ethoxymethyl)-1H-pyrazolo[3,4-d]pyrimidin-6-ylamino]-cyclohexyl}-carbamic acid tert-butyl ester. (Yield 110 mg, 33%).

LC-MS: [M+H]$^+$ 678.

Step B

N-{3-[3-(2-Chloro-benzylamino)-phenyl]-1H-pyrazolo[3,4-d]pyrimidin-6-yl}-cyclohexane-1,4-diamine

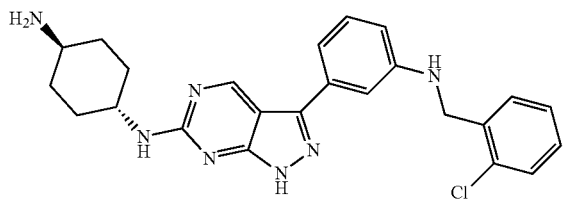 [SMILES: N[C@H]1CC[C@H](Nc2ncc3c(-c4cccc(NCc5ccccc5Cl)c4)n[nH]c3n2)CC1]

To a stirred solution of {4-[3-[3-(2-chloro-benzylamino)-phenyl]-1-(2-trimethylsilanyl-ethoxymethyl)-1H-pyrazolo[3,4-d]pyrimidin-6-ylamino]-cyclohexyl}-carbamic acid tert-butyl ester (110 mg, 0.162 mmol) in dichloromethane (3 mL) was added TFA (3 mL) at room temperature. The resulting mixture was stirred for another four hours at this temperature. The solvent was evaporated under reduced pressure and the residue was treated with saturated aqueous NaHCO$_3$ (5 mL) and extracted with EtOAc (30 mL). The organic phase was washed with brine (5 mL) and dried to give crude product. It was purified by prep-HPLC to give N-{3-[3-(2-chloro-benzylamino)-phenyl]-1H-pyrazolo[3,4-d]pyrimidin-6-yl}-cyclohexane-1,4-diamine as solid. (Yield 15 mg, 21%).

$^1$H NMR (300 MHz, CD$_3$OD): δ 8.78 (s, 1H), 7.51-7.40 (m, 2H), 7.26-7.07 (m, 5H), 6.71-6.68 (m, 1H), 4.50 (s, 2H), 3.88-3.91 (m, 1H), 3.24-3.15 (m, 1H), 2.26-2.13 (m, 4H), 1.62-1.44 (m, 4H). LC-MS: [M+H]$^+$ 448.

Example 57

{3-[3-(2-Chloro-benzylamino)-phenyl]-1H-pyrazolo[3,4-d]pyrimidin-6-yl}-(2-morpholin-4-yl-ethyl)-amine

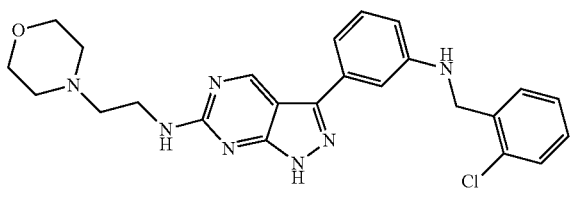

463.97

Step A

[3-[3-(2-Chloro-benzylamino)-phenyl]-1-(2-trimethylsilanyl-ethoxymethyl)-1H-pyrazolo[3,4-d]pyrimidin-6-yl]-(2-morpholin-4-yl-ethyl)-amine

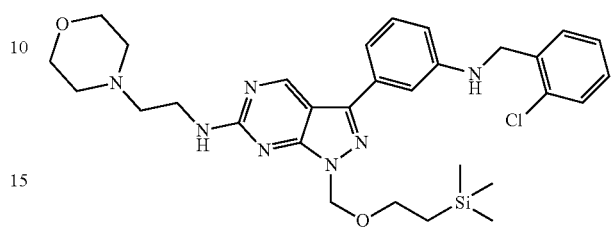

To a stirred solution of [3-(3-bromo-phenyl)-1-(2-trimethylsilanyl-ethoxymethyl)-1H-pyrazolo[3,4-d]pyrimidin-6-yl]-(2-morpholin-4-yl-ethyl)-amine (from Example 40 supra) (250 mg, 0.468 mmol), 2-chlorobenzylamine (80 mg, 0.564 mmol), DavePhos (37 mg) and t-BuONa (54 mg, 0.564 mmol) in 1,4-dioxane (10 mL), Pd$_2$(dba)$_3$ (42 mg, 0.073 mmol) was added in one portion under N$_2$ atmosphere. The resultant mixture was stirred at 100° C. for 6 hours. The mixture was cooled and filtered; the filtrate was evaporated under reduced pressure to give the crude product. It was purified by chromatography (silica gel, 200-300 mesh, dichloromethane:MeOH, 100:1, v/v) to give [3-[3-(2-chloro-benzylamino)-phenyl]-1-(2-trimethylsilanyl-ethoxymethyl)-1H-pyrazolo[3,4-d]pyrimidin-6-yl]-(2-morpholin-4-yl-ethyl)-amine. (Yield 120 mg, 43%).

LC-MS: [M+H]$^+$ 594.

Step B

{3-[3-(2-Chloro-benzylamino)-phenyl]-1H-pyrazolo[3,4-d]pyrimidin-6-yl}-(2-morpholin-4-yl-ethyl)-amine

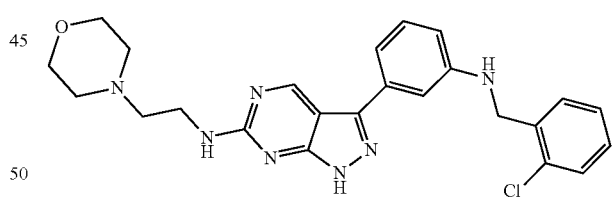

To a stirred solution of [3-[3-(2-chloro-benzylamino)-phenyl]-1-(2-trimethylsilanyl-ethoxymethyl)-1H-pyrazolo[3,4-d]pyrimidin-6-yl]-(2-morpholin-4-yl-ethyl)-amine (120 mg, 0.202 mmol) in dichloromethane (3 mL) was added TFA (3 mL) at room temperature. The resulting mixture was stirred for another three hours at this temperature. The solvent was evaporated under reduced pressure and the pH of the residue was adjusted to 8 with saturated NaHCO$_3$. The resulting mixture was extracted with EtOAc (10 mL), dried and concentrated. It was purified by prep-HPLC to give {3-[3-(2-chloro-benzylamino)-phenyl]-1H-pyrazolo[3,4-d]pyrimidin-6-yl}-(2-morpholin-4-yl-ethyl)-amine. (Yield 15 mg, 61%).

$^1$H NMR (300 MHz, CD$_3$OD): δ8.76 (s, 1H), 7.51-7.42 (m, 2H), 7.27-7.07 (m, 5H), 6.68 (d, 1H, J$_1$=7.8 Hz, J$_2$=1.2 Hz), 4.51 (s, 2H), 3.75-3.72 (m, 4H), 3.62 (t, 2H, J=6.6 Hz), 2.69-2.57 (m, 6H). LC-MS: [M+H]⁺ 464; [M−H]⁺ 462.

Example 58

N-(3-{3-[(Thiophen-3-ylmethyl)-amino]-phenyl}-1H-pyrazolo[3,4-d]pyrimidin-6-yl)-cyclohexane-1,4-diamine

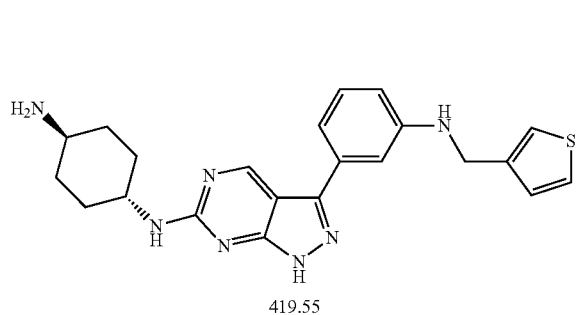 [SMILES: N[C@H]1CC[C@H](Nc2ncc3c(-c4cccc(NCc5ccsc5)c4)n[nH]c3n2)CC1]

419.55

Step A

{4-[3-{3-[(Thiophen-3-ylmethyl)-amino]-phenyl}-1-(2-trimethylsilanyl-ethoxymethyl)-1H-pyrazolo[3,4-d]pyrimidin-6-ylamino]-cyclohexyl}-carbamic acid tert-butyl ester

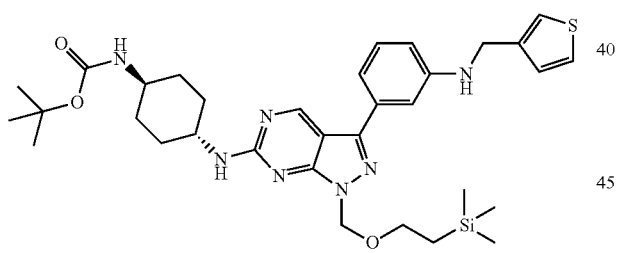

To a stirred solution of {4-[3-(3-bromo-phenyl)-1-(2-trimethylsilanyl-ethoxymethyl)-1H-pyrazolo[3,4-d]pyrimidin-6-ylamino]-cyclohexyl}-carbamic acid tert-butyl ester (from Example 39 supra) (300 mg, 0.48 mmol), thiophen-3-yl-methylamine (66 mg, 0.583 mmol), DavePhos (38 mg, 20 mol %) and t-BuONa (56 mg, 0.58 mmol) in 1,4-dioxane (10 mL), Pd₂(dba)₃ (28 mg, 0.48 mmol) was added in one portion under N₂ atmosphere. The resultant mixture was stirred at 100° C. for 5 hours. The mixture was cooled and filtered; the filtrate was evaporated under reduced pressure to give the crude product. It was purified by chromatography (silica gel, 200-300 mesh, petroleum ether:EtOAc, 3:1, v/v) to give {4-[3-{3-[(thiophen-3-ylmethyl)-amino]-phenyl}-1-(2-trimethylsilanyl-ethoxymethyl)-1H-pyrazolo[3,4-d]pyrimidin-6-ylamino]-cyclohexyl}-carbamic acid tert-butyl ester. (Yield 120 mg, 38%).

LC-MS: [M+H]⁺ 650.

Step B

N-(3-{3-[(Thiophen-3-ylmethyl)-amino]-phenyl}-1H-pyrazolo[3,4-d]pyrimidin-6-yl)-cyclohexane-1,4-diamine

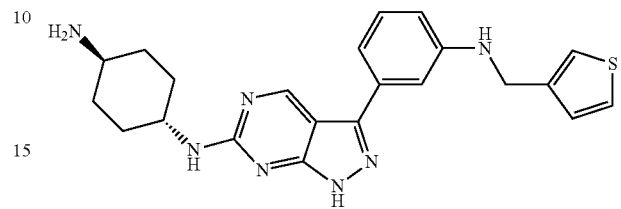

To a stirred solution of {4-[3-{3-[(thiophen-3-ylmethyl)-amino]-phenyl}-1-(2-trimethylsilanyl-ethoxymethyl)-1H-pyrazolo[3,4-d]pyrimidin-6-ylamino]-cyclohexyl}-carbamic acid tert-butyl ester (120 mg, 0.185 mmol) in dichloromethane (3 mL) was added TFA (3 mL) at room temperature. The resulting mixture was stirred for another two hours at this temperature. The solvent was evaporated under reduced pressure and the residue was treated with saturated aqueous NaHCO₃ (5 mL) and extracted with EtOAc (30 mL). The organic phase was washed with brine (5 mL) and dried to give crude product. It was purified by prep-HPLC to give N-(3-{3-[(thiophen-3-ylmethyl)-amino]-phenyl}-1H-pyrazolo[3,4-d]pyrimidin-6-yl)-cyclohexane-1,4-diamine as solid. (Yield 75 mg, 84%).

¹H NMR (300 MHz, CD₃OD): δ 8.80 (s, 1H), 7.38 (dd, 1H, J₁=4.8 Hz, J₂=3.0 Hz), 7.29-7.13 (m, 5H), 6.77 (d, 1H, J=5.7 Hz), 4.41 (s, 2H), 3.85 (brs, 1H), 2.77 (brs, 1H), 2.14-1.97 (m, 4H), 1.46-1.28 (m, 4H). LC-MS: [M+H]⁺ 420.

Example 59

{3-[6-(2-Chloro-benzylamino)-pyridin-2-yl]-1H-pyrazolo[3,4-d]pyrimidin-6-yl}-(2-morpholin-4-yl-ethyl)-amine

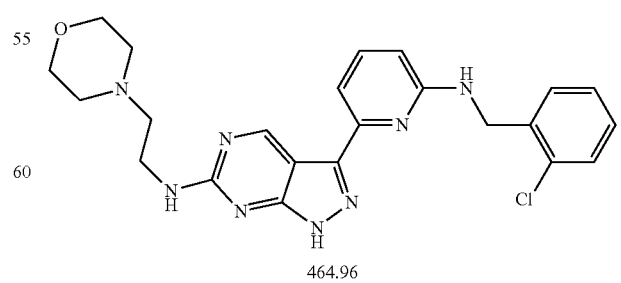

464.96

Step A

[3-[6-(2-Chloro-benzylamino)-pyridin-2-yl]-1-(2-trimethylsilanyl-ethoxymethyl)-1H-pyrazolo[3,4-d]pyrimidin-6-yl]-(2-morpholin-4-yl-ethyl)-amine

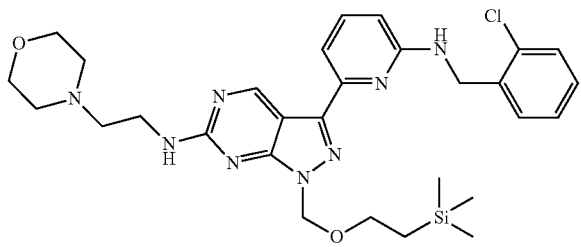 [SMILES: C[Si](C)(C)CCOCn1nc(-c2cccc(NCc3ccccc3Cl)n2)c2cnc(NCCN3CCOCC3)nc21]

A sealed tube was charged with [3-(6-bromo-pyridin-2-yl)-1-(2-trimethylsilanyl-ethoxymethyl)-1H-pyrazolo[3,4-d]pyrimidin-6-yl]-(2-morpholin-4-yl-ethyl)-amine (from Example 32 supra) (350 mg, 0.655 mmol), 2-chlorobenzylamine (130 mg, 0.918 mmol), Pd₂(dba)₃ (38 mg, 0.066 mmol), DavePhos (52 mg, 0.132 mmol), t-BuONa (88 mg, 0.917 mmol) and dioxane (16 mL). The mixture was stirred at 102° C. under an atmosphere of N₂ for 15 hours. After cooling to room temperature, the mixture was filtered and concentrated under reduced pressure. The residue was purified by column chromatography (silica gel, 20 g, 200-300 mesh, eluting with dichloromethane:MeOH, 80:1) to give [3-[6-(2-chloro-benzylamino)-pyridin-2-yl]-1-(2-trimethylsilanyl-ethoxymethyl)-1H-pyrazolo[3,4-d]pyrimidin-6-yl]-(2-morpholin-4-yl-ethyl)-amine. (Yield 276 mg, 71%).

LC-MS: [M+H]⁺ 595.

Step B

{3-[6-(2-Chloro-benzylamino)-pyridin-2-yl]-1H-pyrazolo[3,4-d]pyrimidin-6-yl}-(2-morpholin-4-yl-ethyl)-amine

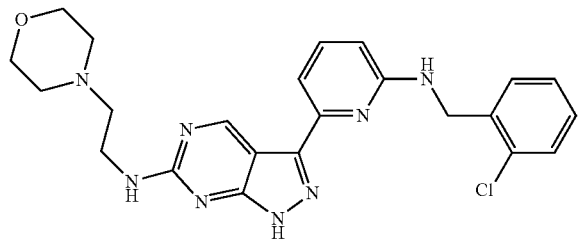 [SMILES: Clc1ccccc1CNc1cccc(-c2n[nH]c3nc(NCCN4CCOCC4)ncc23)n1]

To a mixture of [3-[6-(2-chloro-benzylamino)-pyridin-2-yl]-1-(2-trimethylsilanyl-ethoxy-methyl)-1H-pyrazolo[3,4-d]pyrimidin-6-yl]-(2-morpholin-4-yl-ethyl)-amine (276 mg, 0.465 mmol) in dichloromethane (4 mL) was added CF₃COOH (3.6 mL). This mixture was stirred at room temperature for 3 hours. The solvent was removed under reduced pressure. A saturated aqueous solution of NaHCO₃ was added to the residue, and then extracted with ethyl acetate (3×15 mL). The combined organic phase was dried over anhydrous Na₂SO₄, filtered and concentrated under reduced pressure. The residue was purified by prep-HPLC to give [3-[6-(2-chloro-benzylamino)-pyridin-2-yl]-1-(2-trimethylsilanyl-ethoxymethyl)-1H-pyrazolo[3,4-d]pyrimidin-6-yl]-(2-morpholin-4-yl-ethyl)-amine as a yellow solid. (Yield 130 mg, 60.3%).

¹H NMR (300 MHz, DMSO): δ 8.90 (s, 1H), 7.57-7.41 (m, 5H), 7.29-7.26 (m, 3H), 6.69 (q, 2H, J=7.5 Hz), 5.52 (d, 2H, J=6.9 Hz), 4.68 (d, 2H, J=5.7 Hz), 3.58-3.40 (m, 6H), 2.44 (brs, 4H). LC-MS: [M+H]⁺ 465.

Example 60

(2-Morpholin-4-yl-ethyl)-(3-{6-[(thiophen-3-ylmethyl)-amino]-pyridin-2-yl}-1H-pyrazolo[3,4-d]pyrimidin-6-yl)-amine

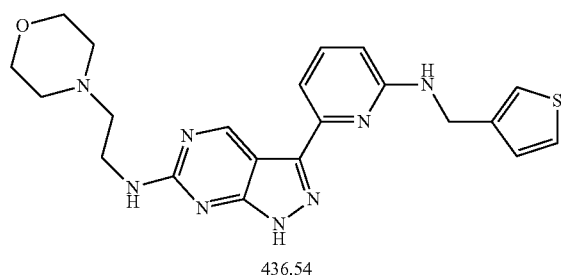 [SMILES: c1cc(NCc2ccsc2)nc(-c2n[nH]c3nc(NCCN4CCOCC4)ncc23)c1]

436.54

Step A (2-Morpholin-4-yl-ethyl)-[3-{6-[(thiophen-3-ylmethyl)-amino]-pyridin-2-yl}-1-(2-trimethylsilanyl-ethoxymethyl)-1H-pyrazolo[3,4-d]pyrimidin-6-yl]-amine

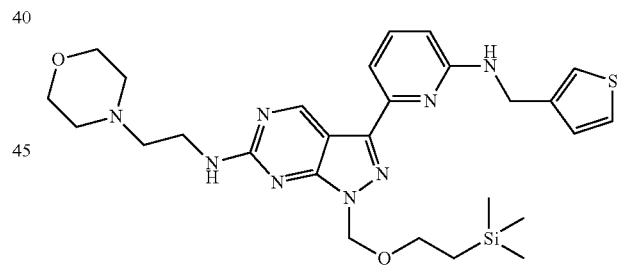

A sealed tube was charged with [3-(6-bromo-pyridin-2-yl)-1-(2-trimethylsilanyl-ethoxymethyl)-1H-pyrazolo[3,4-d]pyrimidin-6-yl]-(2-morpholin-4-yl-ethyl)-amine (from Example 32 supra) (320 mg, 0.60 mmol), thiophen-3-ylmethylamine (81 mg, 0.72 mmol), Pd₂(dba)₃ (34 mg), DavePhos (47 mg), t-BuONa (69 mg, 0.72 mmol) and dioxane (12 mL). The mixture was stirred at 105° C. under an atmosphere of N₂ for 8 hours. After cooling to room temperature, the mixture was filtered and concentrated under reduced pressure. The residue was purified by column chromatography (silica gel, 16 g, 100-200 mesh, eluting with MeOH:dichloromethane, 1:100 to 1:80) to give crude (2-morpholin-4-yl-ethyl)-[3-{6-[(thiophen-3-ylmethyl)-amino]-pyridin-2-yl}-1-(2-trimethylsilanyl-ethoxymethyl)-1H-pyrazolo[3,4-d]pyrimidin-6-yl]-amine as a yellow oil. (Yield 149 mg)

LC-MS: [M+H]⁺ 567. .

Step B (2-Morpholin-4-yl-ethyl)-(3-{6-[(thiophen-3-ylmethyl)-amino]-pyridin-2-yl}-1H-pyrazolo[3,4-d]pyrimidin-6-yl)-amine

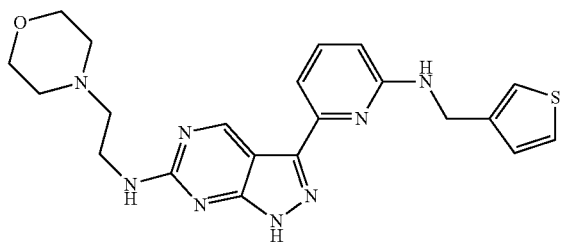 [SMILES: c1cc(NCc2ccsc2)nc(-c2n[nH]c3nc(NCCN4CCOCC4)ncc23)c1]

To a mixture of crude (2-morpholin-4-yl-ethyl)-[3-{6-[(thiophen-3-ylmethyl)-amino]-pyridin-2-yl}-1-(2-trimethylsilanyl-ethoxymethyl)-1H-pyrazolo[3,4-d]pyrimidin-6-yl]-amine (149 mg, crude) in dichloromethane (2 mL) was added CF$_3$COOH (2 mL). This mixture was stirred at room temperature for 2 hours. The solvent was removed under reduced pressure. A saturated aqueous solution of NaHCO$_3$ was added to the residue, and then extracted with ethyl acetate (3×15 mL). The combined organic phase was dried over anhydrous MgSO$_4$, filtered and concentrated under reduced pressure. The residue was washed with dichloromethane (2 mL) to give (2-morpholin-4-yl-ethyl)-(3-{6-[(thiophen-3-ylmethyl)-amino]-pyridin-2-yl}-1H-pyrazolo[3,4-d]pyrimidin-6-yl)-amine as a white solid. (Yield 46 mg, 18% over two steps).

$^1$H NMR (300 MHz, DMSO): δ 9.27 (s, 1H), 7.54-7.14 (m, 7H), 5.54 (d, 2H, J=7.5 Hz), 4.58 (d, 2H, J=5.7 Hz), 3.57-3.48 (m, 6H), 2.51-2.44 (m, 6H). LC-MS: [M+H]$^+$ 437; [M−H]$^+$ 435.

Example 61

[3-(2-Benzylamino-pyrimidin-4-yl)-1H-pyrazolo[3,4-d]pyrimidin-6-yl]-(2-morpholin-4-yl-ethyl)-amine; hydrochloride

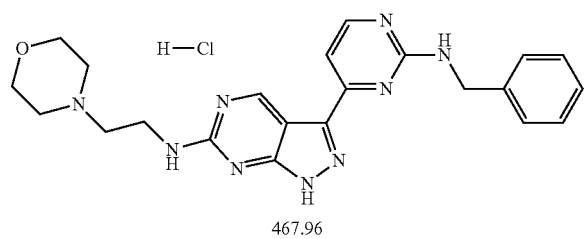 [SMILES: c1ccc(CNc2nccc(-c3n[nH]c4nc(NCCN5CCOCC5)ncc34)n2)cc1 ; Cl]

467.96

To the solution of [3-(2-methanesulfonyl-pyrimidin-4-yl)-1H-pyrazolo[3,4-d]pyrimidin-6-yl]-(2-morpholin-4-yl-ethyl)-amine (from Example 11 supra) (220 mg, 0.54 mmol) and benzyl-amine (70 mg, 0.65 mmol) in DMSO (15 mL) was added DIPEA (84 mg, 0.65 mmol). The mixture was heated at 130° C. with stirring under N$_2$ for 4 hours. The solvent was removed under reduced pressure. The residue was first purified by column chromatography (silica gel, dichloromethane:MeOH, 50:1 to 30:1), then by prep-HPLC. Concentrated HCl was added to the fractions with product and concentrated under reduced pressure to give [3-(2-benzylamino-pyrimidin-4-yl)-1H-pyrazolo[3,4-d]pyrimidin-6-yl]-(2-morpholin-4-yl-ethyl)-amine; hydrochloride. (Yield 40 mg, 17.1%).

$^1$H NMR (300 MHz, CD$_3$OD): δ 9.14 (s, 1H), 8.45 (s, 1H), 7.75 (d, 1H, J=6.6 Hz), 7.51-7.37 (m, 4H), 4.98-4.84 (m, 2H), 4.10-3.86 (m, 6H), 3.75-3.71 (m, 2H), 3.55-3.53 (m, 2H), 3.27-3.23 (m, 2H). LC-MS: [M+H]$^+$ 432; [M−H]$^+$ 430.

Example 62

{3-[2-(3-Chloro-benzylamino)-pyrimidin-4-yl]-1H-pyrazolo[3,4-d]pyrimidin-6-yl}-(2-morpholin-4-yl-ethyl)-amine; hydrochloride

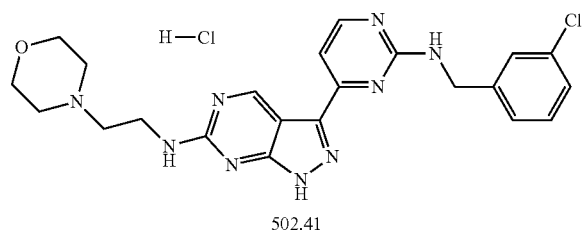 [SMILES: Clc1cccc(CNc2nccc(-c3n[nH]c4nc(NCCN5CCOCC5)ncc34)n2)c1 ; Cl]

502.41

{3-[2-(3-Chloro-benzylamino)-pyrimidin-4-yl]-1H-pyrazolo [3,4-d]pyrimidin-6-yl}-(2-morpholin-4-yl-ethyl)-amine; hydrochloride was prepared from [3-(2-methanesulfonyl-pyrimidin-4-yl)-1H-pyrazolo[3,4-d]pyrimidin-6-yl]-(2-morpholin-4-yl-ethyl)-amine (from Example 11 supra) (300 mg, 0.74 mmol) and 3-chlorobenzylamine by following the method in Example 61. (Yield 45 mg, 19.6%).

$^1$H NMR (300 MHz, CD$_3$OD): δ 9.21 (s, 1H), 8.49 (s, 1H), 7.76 (d, 1H, J=5.7 Hz), 7.54-7.36 (m, 4H), 4.89-4.84 (m, 2H), 4.09-3.92 (m, 6H), 3.77-3.73 (m, 2H), 3.58 (brs, 2H), 3.32-3.26 (m, 2H). LC-MS: [M+H]$^+$ 466; [M−H]$^+$ 464.

Example 63

{3-[2-(2-Chloro-benzylamino)-pyrimidin-4-yl]-1H-pyrazolo[3,4-d]pyrimidin-6-yl}-(2-morpholin-4-yl-ethyl)-amine; hydrochloride

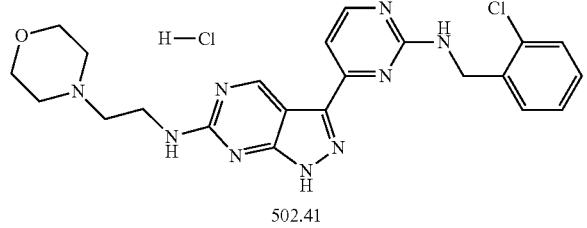

502.41

{3-[2-(2-Chloro-benzylamino)-pyrimidin-4-yl]-1H-pyrazolo [3,4-d]pyrimidin-6-yl}-(2-morpholin-4-yl-ethyl)-amine; hydrochloride was prepared from [3-(2-methanesulfonyl-pyrimidin-4-yl)-1H-pyrazolo[3,4-d]pyrimidin-6-yl]-(2-morpholin-4-yl-ethyl)-amine (from Example 11 supra) (300 mg, 0.74 mmol) and 2-chlorobenzylamine by following the method in Example 61. (Yield 50 mg, 14.5%).

$^1$H NMR (300 MHz, CD$_3$OD): δ 9.09 (s, 1H), 8.47 (s, 1H), 7.78 (d, 1H, J=6.3 Hz), 7.57-7.24 (m, 2H), 7.39 (brs, 2H), 5.05-4.98 (m, 2H), 4.10-3.86 (m, 6H), 3.75-3.71 (m, 2H), 3.55-3.52 (m, 2H), 3.26-3.23 (m, 2H). LC-MS: [M+H]$^+$ 466; [M−H]$^+$ 464.

Example 64

{3-[2-(4-Chloro-benzylamino)-pyrimidin-4-yl]-1H-pyrazolo[3,4-d]pyrimidin-6-yl}-(2-morpholin-4-yl-ethyl)-amine; hydrochloride

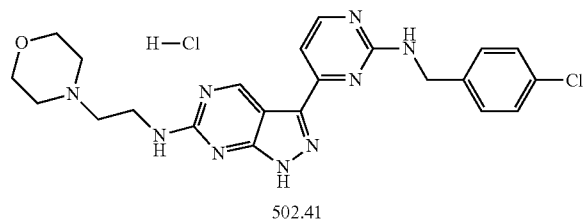 [SMILES: Clc1ccc(CNc2nccc(-c3n[nH]c4nc(NCCN5CCOCC5)ncc34)n2)cc1 ; Cl]

502.41

{3-[2-(4-Chloro-benzylamino)-pyrimidin-4-yl]-1H-pyrazolo[3,4-d]pyrimidin-6-yl}-(2-morpholin-4-yl-ethyl)-amine; hydrochloride was prepared from [3-(2-methanesulfonyl-pyrimidin-4-yl)-1H-pyrazolo[3,4-d]pyrimidin-6-yl]-(2-morpholin-4-yl-ethyl)-amine (from Example 11 supra) (300 mg, 0.74 mmol) and 2-chlorobenzylamine by following the method in Example 61. (Yield 54 mg, 23.4%).

$^1$H NMR (300 MHz, CD$_3$OD): δ 9.15 (s, 1H), 8.45 (s, 1H), 7.76 (d, 1H, J=6.0 Hz), 7.51-7.41 (m, 4H), 5.03-4.77 (m, 2H), 4.10-3.70 (m, 8H), 3.55-3.53 (m, 2H), 3.27-3.23 (m, 2H). LC-MS: [M+H]$^+$ 466; [M−H]$^+$ 464.

Example 65

N-(3-{6-[(Thiophen-3-ylmethyl)-amino]-pyridin-2-yl}-1H-pyrazolo[3,4-d]pyrimidin-6-yl)-cyclohexane-1,4-diamine; hydrochloride

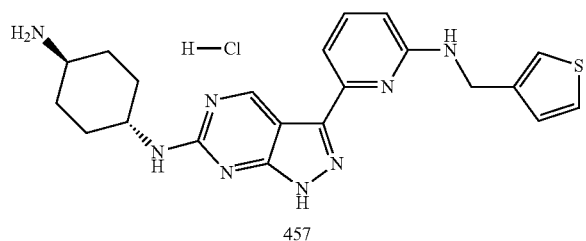

457

Step A

{4-[3-{6-[(Thiophen-3-ylmethyl)-amino]-pyridin-2-yl}-1-(2-trimethylsilanyl-ethoxymethyl)-1H-pyrazolo[3,4-d]pyrimidin-6-ylamino]-cyclohexyl}-carbamic acid tert-butyl ester

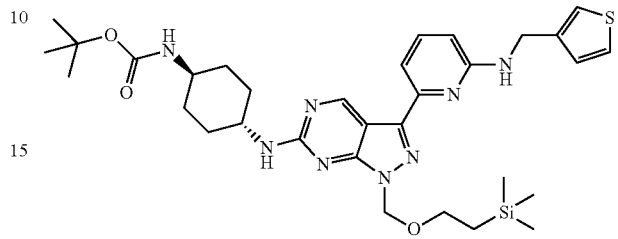

A sealed tube was charged with {4-[3-(6-bromo-pyridin-2-yl)-1-(2-trimethylsilanyl-ethoxymethyl)-1H-pyrazolo[3,4-d]pyrimidin-6-ylamino]-cyclohexyl}-carbamic acid tert-butyl ester (from Example 33 supra) (500 mg, 0.809 mmol), thiophen-3-yl-methylamine (118 mg, 1.044 mmol), Pd$_2$(dba)$_3$ (47 mg, 0.0817 mmol), DavePhos (64 mg, 0.163 mmol), t-BuONa (109 mg, 1.135 mmol) and dioxane (20 mL). The mixture was stirred at 102° C. under an atmosphere of N$_2$ for 12 hours. After cooling to room temperature, the mixture was filtered and concentrated under reduced pressure. The residue was purified by column chromatography (silica gel, 12 g, 200-300 mesh, eluting with petroleum ether: ethyl acetate, 3:1) to give {4-[3-{6-[(thiophen-3-ylmethyl)-amino]-pyridin-2-yl}-1-(2-trimethylsilanyl-ethoxymethyl)-1H-pyrazolo[3,4-d]pyrimidin-6-ylamino]-cyclohexyl}-carbamic acid tert-butyl ester. (Yield 415 mg, 79%).

LC-MS: [M+H]$^+$ 651.

Step B

N-(3-{6-[(Thiophen-3-ylmethyl)-amino]-pyridin-2-yl}-1H-pyrazolo[3,4-d]pyrimidin-6-yl)-cyclohexane-1,4-diamine; hydrochloride

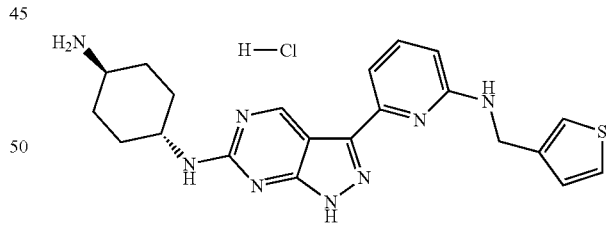

To a mixture of {4-[3-{6-[(thiophen-3-ylmethyl)-amino]-pyridin-2-yl}-1-(2-trimethylsilanyl-ethoxymethyl)-1H-pyrazolo[3,4-d]pyrimidin-6-ylamino]-cyclohexyl}-carbamic acid tert-butyl ester (415 mg, 0.638 mmol) in dichloromethane (5 mL) was added CF$_3$COOH (5 mL). The mixture was stirred at room temperature for 2 hours. The solvent was removed under reduced pressure. A saturated aqueous solution of NaHCO$_3$ was added to the residue, and then extracted with ethyl acetate (3×15 mL). The combined organic phase was dried over anhydrous Na$_2$SO$_4$, filtered and concentrated under reduced pressure. After purification by prep-HPLC, concentrated HCl was added to the fractions with product and concentrated under reduced pressure to give N-(3-{6-[(thiophen-3-ylmethyl)-amino]-pyridin-2-yl}-1H-pyrazolo[3,4-d]pyrimidin-6-yl)-cyclohexane-1,4-diamine; hydrochloride. (Yield 27 mg).

¹H NMR (300 MHz, CD₃OD): δ 9.32 (s, 1H), 8.02 (dd, 1H, J₁=9.3 Hz, J₂=7.8 Hz), 7.51 (d, 1H, J=7.5 Hz), 7.39-7.37 (m, 2H), 7.14 (d, 1H, J=9.0 Hz), 7.07 (dd, 1H, J₁=4.2 Hz, J₂=2.1 Hz), 4.63 (s, 2H), 3.94 (brs, 1H), 3.19 (brs, 2H), 2.16-2.05 (m, 4H), 1.49-1.15 (m, 4H). LC-MS: [M+H]⁺ 421.

Example 66

N-(3-{2-[(Thiophen-3-ylmethyl)-amino]-pyrimidin-4-yl}-1H-pyrazolo[3,4-d]pyrimidin-6-yl)-cyclohexane-1,4-diamine; hydrochloride

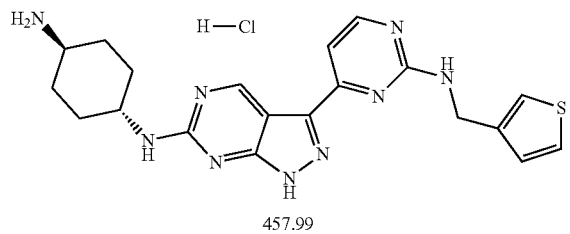 [SMILES: N[C@H]1CC[C@H](Nc2ncc3c(-c4ccnc(NCc5ccsc5)n4)n[nH]c3n2)CC1 ; Cl]

457.99

Step A

[4-(3-{2-[(Thiophen-3-ylmethyl)-amino]-pyrimidin-4-yl}-1H-pyrazolo[3,4-d]pyrimidin-6-ylamino)-cyclohexyl]-carbamic acid tert-butyl ester

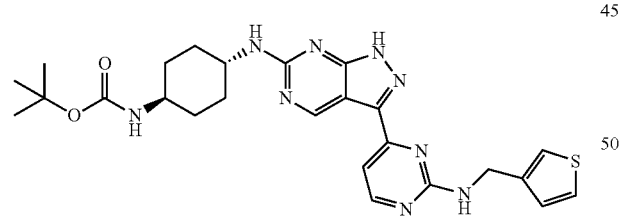

The mixture of {4-[3-(2-methanesulfinyl-pyrimidin-4-yl)-1H-pyrazolo[3,4-d]pyrimidin-6-ylamino]-cyclohexyl}-carbamic acid tert-butyl ester (from Example 9 supra) (200 mg, 0.42 mmol) and thiophen-3-yl-methylamine (239 mg, 2.1 mmol) was heated at 130° C. with stirring for 4 hours. The resulting oil was purified by chromatography (silica gel, 8 g, 200-300 mesh, eluting with dichloromethane:methanol, 50:1 to 30:1) and then further purified by prep-HPLC to afford [4-(3-{2-[(thiophen-3-ylmethyl)-amino]-pyrimidin-4-yl}-1H-pyrazolo[3,4-d]pyrimidin-6-ylamino)-cyclohexyl]-carbamic acid tert-butyl ester. (Yield 24 mg, 10.9%).

LC-MS: [M+H]⁺ 522.

Step B

N-(3-{2-[(Thiophen-3-ylmethyl)-amino]-pyrimidin-4-yl}-1H-pyrazolo[3,4-d]pyrimidin-6-yl)-cyclohexane-1,4-diamine; hydrochloride

To a solution of [4-(3-{2-[(thiophen-3-ylmethyl)-amino]-pyrimidin-4-yl}-1H-pyrazolo[3,4-d]pyrimidin-6-ylamino)-cyclohexyl]-carbamic acid tert-butyl ester (24 mg, 0.046 mmol) in methanol (30 mL) was bubbled in HCl (gas) for 3 hours at room temperature. The mixture was then concentrated by evaporation to afford N-(3-{2-[(thiophen-3-ylmethyl)-amino]-pyrimidin-4-yl}-1H-pyrazolo[3,4-d]pyrimidin-6-yl)-cyclohexane-1,4-diamine; hydrochloride. (Yield 25 mg, 96%).

¹H NMR (300 MHz, CD₃OD): δ 9.09 (s, 1H), 8.43 (d, 1H, J=7.2 Hz), 7.73 (d, 1H, J=6.6 Hz), 7.52-7.50 (m, 2H), 7.25 (d, 1H, J=3 Hz), 4.01 (brs, 1H), 3.37-3.34 (m, 2H), 3.21 (brs, 1H), 2.29-2.17 (m, 4H), 1.69-1.56 (m, 4H). LC-MS: [M+H]⁺ 422; [M−H]⁺ 420.

Example 67

N-{3-[2-(2-Amino-1-phenyl-ethylamino)-pyrimidin-4-yl]-1H-pyrazolo[3,4-d]pyrimidin-6-yl}-cyclohexane-1,4-diamine; hydrochloride

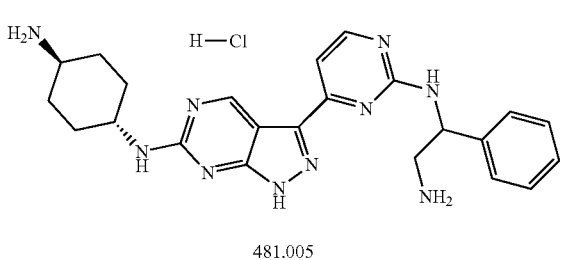 [SMILES: NCC(Nc1nccc(-c2n[nH]c3nc(N[C@H]4CC[C@H](N)CC4)ncc23)n1)c1ccccc1 ; Cl]

481.005

Step A (4-{3-[2-(2-tert-Butoxycarbonylamino-1-phenyl-ethylamino)-pyrimidin-4-yl]-1H-pyrazolo[3,4-d]pyrimidin-6-ylamino}-cyclohexyl)-carbamic acid tert-butyl ester

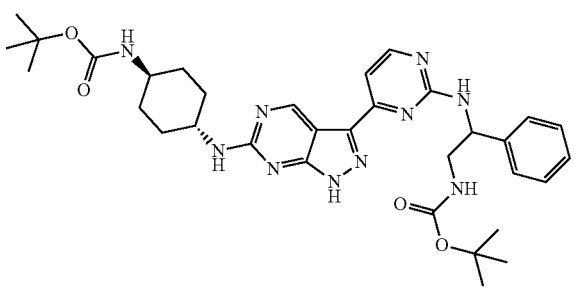 [SMILES: CC(C)(C)OC(=O)NCC(Nc1nccc(-c2n[nH]c3nc(N[C@H]4CC[C@H](NC(=O)OC(C)(C)C)CC4)ncc23)n1)c1ccccc1]

The mixture of {4-[3-(2-methanesulfinyl-pyrimidin-4-yl)-1H-pyrazolo[3,4-d]pyrimidin-6-ylamino]-cyclohexyl}-carbamic acid tert-butyl ester (from Example 9 supra) (300 mg, 0.64 mmol) and (2-amino-2-phenyl-ethyl)-carbamic acid tert-butyl ester (from Example 1 supra) (600 mg, 2.5 mmol) was heated at 130° C. with stirring for 2 hours. The resulting oil was purified by chromatography (silica gel, 8 g, 200-300 mesh, eluting with dichloromethane:methanol, 50:1 to 30:1) and then further purified by prep-HPLC to afford (4-{3-[2-(2-tert-butoxycarbonylamino-1-phenyl-ethylamino)-pyrimidin-4-yl]-1H-pyrazolo[3,4-d]pyrimidin-6-ylamino}-cyclohexyl)-carbamic acid tert-butyl ester. (Yield 35 mg, 8.5%).

LC-MS: [M+H]+ 645.

Step B

N-{3-[2-(2-Amino-1-phenyl-ethylamino)-pyrimidin-4-yl]-1H-pyrazolo[3,4-d]pyrimidin-6-yl}-cyclohexane-1,4-diamine; hydrochloride

To a solution of (4-{3-[2-(2-tert-butoxycarbonylamino-1-phenyl-ethylamino)-pyrimidin-4-yl]-1H-pyrazolo[3,4-d]pyrimidin-6-ylamino}-cyclohexyl)-carbamic acid tert-butyl ester (35 mg, 0.05 mmol) in methanol (30 mL) was bubbled in HCl (gas) for 3 hours at room temperature. The mixture was then concentrated by evaporation to afford N-{3-[2-(2-amino-1-phenyl-ethylamino)-pyrimidin-4-yl]-1H-pyrazolo[3,4-d]pyrimidin-6-yl}-cyclohexane-1,4-diamine; hydrochloride. (Yield 23 mg, 83%).

$^1$H NMR (300 MHz, CD$_3$OD): δ 9.45 (brs, 1H), 8.54 (brs, 1H), 7.71-7.36 (m, 6H), 6.02 (brs, 1H), 4.17-4.05 (m, 1H), 3.68-3.57 (m, 2H), 3.24 (brs, 1H), 3.23-3.20 (m, 4H), 1.64 (brs, 4H). LC-MS: [M+H]+ 445.

Example 68

N-{3-[2-(3-Amino-1-phenyl-propylamino)-pyrimidin-4-yl]-1H-pyrazolo[3,4-d]pyrimidin-6-yl}-cyclohexane-1,4-diamine; hydrochloride

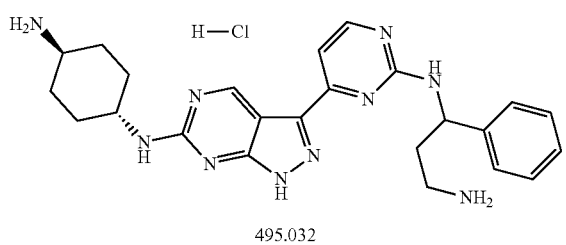 [SMILES: NCCC(Nc1nccc(-c2n[nH]c3nc(N[C@H]4CC[C@H](N)CC4)ncc23)n1)c1ccccc1 ; Cl]

495.032

Step A (4-{3-[2-(3-tert-Butoxycarbonylamino-1-phenyl-propylamino)-pyrimidin-4-yl]-1H-pyrazolo[3,4-d]pyrimidin-6-ylamino}-cyclohexyl)-carbamic acid tert-butyl ester

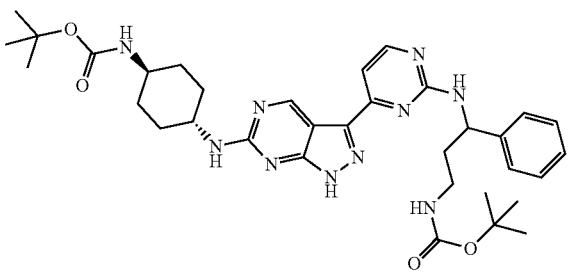 [SMILES: CC(C)(C)OC(=O)NCCC(Nc1nccc(-c2n[nH]c3nc(N[C@H]4CC[C@H](NC(=O)OC(C)(C)C)CC4)ncc23)n1)c1ccccc1]

The mixture of {4-[3-(2-methanesulfinyl-pyrimidin-4-yl)-1H-pyrazolo[3,4-d]pyrimidin-6-ylamino]-cyclohexyl}-carbamic acid tert-butyl ester (from Example 9 supra) (300 mg, 0.64 mmol) and (3-amino-3-phenyl-propyl)-carbamic acid tert-butyl ester (from Example 2 supra) (635 mg, 2.6 mmol) was heated at 140° C. with stirring for 2 hours. The resulting oil was purified by chromatography (silica gel, dichloromethane:methanol, 50:1) and then further purified by prep-HPLC to afford (4-{3-[2-(3-tert-butoxycarbonylamino-1-phenyl-propylamino)-pyrimidin-4-yl]-1H-pyrazolo[3,4-d]pyrimidin-6-ylamino}-cyclohexyl)-carbamic acid tert-butyl ester (30 mg, 7.1%).

LC-MS: [M+H]+ 659.

Step B

N-{3-[2-(3-Amino-1-phenyl-propylamino)-pyrimidin-4-yl]-1H-pyrazolo[3,4-d]pyrimidin-6-yl}-cyclohexane-1,4-diamine; hydrochloride

To a solution of (4-{3-[2-(3-tert-butoxycarbonylamino-1-phenyl-propylamino)-pyrimidin-4-yl]-1H-pyrazolo[3,4-d]pyrimidin-6-ylamino}-cyclohexyl)-carbamic acid tert-butyl ester (30 mg, 0.045 mmol) in methanol (30 mL) was bubbled in HCl (gas) for 3 hours at room temperature. The mixture was then concentrated by evaporation to afford N-{3-[2-(3-amino-1-phenyl-propylamino)-pyrimidin-4-yl]-1H-pyrazolo[3,4-d]pyrimidin-6-yl}-cyclohexane-1,4-diamine; hydrochloride. (Yield 17 mg, 65.8%).

$^1$H NMR (300 MHz, CD$_3$OD): δ 9.25 (brs, 1H), 8.51 (brs, 1H), 7.72-7.64 (m, 3H), 7.48-7.34 (m, 3H), 5.50 (brs, 1H), 4.05 (brs, 1H), 3.32-3.14 (m, 3H), 2.50-2.19 (m, 6H), 1.64 (brs, 4H). LC-MS: [M+H]$^+$ 459.

Example 69

N-{3-[6-(3-Amino-1-phenyl-propylamino)-pyridin-2-yl]-1H-pyrazolo[3,4-d]pyrimidin-6-yl}-cyclohexane-1,4-diamine; hydrochloride

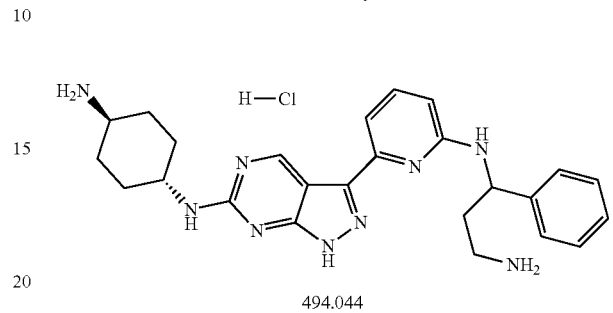

494.044

Step A

{-4-[3-[6-(3-tert-Butoxycarbonylamino-1-phenyl-propylamino)-pyridin-2-yl]-1-(2-trimethylsilanyl-ethoxymethyl)-1H-pyrazolo[3,4-d]pyrimidin-6-ylamino]-cyclohexyl}-carbamic acid tert-butyl ester

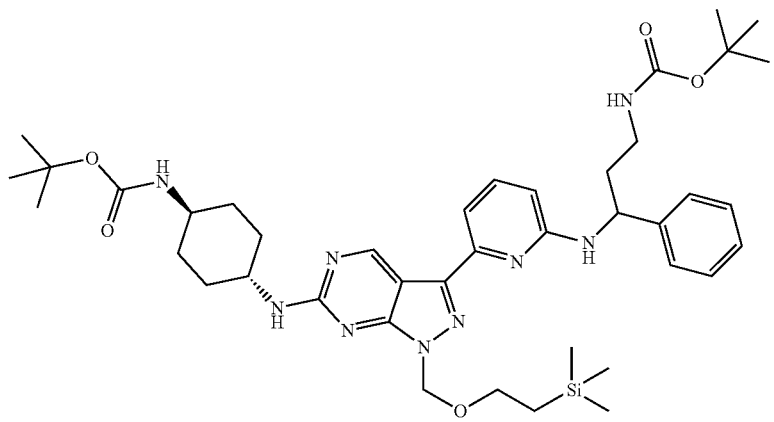 [SMILES: CC(C)(C)OC(=O)NCCC(Nc1cccc(-c2nn(COCC[Si](C)(C)C)c3nc(N[C@H]4CC[C@H](NC(=O)OC(C)(C)C)CC4)ncc23)n1)c1ccccc1]

A sealed tube was charged with {4-[3-(6-bromo-pyridin-2-yl)-1-(2-trimethylsilanyl-ethoxymethyl)-1H-pyrazolo[3,4-d]pyrimidin-6-ylamino]-cyclohexyl}-carbamic acid tert-butyl ester (from Example 33 supra) (618 mg, 1.0 mmol), (3-amino-3-phenyl-propyl)-carbamic acid tert-butyl ester (from Example 2 supra) (300 mg, 1.2 mmol), DavePhos (78 mg, 0.20 mmol), K$_2$CO$_3$ (166 mg, 1.2 mmol), Pd$_2$(dba)$_3$ (44 mg, 0.05 mmol) and 1,4-dioxane (20 mL). The mixture was stirred at 130° C. for 8 hours under an atmosphere of N$_2$. The mixture was cooled and filtered. The filtrate was evaporated under reduced pressure and the residue was purified first by column chromatography (ethyl acetate:petroleum ether, 1:3), then by prep-HPLC to give {4-[3-[6-(3-tert-butoxycarbonylamino-1-phenyl-propylamino)-pyridin-2-yl]-1-(2-trimethylsilanyl-ethoxymethyl)-1H-pyrazolo[3,4-d]pyrimidin-6-ylamino]-cyclohexyl}-carbamic acid tert-butyl ester. (Yield 71 mg, 9.0%)

LC-MS: [M+H]$^+$ 788. .

Step B

N-{3-[6-(3-Amino-1-phenyl-propylamino)-pyridin-2-yl]-1H-pyrazolo[3,4-d]pyrimidin-6-yl}-cyclohexane-1,4-diamine; hydrochloride

To a mixture of {4-[3-[6-(3-tert-butoxycarbonylamino-1-phenyl-propylamino)-pyridin-2-yl]-1-(2-trimethylsilanyl-ethoxymethyl)-1H-pyrazolo[3,4-d]pyrimidin-6-ylamino]-cyclohexyl}-carbamic acid tert-butyl ester (71 mg, 0.09 mmol) in dichloromethane (2 mL) was added CF$_3$COOH (2.2 mL). This mixture was stirred at room temperature for 4 hours. The solvent was then removed under reduced pressure. A saturated aqueous solution of NaHCO$_3$ was added to the residue, and then extracted with ethyl acetate (3×15 mL). The combined organic phase was dried over anhydrous Na$_2$SO$_4$, filtered and concentrated under reduced pressure. The residue was purified by prep-TLC to give product which was treated with conc. HCl acid to give N-{3-[6-(3-amino-1-phenyl-propylamino)-pyridin-2-yl]-1H-pyrazolo[3,4-d]pyrimidin-6-yl}-cyclohexane-1,4-diamine; hydrochloride as a yellow solid. (Yield 22 mg, 53.3%).

$^1$H NMR (300 MHz, CD$_3$OD): δ 9.17 (s, 1H), 7.53-7.45 (m, 4H), 7.37-7.21 (m, 3H), 6.65 (d, 1H, J=9.9 Hz), 5.26-5.23 (m, 1H), 3.90-3.80 (m, 1H), 3.19-3.05 (m, 3H), 2.25-2.05 (m, 6H), 1.63-1.46 (m, 4H). LC-MS: [M+H]$^+$ 458; [M−H]$^+$ 456.

Example 70

N-[3-(2-Benzylamino-pyrimidin-4-yl)-1H-pyrazolo[3,4-d]pyrimidin-6-yl]-cyclohexane-1,4-diamine; hydrochloride

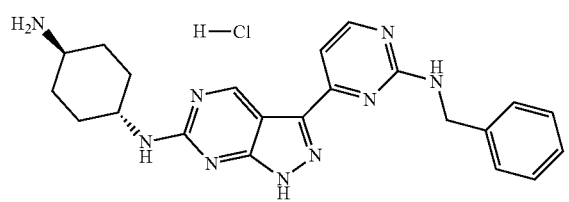 [SMILES: N[C@H]1CC[C@H](Nc2ncc3c(-c4ccnc(NCc5ccccc5)n4)n[nH]c3n2)CC1 ; Cl]

451.963

Step A

{4-[3-(2-Benzylamino-pyrimidin-4-yl)-1H-pyrazolo[3,4-d]pyrimidin-6-ylamino]-cyclohexyl}-carbamic acid tert-butyl ester

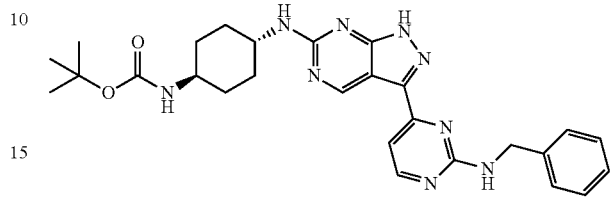

The mixture of {4-[3-(2-methanesulfinyl-pyrimidin-4-yl)-1H-pyrazolo[3,4-d]pyrimidin-6-ylamino]-cyclohexyl}-carbamic acid tert-butyl ester (from Example 9 supra) (150 mg, 0.32 mmol) and benzylamine (138 mg, 1.3 mmol) was heated at 130° C., with stirring for 2 hours. The residue was purified by chromatography (silica gel, 6 g, 200-300 mesh, eluting with dichloromethane:methanol, 50:1 to 30:1) and then further purified by prep-HPLC to afford {4-[3-(2-benzylamino-pyrimidin-4-yl)-1H-pyrazolo[3,4-d]pyrimidin-6-ylamino]-cyclohexyl}-carbamic acid tert-butyl ester. (Yield 30 mg, 18.4%).

LC-MS: [M+H]$^+$ 516.

Step B

N-[3-(2-Benzylamino-pyrimidin-4-yl)-1H-pyrazolo[3,4-d]pyrimidin-6-yl]-cyclohexane-1,4-diamine; hydrochloride

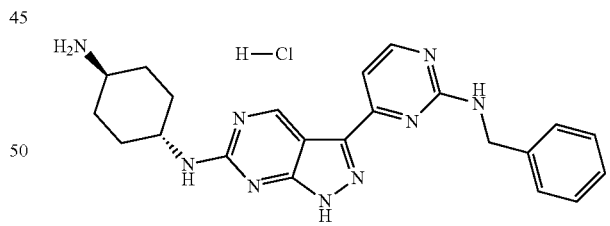

To a solution of {4-[3-(2-benzylamino-pyrimidin-4-yl)-1H-pyrazolo[3,4-d]pyrimidin-6-ylamino]-cyclohexyl}-carbamic acid tert-butyl ester (22 mg, 0.043 mmol) in methanol (30 mL) was bubbled in HCl (gas) for 3 hours at room temperature. The mixture was then concentrated by evaporation to afford N-[3-(2-benzylamino-pyrimidin-4-yl)-1H-pyrazolo[3,4-d]pyrimidin-6-yl]-cyclohexane-1,4-diamine; hydrochloride. (Yield 20 mg, 90.9%).

$^1$H NMR (300 MHz, CD$_3$OD): δ 9.09 (s, 1H), 8.45 (s, 1H), 7.74-7.51 (m, 1H), 7.49-7.36 (m, 5H), 4.96-4.83 (m, 2H), 4.00 (brs, 1H), 3.26-3.20 (m, 1H), 2.28-2.16 (m, 4H), 1.60 (brs, 4H). LC-MS: [M+H]$^+$ 416.

Example 71

N-{3-[2-(3-Chloro-benzylamino)-pyrimidin-4-yl]-1H-pyrazolo[3,4-d]pyrimidin-6-yl}-cyclohexane-1,4-diamine; hydrochloride

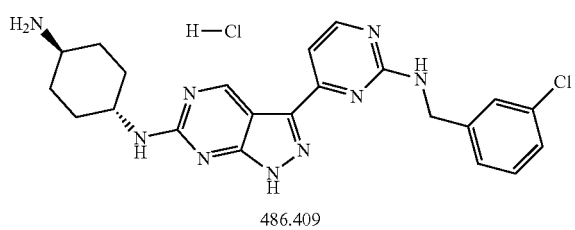 [SMILES: N[C@H]1CC[C@H](Nc2ncc3c(-c4ccnc(NCc5cccc(Cl)c5)n4)n[nH]c3n2)CC1 ; Cl]

486.409

Step A (4-{3-[2-(3-Chloro-benzylamino)-pyrimidin-4-yl]-1H-pyrazolo[3,4-d]pyrimidin-6-ylamino}-cyclohexyl)-carbamic acid tert-butyl ester

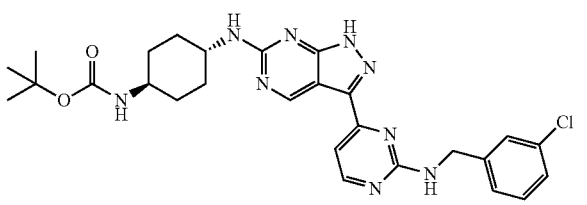 [SMILES: CC(C)(C)OC(=O)N[C@H]1CC[C@H](Nc2ncc3c(-c4ccnc(NCc5cccc(Cl)c5)n4)n[nH]c3n2)CC1]

The mixture of {4-[3-(2-methanesulfinyl-pyrimidin-4-yl)-1H-pyrazolo[3,4-d]pyrimidin-6-ylamino]-cyclohexyl}-carbamic acid tert-butyl ester (from Example 9 supra) (200 mg, 0.42 mmol) and 3-chlorobenzylamine (238 mg, 1.7 mmol) was heated at 130° C., with stirring for 2 hours. The oil obtained was purified by chromatography (silica gel, 6 g, 200-300 mesh, eluting with dichloromethane:methanol, 50:1 to 30:1) and then further purified by prep-HPLC to afford (4-{3-[2-(3-chloro-benzylamino)-pyrimidin-4-yl]-1H-pyrazolo[3,4-d]pyrimidin-6-ylamino}-cyclohexyl)-carbamic acid tert-butyl ester. (Yield 38 mg, 16.4%).

LC-MS: [M+H]$^+$ 550.

Step B

N-{3-[2-(3-Chloro-benzylamino)-pyrimidin-4-yl]-1H-pyrazolo[3,4-d]pyrimidin-6-yl}-cyclohexane-1,4-diamine; hydrochloride

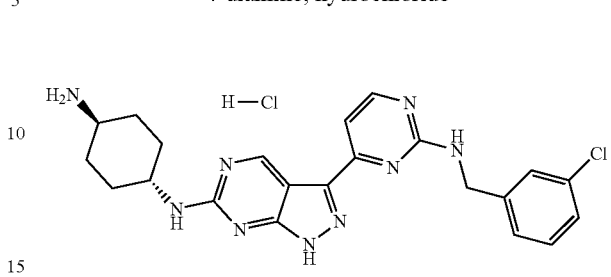

To a solution of (4-{3-[2-(3-chloro-benzylamino)-pyrimidin-4-yl]-1H-pyrazolo[3,4-d]pyrimidin-6-ylamino}-cyclohexyl)-carbamic acid tert-butyl ester (30 mg, 0.0548 mmol) in methanol (30 mL) was bubbled in HCl (gas) for 3 hours at room temperature. The mixture was concentrated by evaporation to afford N-{3-[2-(3-chloro-benzylamino)-pyrimidin-4-yl]-1H-pyrazolo[3,4-d]pyrimidin-6-yl}-cyclohexane-1,4-diamine; hydrochloride. (Yield 29 mg, 98.0%).

$^1$H NMR (300 MHz, CD$_3$OD): δ 9.20 (brs, 1H), 8.45 (brs, 1H), 7.73 (brs, 1H), 7.51-7.35 (m, 4H), 4.98-4.84 (m, 2H), 4.01 (brs, 1H), 3.20 (brs, 1H), 2.41-2.10 (m, 4H), 1.61 (brs, 4H). LC-MS: [M+H]$^+$ 452; [M−H]$^+$ 450.

Example 72

N-{3-[2-(4-Chloro-benzylamino)-pyrimidin-4-yl]-1H-pyrazolo[3,4-d]pyrimidin-6-yl}-cyclohexane-1,4-diamine; hydrochloride

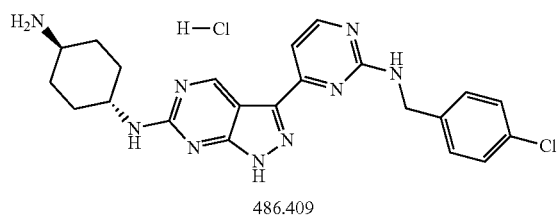 [SMILES: N[C@H]1CC[C@H](Nc2ncc3c(-c4ccnc(NCc5ccc(Cl)cc5)n4)n[nH]c3n2)CC1 ; Cl]

486.409

Step A (4-{3-[2-(4-Chloro-benzylamino)-pyrimidin-4-yl]-1H-pyrazolo[3,4-d]pyrimidin-6-ylamino}-cyclohexyl)-carbamic acid tert-butyl ester

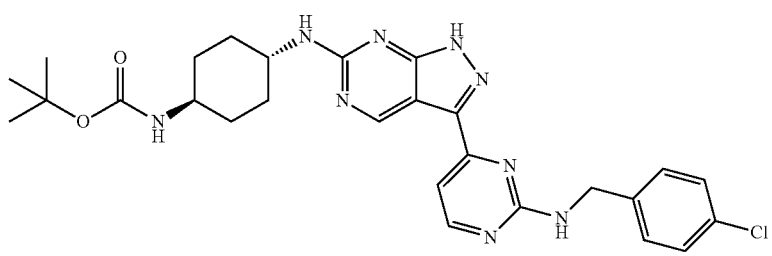 [SMILES: CC(C)(C)OC(=O)N[C@H]1CC[C@H](Nc2ncc3c(-c4ccnc(NCc5ccc(Cl)cc5)n4)n[nH]c3n2)CC1]

The mixture of {4-[3-(2-methanesulfinyl-pyrimidin-4-yl)-1H-pyrazolo[3,4-d]pyrimidin-6-ylamino]-cyclohexyl}-carbamic acid tert-butyl ester (from Example 9 supra) (150 mg, 0.32 mmol) and 4-chlorobenzylamine (179 mg, 1.3 mmol) was heated at 130° C. with stirring for 2 hours. The resulting oil was purified by chromatography (silica gel, 6 g, 200-300 mesh, eluting with dichloromethane:methanol, 50:1 to 30:1) and then further purified by prep-HPLC to afford (4-{3-[2-(4-chloro-benzylamino)-pyrimidin-4-yl]-1H-pyrazolo[3,4-d]pyrimidin-6-ylamino}-cyclohexyl)-carbamic acid tert-butyl ester. (Yield 35 mg, 20.1%).

LC-MS: [M+H]+ 550.

Step B

N-{3-[2-(4-Chloro-benzylamino)-pyrimidin-4-yl]-1H-pyrazolo[3,4-d]pyrimidin-6-yl}-cyclohexane-1,4-diamine; hydrochloride

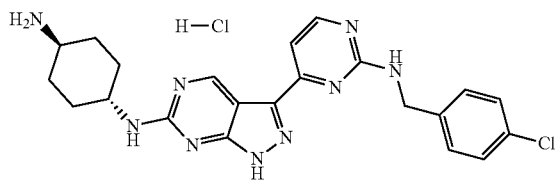 [SMILES: N[C@H]1CC[C@H](Nc2ncc3c(-c4ccnc(NCc5ccc(Cl)cc5)n4)n[nH]c3n2)CC1 ; Cl]

To a solution of (4-{3-[2-(4-chloro-benzylamino)-pyrimidin-4-yl]-1H-pyrazolo[3,4-d]pyrimidin-6-ylamino}-cyclohexyl)-carbamic acid tert-butyl ester (19 mg, 0.034 mmol) in methanol (30 mL) was bubbled in HCl (gas) for 3 hours at room temperature. The mixture was then concentrated by evaporation to afford N-{3-[2-(4-chloro-benzylamino)-pyrimidin-4-yl]-1H-pyrazolo[3,4-d]pyrimidin-6-yl}-cyclohexane-1,4-diamine; hydrochloride. (Yield 15 mg, 78.9%).

$^1$H NMR (300 MHz, CD$_3$OD): δ 9.12 (brs, 1H), 8.47 (s, 1H), 7.74 (d, 1H, J=6.0 Hz), 7.51-7.42 (m, 4H), 4.97-4.83 (m, 2H), 4.01 (brs, 1H), 3.21 (brs, 1H), 2.28-2.16 (m, 4H), 1.64-1.32 (m, 4H). LC-MS: [M+H]+ 451.

Example 73

N1-{3-[6-(2-Morpholin-4-yl-ethylamino)-1H-pyrazolo[3,4-d]pyrimidin-3-yl]-phenyl}-1-phenyl-propane-1,3-diamine; hydrochloride

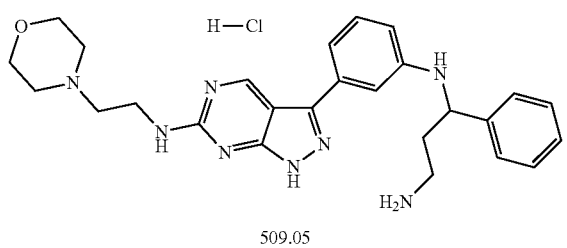 [SMILES: NCCC(Nc1cccc(-c2n[nH]c3nc(NCCN4CCOCC4)ncc23)c1)c1ccccc1 ; Cl]

509.05

Step A (3-{3-[6-(2-Morpholin-4-yl-ethylamino)-1-(2-trimethylsilanyl-ethoxymethyl)-1H-pyrazolo[3,4-d]pyrimidin-3-yl]-phenylamino}-3-phenyl-propyl)-carbamic acid tert-butyl ester

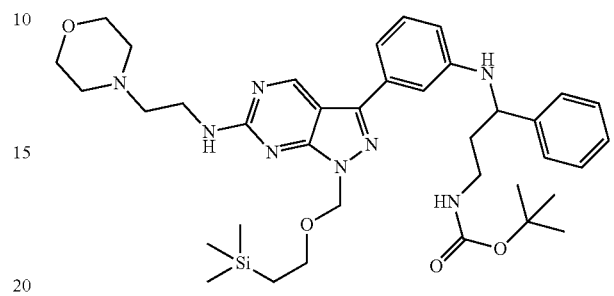

A sealed tube was charged with [3-(3-bromo-phenyl)-1-(2-trimethylsilanyl-ethoxymethyl)-1H-pyrazolo[3,4-d]pyrimidin-6-yl]-(2-morpholin-4-yl-ethyl)-amine (from Example 40 supra) (430 mg, 0.81 mmol), (3-amino-3-phenyl-propyl)-carbamic acid tert-butyl ester (from Example 2 supra) (300 mg, 1.13 mmol), DavePhos (63 mg, 0.16 mmol), K$_2$CO$_3$ (120 mg, 1.13 mmol), Pd$_2$(dba)$_3$ (37 mg, 0.04 mmol) and 1,4-dioxane (16 mL). This mixture was stirred at 140° C. for 15 hours under an atmosphere of N$_2$. The mixture was cooled and filtered; the filtrate was evaporated under reduced pressure to give the crude product. It was purified by chromatography (silica gel, 200-300 mesh, dichloromethane:MeOH, 150:1 to 50:1) to give crude (3-{3-[6-(2-morpholin-4-yl-ethylamino)-1-(2-trimethylsilanyl-ethoxymethyl)-1H-pyrazolo[3,4-d]pyrimidin-3-yl]-phenylamino}-3-phenyl-propyl)-carbamic acid tert-butyl ester. (Yield 329 mg).

LC-MS: [M+H]+ 703.

Step B

N1-{3-[6-(2-Morpholin-4-yl-ethylamino)-1H-pyrazolo[3,4-d]pyrimidin-3-yl]-phenyl}-1-phenyl-propane-1,3-diamine; hydrochloride

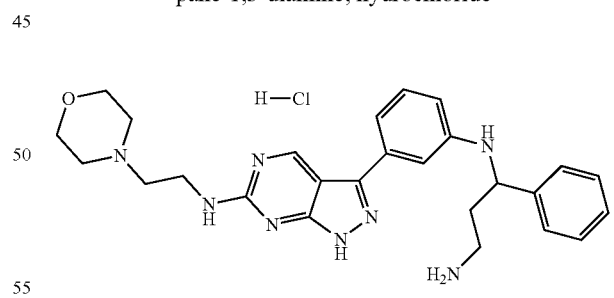

To a stirred solution of crude (3-{3-[6-(2-morpholin-4-yl-ethylamino)-1-(2-trimethylsilanyl-ethoxymethyl)-1H-pyrazolo[3,4-d]pyrimidin-3-yl]-phenylamino}-3-phenyl-propyl)-carbamic acid tert-butyl ester (329 mg, crude) in dichloromethane (1.5 mL) was added TFA (1.5 mL) at room temperature. The resulting mixture was stirred for 2 hours at room temperature. The reaction solution was concentrated under reduced pressure and partitioned between saturated NaHCO$_3$ solution and ethyl acetate. The water phase was extracted with ethyl acetate again. The combined organic phase was dried over anhydrous Na$_2$SO$_4$, filtered and concentrated. The residue was purified by column chromatography (silica gel, MeOH:dichloromethane, 1:100 to 1:10). The obtained solid was dissolved in a solution of HCl in MeOH and concentrated to give N1-{3-[6-(2-morpholin-4-yl-ethylamino)-1H-pyrazolo[3,4-d]pyrimidin-3-yl]-phenyl}-1-phenyl-propane-1,3-diamine; hydrochloride. (Yield 20 mg).

$^{1}$H NMR (300 MHz, CD$_{3}$OD): δ 9.31 (brs, 1H), 7.56-7.39 (m, 9H), 4.43 (brs, 1H), 4.11-3.95 (m, 5H), 3.78-3.74 (m, 2H), 3.58-3.56 (m, 2H), 3.15-2.96 (m, 4H), 2.53 (brs, 2H). LC-MS: [M+H]$^{+}$ 473; [M–H]$^{+}$ 471.

Example 74

N-{3-[6-(2-Amino-1-phenyl-ethylamino)-pyridin-2-yl]-1H-pyrazolo[3,4-d]pyrimidin-6-yl}-cyclohexane-1,4-diamine; hydrochloride

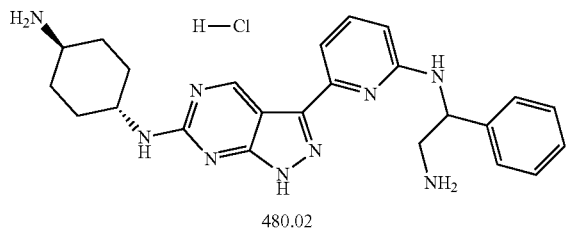 [SMILES: NCC(Nc1cccc(-c2n[nH]c3nc(N[C@H]4CC[C@H](N)CC4)ncc23)n1)c1ccccc1 ; Cl]

480.02

Step A (4-{3-[6-(2-tert-Butoxycarbonylamino-1-phenyl-ethylamino)-pyridin-2-yl]-1-trityl-1H-pyrazolo[3,4-d]pyrimidin-6-ylamino}-cyclohexyl)-carbamic acid tert-butyl ester

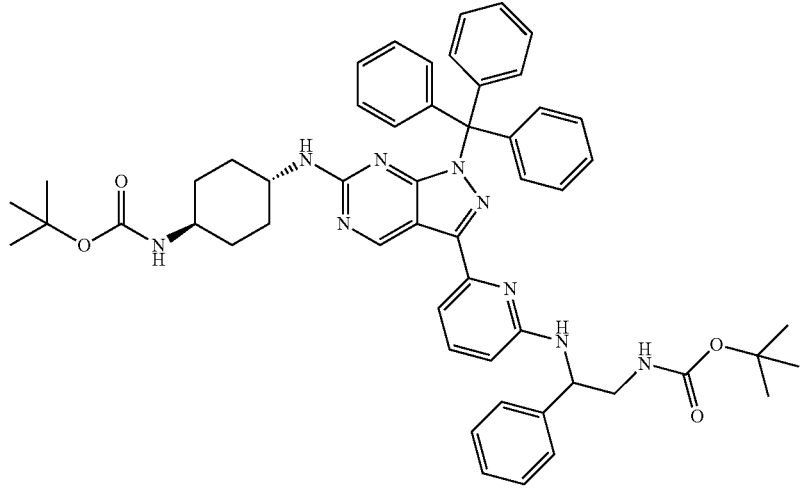 [SMILES: CC(C)(C)OC(=O)NCC(Nc1cccc(-c2nn(C(c3ccccc3)(c3ccccc3)c3ccccc3)c3nc(N[C@H]4CC[C@H](NC(=O)OC(C)(C)C)CC4)ncc23)n1)c1ccccc1]

A sealed tube was charged with {4-[3-(6-bromo-pyridin-2-yl)-1-trityl-1H-pyrazolo[3,4-d]pyrimidin-6-ylamino]-cyclohexyl}-carbamic acid tert-butyl ester (from Example 35 supra) (860 mg, 1.18 mmol), (2-amino-2-phenyl-ethyl)-carbamic acid tert-butyl ester (from Example 1 supra) (390 mg, 1.65 mmol), Pd$_{2}$(dba)$_{3}$ (68 mg, 0.12 mmol), DavePhos (93 mg, 0.24 mmol), K$_{2}$CO$_{3}$ (228 mg, 1.65 mmol) and dioxane (30 mL), this mixture was stirred at 132° C. under an atmosphere of N$_{2}$ for 7 hours. After cooling to room temperature, the mixture was filtered and concentrated under reduced pressure. The residue was purified by column chromatography (silica gel, 26 g, 100-200 mesh, eluting with petroleum ether:ethyl acetate, 1:1) to give crude product which was further purified by prep-HPLC to afford (4-{3-[6-(2-tert-Butoxycarbonylamino-1-phenyl-ethylamino)-pyridin-2-yl]-1-trityl-1H-pyrazolo[3,4-d]pyrimidin-6-ylamino}-cyclohexyl)-carbamic acid tert-butyl ester. (Yield 103 mg, 9.86%).

LC-MS: [M+H]$^{+}$ 886.

Step B

N-{3-[6-(2-Amino-1-phenyl-ethylamino)-pyridin-2-yl]-1H-pyrazolo[3,4-d]pyrimidin-6-yl}-cyclohexane-1,4-diamine; hydrochloride

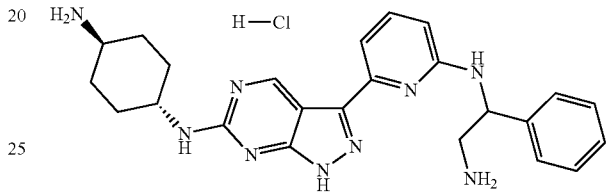

To a mixture of (4-{3-[6-(2-tert-Butoxycarbonylamino-1-phenyl-ethylamino)-pyridin-2-yl]-1-trityl-1H-pyrazolo[3,4-d]pyrimidin-6-ylamino}-cyclohexyl)-carbamic acid tert-butyl ester (103 mg, 0.116 mmol) in C$_{2}$H$_{5}$OH (8 mL) was added conc. HCl (8 mL) at room temperature. The mixture was stirred at room temperature for 15 hour. The solvent was removed under reduced pressure. The residue was washed with dichloromethane (10 mL) to get the crude compound which was purified by prep-HPLC to give N-{3-[6-(2-amino-1-phenyl-ethylamino)-pyridin-2-yl]-1H-pyrazolo[3,4-d]pyrimidin-6-yl}-cyclohexane-1,4-diamine; hydrochloride as a yellow solid. (Yield 14 mg).

$^{1}$H NMR (300 MHz, CD$_{3}$OD): δ 9.25 (brs, 1H), 7.60-7.18 (m, 7H), 6.78 (d, 1H, J=8.1 Hz), 5.39-5.36 (m, 1H), 3.90 (brs, 1H), 3.31-3.27 (m, 2H), 3.12 (brs, 1H), 2.23-2.06 (m, 4H), 1.50 (brs, 4H). LC-MS: [M+H]$^{+}$ 444; [M–H]$^{+}$ 442.

Example 75

N1-{6-[6-(2-Morpholin-4-yl-ethylamino)-1H-pyrazolo[3,4-d]pyrimidin-3-yl]-pyridin-2-yl}-1-phenyl-propane-1,3-diamine; hydrochloride

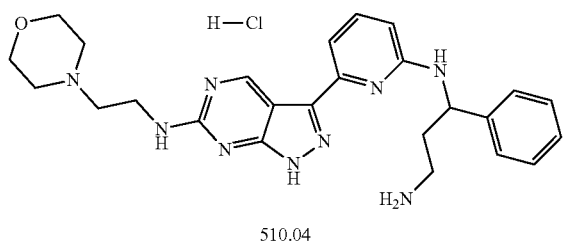 [SMILES: NCCC(Nc1cccc(-c2n[nH]c3nc(NCCN4CCOCC4)ncc23)n1)c1ccccc1 ; Cl]

510.04

Step A (3-{6-[6-(2-Morpholin-4-yl-ethylamino)-1-(2-trimethylsilanyl-ethoxymethyl)-1H-pyrazolo[3,4-d]pyrimidin-3-yl]-pyridin-2-ylamino}-3-phenyl-propyl)-carbamic acid tert-butyl ester

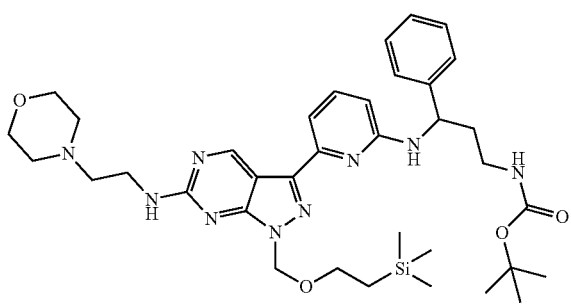 [SMILES: CC(C)(C)OC(=O)NCCC(Nc1cccc(-c2nn(COCC[Si](C)(C)C)c3nc(NCCN4CCOCC4)ncc23)n1)c1ccccc1]

A sealed tube was charged with [3-(6-bromo-pyridin-2-yl)-1-(2-trimethylsilanyl-ethoxymethyl)-1H-pyrazolo[3,4-d]pyrimidin-6-yl]-(2-morpholin-4-yl-ethyl)-amine (from Example 32 supra) (500 mg, 0.936 mmol), (3-amino-3-phenyl-propyl)-carbamic acid tert-butyl ester (from Example 2 supra) (328 mg, 1.31 mmol), Pd$_2$(dba)$_3$ (54 mg, 0.094 mmol), DavePhos (74 mg, 0.187 mmol), K$_2$CO$_3$ (181 mg, 1.31 mmol) and dioxane (20 mL). The mixture was stirred at 132° C. under an atmosphere of N$_2$ for 7.5 hours. After cooling to room temperature, the mixture was filtered and concentrated under reduced pressure. The residue was purified by column chromatography (silica gel, 14 g, 100-200 mesh, eluting with dichloromethane:MeOH, 80:1) to give crude product which was further purified by prep-HPLC to afford (3-{6-[6-(2-morpholin-4-yl-ethylamino)-1-(2-trimethylsilanyl-ethoxymethyl)-1H-pyrazolo[3,4-d]pyrimidin-3-yl]-pyridin-2-ylamino}-3-phenyl-propyl)-carbamic acid tert-butyl ester. (Yield 147 mg, 16%).

Step B

N1-{6-[6-(2-Morpholin-4-yl-ethylamino)-1H-pyrazolo[3,4-d]pyrimidin-3-yl]-pyridin-2-yl}-1-phenyl-propane-1,3-diamine; hydrochloride

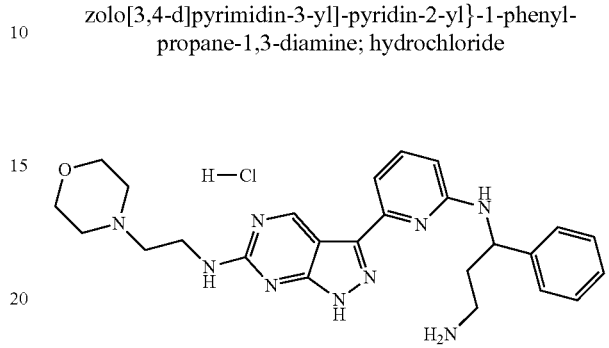

(3-{6-[6-(2-Morpholin-4-yl-ethylamino)-1-(2-trimethylsilanyl-ethoxymethyl)-1H-pyrazolo[3,4-d]pyrimidin-3-yl]-pyridin-2-ylamino}-3-phenyl-propyl)-carbamic acid tert-butyl ester (147 mg, 0.209 mmol) was dissolved in CF$_3$COOH (4 mL). The mixture was heated at reflux for 15 hours. The solvent was removed under reduced pressure. A saturated aqueous solution of NaHCO$_3$ was added to the residue, and then extracted with ethyl acetate (3×15 mL). The combined organic phase was dried over anhydrous Na$_2$SO$_4$, filtered and concentrated under reduced pressure. After purification by prep-HPLC, concentrated HCl was added to the fractions with product and concentrated under reduced pressure to give N1-{6-[6-(2-Morpholin-4-yl-ethylamino)-1H-pyrazolo[3,4-d]pyrimidin-3-yl]-pyridin-2-yl}-1-phenyl-propane-1,3-diamine; hydrochloride as a yellow solid. (Yield 16 mg, 16.2%).

$^1$H NMR (300 MHz, CD$_3$OD): δ 9.48 (s, 1H), 8.06-8.02 (m, 1H), 7.65-7.37 (m, 6H), 7.11 (d, 1H, J=9.3 Hz), 5.14-5.10 (m, 1H), 4.11-3.89 (m, 6H), 3.77-3.73 (m, 2H), 3.57-3.52 (m, 2H), 3.25-3.05 (m, 4H), 2.49-2.32 (m, 2H). LC-MS: [M+H]$^+$ 474.

Example 76

1-(3-Chloro-phenyl)-N1-{4-[6-(2-morpholin-4-yl-ethylamino)-1H-pyrazolo[3,4-d]pyrimidin-3-yl]-pyrimidin-2-yl}-ethane-1,2-diamine; hydrochloride

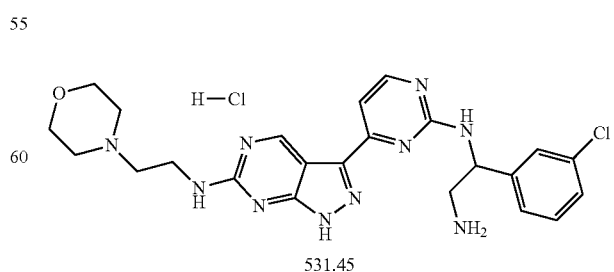

531.45

Step A (2-(3-Chloro-phenyl)-2-{4-[6-(2-morpholin-4-yl-ethylamino)-1H-pyrazolo[3,4-d]pyrimidin-3-yl]-pyrimidin-2-ylamino}-ethyl)-carbamic acid tert-butyl ester

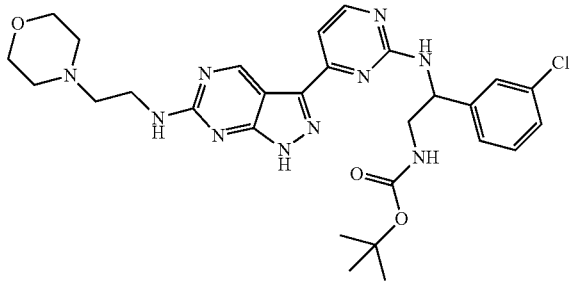 [SMILES: CC(C)(C)OC(=O)NCC(Nc1nccc(-c2n[nH]c3nc(NCCN4CCOCC4)ncc23)n1)c1cccc(Cl)c1]

(2-(3-Chloro-phenyl)-2-{4-[6-(2-morpholin-4-yl-ethylamino)-1H-pyrazolo[3,4-d]pyrimidin-3-yl]-pyrimidin-2-ylamino}-ethyl)-carbamic acid tert-butyl ester was prepared from [3-(2-methanesulfonyl-pyrimidin-4-yl)-1H-pyrazolo[3,4-d]pyrimidin-6-yl]-(2-morpholin-4-yl-ethyl)-amine (from Example 11 supra) and [2-amino-2-(3-chloro-phenyl)-ethyl]-carbamic acid tert-butyl ester (from Example 4 supra) by following the method in Example 61.

Step B 1-(3-Chloro-phenyl)-N1-{4-[6-(2-morpholin-4-yl-ethylamino)-1H-pyrazolo[3,4-d]pyrimidin-3-yl]-pyrimidin-2-yl}-ethane-1,2-diamine; hydrochloride

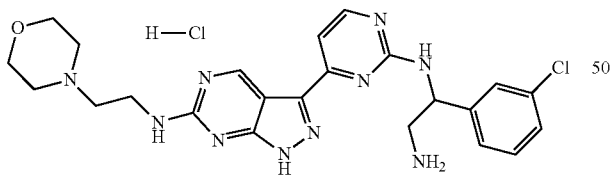

(2-(3-Chloro-phenyl)-2-{4-[6-(2-morpholin-4-yl-ethylamino)-1H-pyrazolo[3,4-d]pyrimidin-3-yl]-pyrimidin-2-ylamino}-ethyl)-carbamic acid tert-butyl ester (100 mg, 0.17 mmol) was dissolved in EtOH (4 mL), then HCl (4 mL) was added. The reaction mixture was stirred at room temperature for 10 hours. The solvent was removed under reduced pressure to afford the crude product which was purified by prep-HPLC to afford 1-(3-chloro-phenyl)-N1-{4-[6-(2-morpholin-4-yl-ethylamino)-1H-pyrazolo[3,4-d]pyrimidin-3-yl]-pyrimidin-2-yl}-ethane-1,2-diamine; hydrochloride. (Yield 24 mg, 23.7%).

$^1$H NMR (300 MHz, CD$_3$OD): δ 9.59 (brs, 1H), 8.53 (brs, 1H), 7.78-7.63 (m, 3H), 7.49-7.38 (m, 2H), 6.12 (brs, 1H), 4.10-3.90 (m, 6H), 3.77-3.55 (m, 6H), 3.29-3.25 (m, 2H). LC-MS: [M+H]$^+$ 496.

Example 77

(2-Morpholin-4-yl-ethyl)-(3-{2-[(thiophen-3-ylmethyl)-amino]-pyrimidin-4-yl}-1H-pyrazolo[3,4-d]pyrimidin-6-yl)-amine; hydrochloride

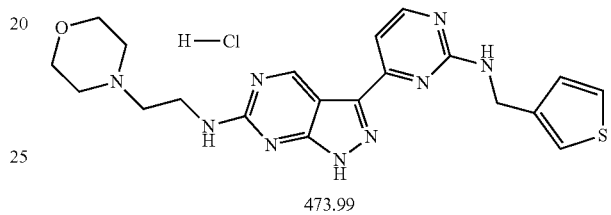

473.99

(2-Morpholin-4-yl-ethyl)-(3-{2-[(thiophen-3-ylmethyl)-amino]-pyrimidin-4-yl}-1H-pyrazolo[3,4-d]pyrimidin-6-yl)-amine; hydrochloride was prepared from [3-(2-methanesulfonyl-pyrimidin-4-yl)-1H-pyrazolo[3,4-d]pyrimidin-6-yl]-(2-morpholin-4-yl-ethyl)-amine (from Example 11 supra) (130 mg, 0.32 mmol) and thiophen-3-yl-methylamine by following the method in Example 61. (Yield 16 mg, 10.5%).

$^1$H NMR (300 MHz, CD$_3$OD): δ 9.19 (brs, 1H), 8.43 (d, 1H, J=6.3 Hz), 7.75 (d, 1H, J=6.6 Hz), 7.53-7.51 (m, 2H), 7.25-7.23 (m, 1H), 4.03-3.87 (m, 6H), 3.75-3.52 (m, 4H), 3.32-3.23 (m, 2H). LC-MS: [M+H]$^+$ 438.

Example 78

N-(3-{2-[2-Amino-1-(3-chloro-phenyl)-ethylamino]-pyrimidin-4-yl}-1H-pyrazolo[3,4-d]pyrimidin-6-yl)-cyclohexane-1,4-diamine; hydrochloride

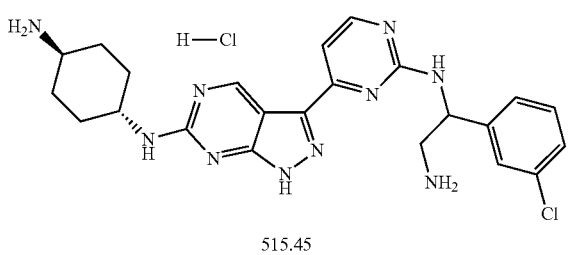

515.45

Step A

[4-(3-{2-[2-tert-Butoxycarbonylamino-1-(3-chloro-phenyl)-ethylamino]-pyrimidin-4-yl}-1H-pyrazolo[3,4-d]pyrimidin-6-ylamino)-cyclohexyl]-carbamic acid tert-butyl ester

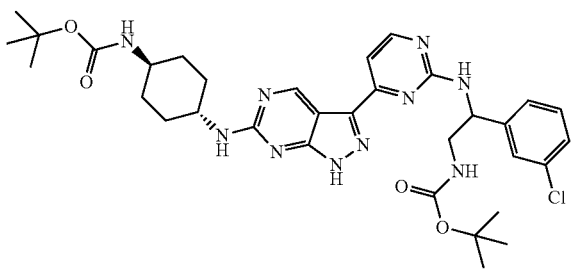 [SMILES: CC(C)(C)OC(=O)NCC(Nc1nccc(-c2n[nH]c3nc(N[C@H]4CC[C@H](NC(=O)OC(C)(C)C)CC4)ncc23)n1)c1cccc(Cl)c1]

The mixture of {4-[3-(2-methanesulfinyl-pyrimidin-4-yl)-1H-pyrazolo[3,4-d]pyrimidin-6-ylamino]-cyclohexyl}-carbamic acid tert-butyl ester (from Example 9 supra) (300 mg, 0.64 mmol) and [2-amino-2-(3-chloro-phenyl)-ethyl]-carbamic acid tert-butyl ester (from Example 4 supra) (686 mg, 2.5 mmol) was heated at 130° C. with stirring for 2 hours. The resulting oil was purified by chromatography (silica gel, 8 g, 200-300 mesh, eluting with dichloromethane:methanol, 50:1 to 30:1) to afford crude [4-(3-{2-[2-tert-butoxycarbonylamino-1-(3-chloro-phenyl)-ethylamino]-pyrimidin-4-yl}-1H-pyrazolo[3,4-d]pyrimidin-6-ylamino)-cyclohexyl]-carbamic acid tert-butyl ester. (Yield 140 mg, 32.5%).
LC-MS: [M+H]$^+$ 679.

Step B

N-(3-{2-[2-Amino-1-(3-chloro-phenyl)-ethylamino]-pyrimidin-4-yl}-1H-pyrazolo[3,4-d]pyrimidin-6-yl)-cyclohexane-1,4-diamine; hydrochloride

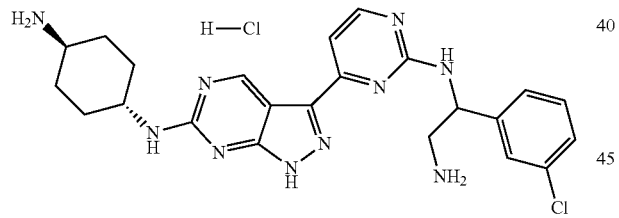

To a solution of crude [4-(3-{2-[2-tert-butoxycarbonylamino-1-(3-chloro-phenyl)-ethylamino]-pyrimidin-4-yl}-1H-pyrazolo[3,4-d]pyrimidin-6-ylamino)-cyclohexyl]-carbamic acid tert-butyl ester (30 mg, 0.044 mmol) in methanol (40 mL) was bubbled in HCl (gas) for 3 hours at room temperature. Then the mixture was concentrated by evaporation to afford N-(3-{2-[2-amino-1-(3-chloro-phenyl)-ethylamino]-pyrimidin-4-yl}-1H-pyrazolo[3,4-d]pyrimidin-6-yl)-cyclohexane-1,4-diamine; hydrochloride. (Yield 24 mg, 93.3%).

$^1$H NMR (300 MHz, CD$_3$OD): δ 9.62 (brs, 1H), 8.57 (brs, 1H), 7.73-7.66 (m, 3H), 7.49-7.38 (m, 2H), 6.15 (brs, 1H), 4.04 (brs, 1H), 3.66-3.59 (m, 2H), 3.03 (brs, 1H), 2.30-2.09 (m, 4H), 1.64 (br s, 4H). LC-MS: [M+H]$^+$ 479; [M−H]$^+$ 477.

Example 79

N-{3-[3-(3-Amino-1-phenyl-propylamino)-phenyl]-1H-pyrazolo[3,4-d]pyrimidin-6-yl}-cyclohexane-1,4-diamine; hydrochloride

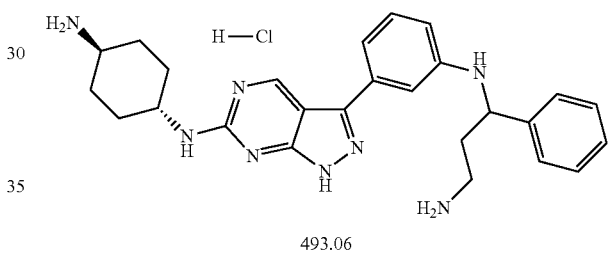

493.06

Step A (4-{3-[3-(3-tert-Butoxycarbonylamino-1-phenyl-propylamino)-phenyl]-1-trityl-1H-pyrazolo[3,4-d]pyrimidin-6-ylamino}-cyclohexyl)-carbamic acid tert-butyl ester

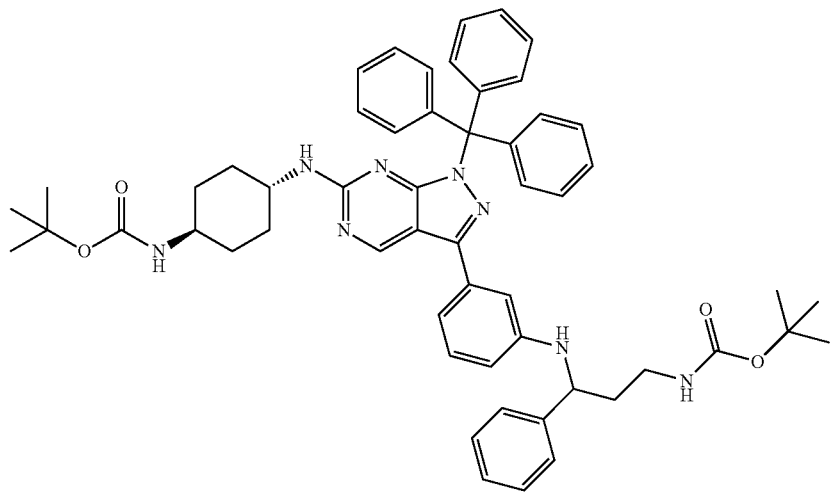 [SMILES: CC(C)(C)OC(=O)NCCC(Nc1cccc(-c2nn(C(c3ccccc3)(c3ccccc3)c3ccccc3)c3nc(N[C@H]4CC[C@H](NC(=O)OC(C)(C)C)CC4)ncc23)c1)c1ccccc1]

A sealed tube was charged with {4-[3-(3-bromo-phenyl)-1-trityl-1H-pyrazolo[3,4-d]pyrimidin-6-ylamino]-cyclohexyl}-carbamic acid tert-butyl ester (from Example 43 supra) (500 mg, 0.686 mmol), (3-amino-3-phenyl-propyl)-carbamic acid tert-butyl ester (from Example 2 supra) (258 mg, 1.03 mmol), DavePhos (54 mg, 0.137 mmol), K$_2$CO$_3$ (142 mg, 1.03 mmol), Pd$_2$(dba)$_3$ (31 mg, 0.0343 mmol) and 1,4-dioxane (14 mL). This mixture was stirred at 120° C. for 15 hours under an atmosphere of N$_2$. The mixture was cooled and filtered; the filtrate was evaporated under reduced pressure to give the crude product. It was purified by chromatography (silica gel, 200-300 mesh, dichloromethane:MeOH, 200:1 to 50:1), then by prep-HPLC to give (4-{3-[3-(3-tert-butoxycarbonylamino-1-phenyl-propylamino)-phenyl]-1-trityl-1H-pyrazolo[3,4-d]pyrimidin-6-ylamino}-cyclohexyl)-carbamic acid tert-butyl ester. (Yield 63 mg, 10.2%).

LC-MS: [M+H]$^+$ 899.

Example 80

N-(3-{2-[3-Amino-1-(3-chloro-phenyl)-propylamino]-pyrimidin-4-yl}-1H-pyrazolo[3,4-d]pyrimidin-6-yl)-cyclohexane-1,4-diamine; hydrochloride

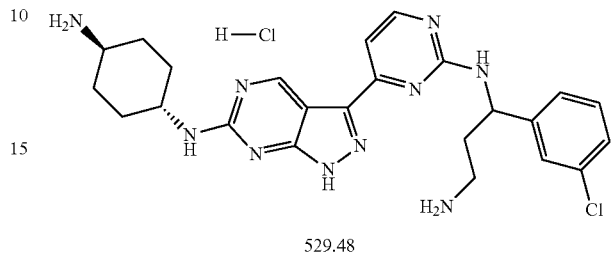

529.48

Step A

[4-(3-{2-[3-tert-Butoxycarbonylamino-1-(3-chloro-phenyl)-propylamino]-pyrimidin-4-yl}-1H-pyrazolo[3,4-d]pyrimidin-6-ylamino)-cyclohexyl]-carbamic acid tert-butyl ester

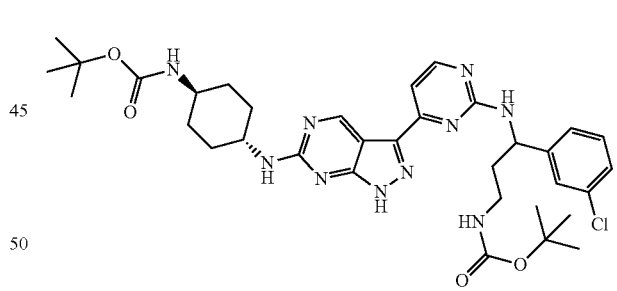

The mixture of {4-[3-(2-methanesulfinyl-pyrimidin-4-yl)-1H-pyrazolo[3,4-d]pyrimidin-6-ylamino]-cyclohexyl}-carbamic acid tert-butyl ester (from Example 9 supra) (300 mg, 0.64 mmol) and [3-amino-3-(3-chloro-phenyl)-propyl]-carbamic acid tert-butyl ester (from Example 3 supra) (722 mg, 2.6 mmol) was heated at 130° C. with stirring for 2 hours. The resulting oil was purified by chromatography (silica gel, 8 g, 200-300 mesh, eluting with dichloromethane:methanol, 50:1 to 30:1) to afford crude [4-(3-{2-[3-tert-butoxycarbonylamino-1-(3-chloro-phenyl)-propylamino]-pyrimidin-4-yl}-1H-pyrazolo[3,4-d]pyrimidin-6-ylamino)-cyclohexyl]-carbamic acid tert-butyl ester. (Yield 135 mg, 30.6%).

LC-MS: [M+H]$^+$ 693.

Step B

N-{3-[3-(3-Amino-1-phenyl-propylamino)-phenyl]-1H-pyrazolo[3,4-d]pyrimidin-6-yl}-cyclohexane-1,4-diamine; hydrochloride

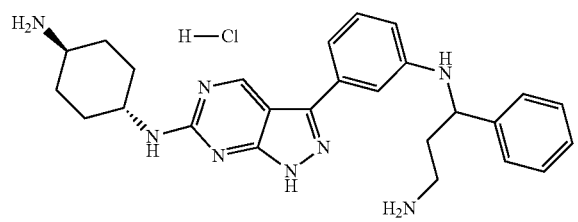

To a stirred solution of (4-{3-[3-(3-tert-butoxycarbonylamino-1-phenyl-propylamino)-phenyl]-1-trityl-1H-pyrazolo[3,4-d]pyrimidin-6-ylamino}-cyclohexyl)-carbamic acid tert-butyl ester (91 mg, 0.10 mmol) in EtOH (2.0 mL) was added conc. HCl (4 mL) at room temperature. The resulting mixture was stirred for 15 hours at room temperature. The reaction solution was concentrated under reduced pressure. The residue was washed with dichloromethane (10 mL), then purified by prep-HPLC to give N-{3-[3-(3-amino-1-phenyl-propylamino)-phenyl]-1H-pyrazolo[3,4-d]pyrimidin-6-yl}-cyclohexane-1,4-diamine; hydrochloride. (Yield 43 mg).

$^1$H NMR (300 MHz, CD$_3$OD): δ 9.23 (s, 1H), 7.77-7.71 (m, 2H), 7.55-7.36 (m, 6H), 7.19 (s, 1H), 5.00 (s, 1H), 4.04 (brs, 1H), 3.23-3.05 (m, 2H), 2.87 (brs, 1H), 2.54 (brs, 2H), 2.29-2.19 (m, 4H), 1.67-1.57 (m, 4H). LC-MS: [M+H]$^+$ 457; [M-H]$^+$ 455.

Step B

N-(3-{2-[3-Amino-1-(3-chloro-phenyl)-propylamino]-pyrimidin-4-yl}-1H-pyrazolo[3,4-d]pyrimidin-6-yl)-cyclohexane-1,4-diamine; hydrochloride

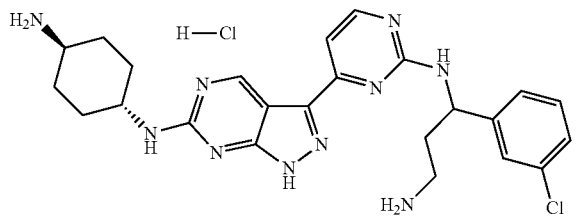

To a solution of crude [4-(3-{2-[3-tert-butoxycarbonylamino-1-(3-chloro-phenyl)-propylamino]-pyrimidin-4-yl}-1H-pyrazolo[3,4-d]pyrimidin-6-ylamino)-cyclohexyl]-carbamic acid tert-butyl ester (21 mg, 0.03 mmol) in methanol (40 mL) was bubbled in HCl (gas) for 3 hours at room temperature. The mixture was then concentrated by evaporation to afford N-(3-{2-[3-amino-1-(3-chloro-phenyl)-propylamino]-pyrimidin-4-yl}-1H-pyrazolo[3,4-d]pyrimidin-6-yl)-cyclohexane-1,4-diamine; hydrochloride. (Yield 20 mg, 93.0%).

$^1$H NMR (300 MHz, CD$_3$OD): δ 9.40 (s, 1H), 8.53-8.39 (m, 1H), 7.76-7.63 (m, 3H), 7.48-7.37 (m, 2H), 5.61 (brs, 1H), 4.05 (brs, 1H), 3.19-3.10 (m, 3H), 2.48-2.19 (m, 6H), 1.64 (brs, 4H). LC-MS: [M+H]$^+$ 493.

Example 81

N1-{4-[6-(2-Morpholin-4-yl-ethylamino)-1H-pyrazolo[3,4-d]pyrimidin-3-yl]-pyrimidin-2-yl}-1-phenyl-propane-1,3-diamine; hydrochloride

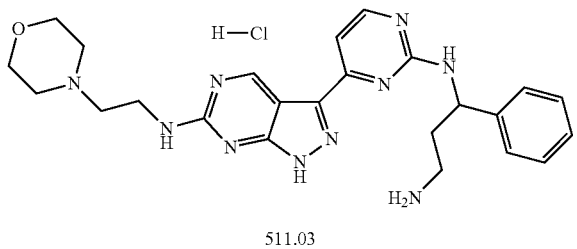

511.03

Step A (3-{4-[6-(2-Morpholin-4-yl-ethylamino)-1H-pyrazolo[3,4-d]pyrimidin-3-yl]-pyrimidin-2-ylamino}-3-phenyl-propyl)-carbamic acid tert-butyl ester

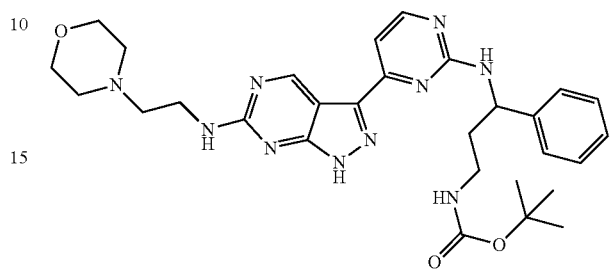

(3-{4-[6-(2-Morpholin-4-yl-ethylamino)-1H-pyrazolo[3,4-d]pyrimidin-3-yl]-pyrimidin-2-ylamino}-3-phenyl-propyl)-carbamic acid tert-butyl ester was prepared from [3-(2-methane sulfonyl-pyrimidin-4-yl)-1H-pyrazolo[3,4-d]pyrimidin-6-yl]-(2-morpholin-4-yl-ethyl)-amine (from Example 11 supra) and (3-amino-3-phenyl-propyl)-carbamic acid tert-butyl ester (from Example 2 supra) by following the method in Example 61.

Step B

N1-{4-[6-(2-Morpholin-4-yl-ethylamino)-1H-pyrazolo[3,4-d]pyrimidin-3-yl]-pyrimidin-2-yl}-1-phenyl-propane-1,3-diamine; hydrochloride (3-{4-[6-(2-Morpholin-4-yl-ethylamino)-1H-pyrazolo[3,4-d]pyrimidin-3-yl]-pyrimidin-2-ylamino}-3-phenyl-propyl)-carbamic acid tert-butyl ester (150 mg, 0.26 mmol) was dissolved in EtOH (4 mL), then conc. HCl (4 mL) was added. The reaction mixture was stirred at room temperature for 16 hours. The solvent was removed under reduced pressure to afford the crude product which was purified by prep-HPLC to afford N1-{4-[6-(2-morpholin-4-yl-ethylamino)-1H-pyrazolo[3,4-d]pyrimidin-3-yl]-pyrimidin-2-yl}-1-phenyl-propane-1,3-diamine; hydrochloride. (Yield 30 mg, 19.5%).

$^1$H NMR (300 MHz, CD$_3$OD): δ 10.10 (s, 1H), 9.28 (s, 1H), 8.51-8.38 (m, 1H), 7.81-7.75 (m, 3H), 7.49-7.35 (m,

3H), 5.63-5.52 (m, 1H), 4.11-3.66 (m, 10H), 3.28-3.09 (m, 4H), 2.50-2.34 (m, 2H). LC-MS: [M+H]⁺ 475, [M−H]⁺ 473.

Example 82

N1-{4-[6-(2-Morpholin-4-yl-ethylamino)-1H-pyrazolo[3,4-d]pyrimidin-3-yl]-pyrimidin-2-yl}-1-thiophen-3-yl-ethane-1,2-diamine; hydrochloride

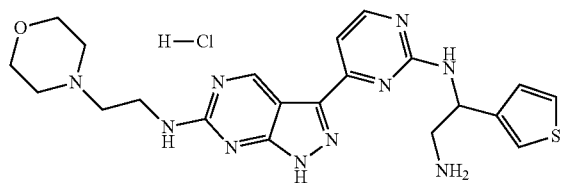

503.03

Step A (2-{4-[6-(2-Morpholin-4-yl-ethylamino)-1H-pyrazolo[3,4-d]pyrimidin-3-yl]-pyrimidin-2-ylamino}-2-thiophen-3-yl-ethyl)-carbamic acid tert-butyl ester

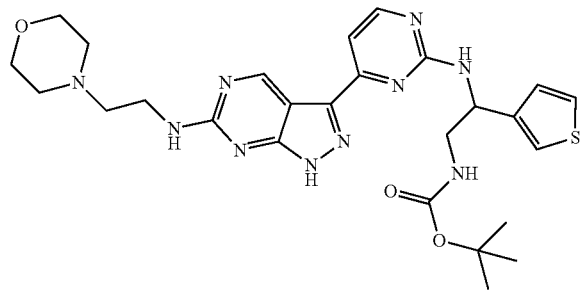 [SMILES: CC(C)(C)OC(=O)NCC(Nc1nccc(-c2n[nH]c3nc(NCCN4CCOCC4)ncc23)n1)c1ccsc1]

(2-{4-[6-(2-Morpholin-4-yl-ethylamino)-1H-pyrazolo[3,4-d]pyrimidin-3-yl]-pyrimidin-2-ylamino}-2-thiophen-3-yl-ethyl)-carbamic acid tert-butyl ester was prepared from [3-(2-methanesulfonyl-pyrimidin-4-yl)-1H-pyrazolo[3,4-d]pyrimidin-6-yl]-(2-morpholin-4-yl-ethyl)-amine (from Example 11 supra) and (2-amino-2-thiophen-3-yl-ethyl)-carbamic acid tert-butyl ester (from Example 6 supra) by following the method in Example 61.

Step B

N1-{4-[6-(2-Morpholin-4-yl-ethylamino)-1H-pyrazolo[3,4-d]pyrimidin-3-yl]-pyrimidin-2-yl}-1-thiophen-3-yl-ethane-1,2-diamine; hydrochloride

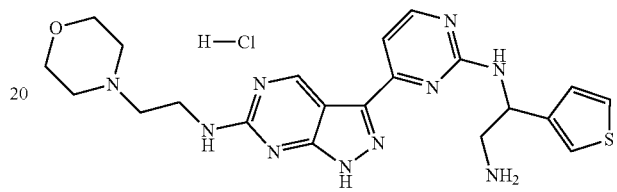

(2-{4-[6-(2-Morpholin-4-yl-ethylamino)-1H-pyrazolo[3,4-d]pyrimidin-3-yl]-pyrimidin-2-ylamino}-2-thiophen-3-yl-ethyl)-carbamic acid tert-butyl ester (200 mg, 0.35 mmol) was dissolved in EtOH (4 mL), then conc. HCl (4 mL) was added. The reaction mixture was stirred at room temperature for 15 hours. The solvent was removed under reduced pressure to afford the crude product which was purified by prep-HPLC to afford N1-{4-[6-(2-morpholin-4-yl-ethylamino)-1H-pyrazolo[3,4-d]pyrimidin-3-yl]-pyrimidin-2-yl}-1-thiophen-3-yl-ethane-1,2-diamine; hydrochloride. (Yield 17 mg, 8.4%).

¹H NMR (300 MHz, CD₃OD): δ 9.52 (brs, 1H), 8.52 (d, 1H, J=6.0 Hz), 7.68-7.54 (m, 3H), 7.36 (d, 1H, J=5.1 Hz), 6.02 (brs, 1H), 4.10-3.88 (m, 6H), 3.76-3.53 (m, 6H), 3.28-3.23 (m, 2H). LC-MS: [M+H]⁺ 467.

Example 83

N1-{4-[6-(2-Morpholin-4-yl-ethylamino)-1H-pyrazolo[3,4-d]pyrimidin-3-yl]-pyrimidin-2-yl}-1-phenyl-ethane-1,2-diamine; hydrochloride

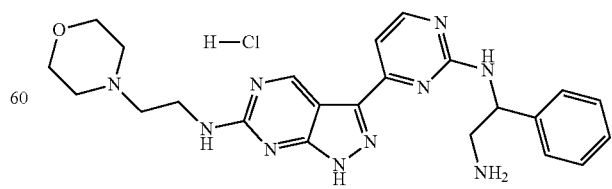

497

Step A (2-{4-[6-(2-Morpholin-4-yl-ethylamino)-1H-pyrazolo[3,4-d]pyrimidin-3-yl]-pyrimidin-2-ylamino}-2-phenyl-ethyl)-carbamic acid tert-butyl ester

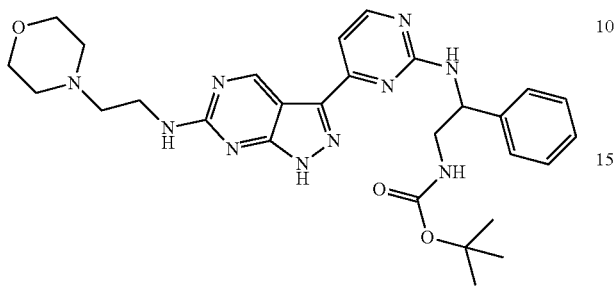

(2-{4-[6-(2-Morpholin-4-yl-ethylamino)-1H-pyrazolo[3,4-d]pyrimidin-3-yl]-pyrimidin-2-ylamino}-2-phenyl-ethyl)-carbamic acid tert-butyl ester was prepared from [3-(2-methanesulfonyl-pyrimidin-4-yl)-1H-pyrazolo[3,4-d]pyrimidin-6-yl]-(2-morpholin-4-yl-ethyl)-amine (from Example 11 supra) and (2-amino-2-phenyl-ethyl)-carbamic acid tert-butyl ester (from Example 1 supra) by following the method in Example 61.

Step B

N1-{4-[6-(2-Morpholin-4-yl-ethylamino)-1H-pyrazolo[3,4-d]pyrimidin-3-yl]-pyrimidin-2-yl}-1-phenyl-ethane-1,2-diamine; hydrochloride

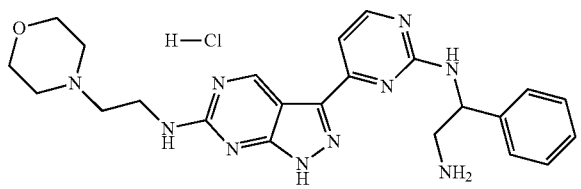

(2-{4-[6-(2-Morpholin-4-yl-ethylamino)-1H-pyrazolo[3,4-d]pyrimidin-3-yl]-pyrimidin-2-ylamino}-2-phenyl-ethyl)-carbamic acid tert-butyl ester (130 mg, 0.23 mmol) was dissolved in EtOH (4 mL), then HCl (4 mL) was added. The reaction mixture was stirred at room temperature for 15 hours. The solvent was removed under reduced pressure to afford the crude product which was purified by prep-HPLC to afford N1-{4-[6-(2-morpholin-4-yl-ethylamino)-1H-pyrazolo[3,4-d]pyrimidin-3-yl]-pyrimidin-2-yl}-1-phenyl-ethane-1,2-diamine; hydrochloride. (Yield 25 mg, 19.1%).

$^1$H NMR (300 MHz, CD$_3$OD): δ 9.51 (brs, 1H), 8.52 (brs, 1H), 7.73-7.66 (m, 3H), 7.49-7.36 (m, 3H), 6.04 (brs, 1H), 4.10-3.90 (m, 6H), 3.77-3.57 (m, 6H), 3.32-3.25 (m, 2H). LC-MS: [M+H]$^+$ 461.

Example 84

N-{3-[2-(3-Trifluoromethyl-benzylamino)-pyrimidin-4-yl]-1H-pyrazolo[3,4-d]pyrimidin-6-yl}-cyclohexane-1,4-diamine; hydrochloride

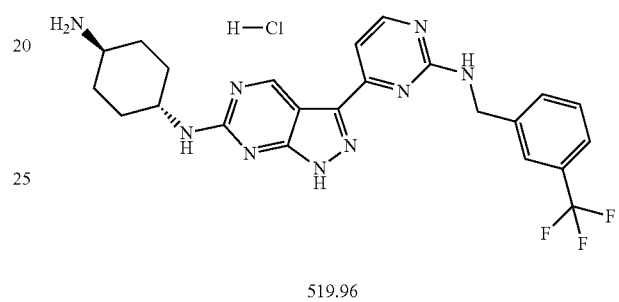

519.96

Step A (4-{3-[2-(3-Trifluoromethyl-benzylamino)-pyrimidin-4-yl]-1H-pyrazolo[3,4-d]pyrimidin-6-ylamino}-cyclohexyl)-carbamic acid tert-butyl ester

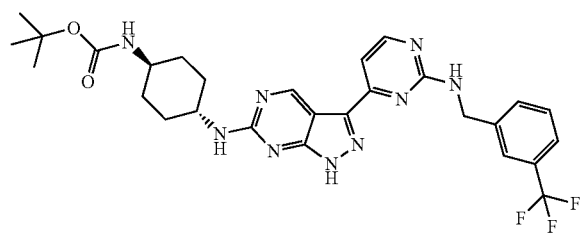 [SMILES: CC(C)(C)OC(=O)N[C@H]1CC[C@H](Nc2ncc3c(-c4ccnc(NCc5cccc(C(F)(F)F)c5)n4)n[nH]c3n2)CC1]

The mixture of {4-[3-(2-methanesulfinyl-pyrimidin-4-yl)-1H-pyrazolo[3,4-d]pyrimidin-6-ylamino]-cyclohexyl}-carbamic acid tert-butyl ester (from Example 9 supra) (150 mg, 0.32 mmol) and 3-trifluorobenzylamine (222 mg, 1.28 mmol) was heated at 130° C. with stirring for 2 hours. The resulting oil was purified by chromatography (silica gel, 7 g, 200-300 mesh, eluting with dichloromethane:methanol, 50:1 to 30:1) to afford (4-{3-[2-(3-trifluoromethyl-benzylamino)-pyrimidin-4-yl]-1H-pyrazolo[3,4-d]pyrimidin-6-ylamino}-cyclohexyl)-carbamic acid tert-butyl ester. (Yield 80 mg, 43.2%).

LC-MS: [M+H]$^+$ 584.

Step B

N-{3-[2-(3-Trifluoromethyl-benzylamino)-pyrimidin-4-yl]-1H-pyrazolo[3,4-d]pyrimidin-6-yl}-cyclohexane-1,4-diamine; hydrochloride

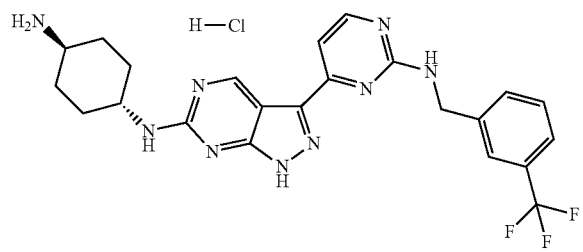

To a solution of (4-{3-[2-(3-trifluoromethyl-benzylamino)-pyrimidin-4-yl]-1H-pyrazolo[3,4-d]pyrimidin-6-ylamino}-cyclohexyl)-carbamic acid tert-butyl ester (80 mg, 0.14 mmol) in EtOH (4 mL) was added conc. HCl (4 mL). The reaction mixture was stirred at room temperature for 20 hours. The solvent was removed under reduced pressure and the residue was purified by prep-HPLC to afford N-{3-[2-(3-trifluoromethyl-benzylamino)-pyrimidin-4-yl]-1H-pyrazolo[3,4-d]pyrimidin-6-yl}-cyclohexane-1,4-diamine; hydrochloride. (Yield 40 mg, 50.0%).

$^1$H NMR (300 MHz, CD$_3$OD): δ 9.26 (s, 1H), 8.48 (s, 1H), 7.83-7.65 (m, 5H), 5.03 (brs, 2H), 4.03 (brs, 1H), 3.23 (brs, 1H), 2.29-2.17 (m, 4H), 1.66-1.60 (m, 4H). LC-MS: [M+H]$^+$ 484.

Example 85

N-{3-[2-(3-Fluoro-benzylamino)-pyrimidin-4-yl]-1H-pyrazolo[3,4-d]pyrimidin-6-yl}-cyclohexane-1,4-diamine; hydrochloride

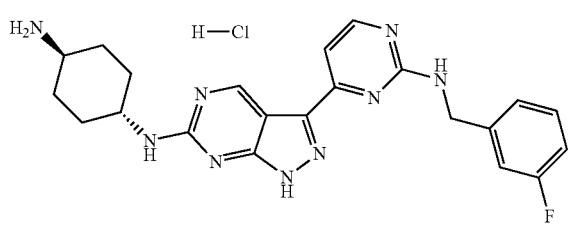

469.95

Step A (4-{3-[2-(3-Fluoro-benzylamino)-pyrimidin-4-yl]-1H-pyrazolo[3,4-d]pyrimidin-6-ylamino}-cyclohexyl)-carbamic acid tert-butyl ester

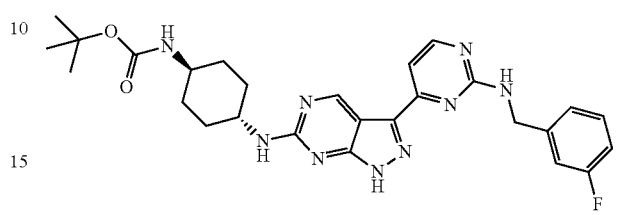

The mixture of {4-[3-(2-methanesulfinyl-pyrimidin-4-yl)-1H-pyrazolo[3,4-d]pyrimidin-6-ylamino]-cyclohexyl}-carbamic acid tert-butyl ester (from Example 9 supra) (140 mg, 0.3 mmol) and 3-fluorobenzylamine (148 mg, 1.2 mmol) was heated at 130° C. with stirring for 2 hours. The resulting oil was purified by chromatography (silica gel, 8 g, 200-300 mesh, eluting with dichloromethane:methanol, 50:1 to 30:1) to afford (4-{3-[2-(3-fluoro-benzylamino)-pyrimidin-4-yl]-1H-pyrazolo[3,4-d]pyrimidin-6-ylamino}-cyclohexyl)-carbamic acid tert-butyl ester. (Yield 110 mg, 69.6%).

LC-MS: [M+H]$^+$ 534.

Step B

N-{3-[2-(3-Fluoro-benzylamino)-pyrimidin-4-yl]-1H-pyrazolo[3,4-d]pyrimidin-6-yl}-cyclohexane-1,4-diamine; hydrochloride

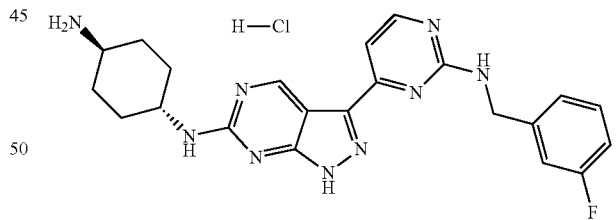

To a solution of (4-{3-[2-(3-fluoro-benzylamino)-pyrimidin-4-yl]-1H-pyrazolo[3,4-d]pyrimidin-6-ylamino}-cyclohexyl)-carbamic acid tert-butyl ester (110 mg, 0.23 mmol) in EtOH (4 mL) was added conc. HCl (4 mL). The reaction mixture was stirred at room temperature for 15 hours. The solvent was removed under reduced pressure and the residue was purified by prep-HPLC to afford N-{3-[2-(3-fluoro-benzylamino)-pyrimidin-4-yl]-1H-pyrazolo[3,4-d]pyrimidin-6-yl}-cyclohexane-1,4-diamine; hydrochloride. (Yield 50 mg, 39.1%).

$^1$H NMR (300 MHz, CD$_3$OD): δ 9.15 (s, 1H), 8.49 (s, 1H), 7.76 (d, 1H, J=6.3 Hz), 7.50-7.26 (m, 3H), 7.12-7.08 (m, 1H), 4.95 (brs, 2H), 4.03 (brs, 1H), 3.22 (brs, 1H), 2.29-2.17 (m, 4H), 1.66-1.60 (m, 4H). LC-MS: [M+H]+ 434.

Example 86

{3-[2-(3-Chloro-benzylamino)-pyrimidin-4-yl]-1H-pyrazolo[3,4-d]pyrimidin-6-yl}-piperidin-4-yl-amine; hydrochloride

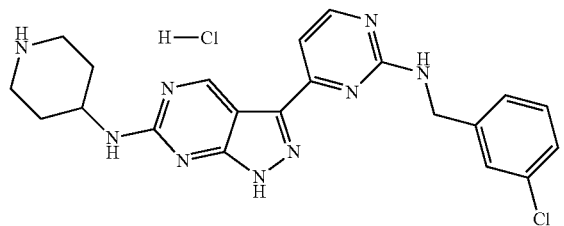

Step A

4-{3-[2-(3-Chloro-benzylamino)-pyrimidin-4-yl]-1H-pyrazolo[3,4-d]pyrimidin-6-ylamino}-piperidine-1-carboxylic acid tert-butyl ester

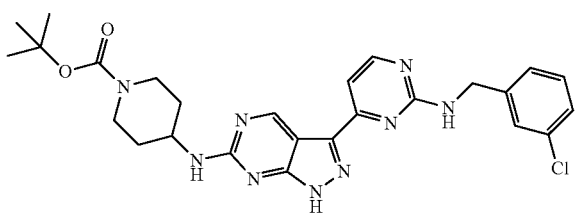 [SMILES: CC(C)(C)OC(=O)N1CCC(Nc2ncc3c(-c4ccnc(NCc5cccc(Cl)c5)n4)n[nH]c3n2)CC1]

The mixture of 4-[3-(2-methanesulfinyl-pyrimidin-4-yl)-1H-pyrazolo[3,4-d]pyrimidin-6-ylamino]-piperidine-1-carboxylic acid tert-butyl ester (from Example 13 supra) (230 mg, 0.50 mmol) and 3-chlorobenzylamine (283 mg, 2.0 mmol) was heated at 130° C. with stirring for 2 hours. The resulting oil was purified by chromatography (silica gel, 7 g, 200-300 mesh, eluting with dichloromethane:methanol, 50:1 to 30:1) to afford 4-{3-[2-(3-chloro-benzylamino)-pyrimidin-4-yl]-1H-pyrazolo[3,4-d]pyrimidin-6-ylamino}-piperidine-1-carboxylic acid tert-butyl ester. (Yield 80 mg, 30.0%).

LC-MS: [M+H]+ 536.

Step B

{3-[2-(3-Chloro-benzylamino)-pyrimidin-4-yl]-1H-pyrazolo[3,4-d]pyrimidin-6-yl}-piperidin-4-yl-amine; hydrochloride

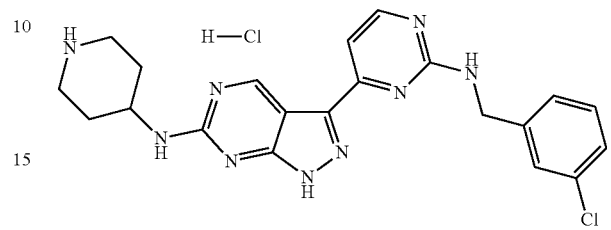

To a solution of 4-{3-[2-(3-chloro-benzylamino)-pyrimidin-4-yl]-1H-pyrazolo[3,4-d]pyrimidin-6-ylamino}-piperidine-1-carboxylic acid tert-butyl ester (80 mg, 0.15 mmol) in EtOH (4 mL) was added conc. HCl (4 mL). The reaction mixture was stirred at room temperature for 15 hours. The solvent was then removed and the residue was purified by prep-HPLC to afford {3-[2-(3-chloro-benzylamino)-pyrimidin-4-yl]-1H-pyrazolo[3,4-d]pyrimidin-6-yl}-piperidin-4-yl-amine; hydrochloride. (Yield 20 mg, 26.3%).

$^1$H NMR (300 MHz, CD$_3$OD): δ 9.21 (brs, 1H), 8.45 (brs, 1H), 7.76 (d, 1H, J=6.6 Hz), 7.54 (s, 1H), 7.48-7.38 (m, 3H), 4.92 (brs, 2H), 4.31-4.28 (m, 1H), 3.56-3.50 (m, 2H), 3.27-3.18 (m, 2H), 2.38-2.32 (m, 2H), 1.99-1.92 (m, 2H). LC-MS: [M+H]+ 436.

Example 87

N-{3-[2-(3-Chloro-benzylamino)-pyrimidin-4-yl]-1H-pyrazolo[3,4-d]pyrimidin-6-yl}-N',N'-dimethyl-ethane-1,2-diamine; hydrochloride

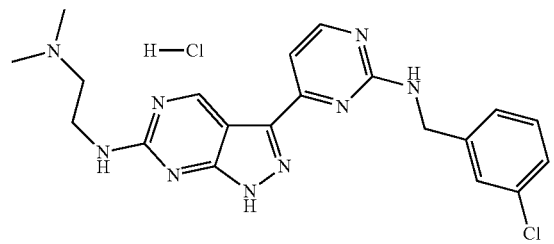

The mixture of N'-[3-(2-methanesulfonyl-pyrimidin-4-yl)-1H-pyrazolo[3,4-d]pyrimidin-6-yl]-N,N-dimethyl-ethane-1,2-diamine (from Example 23 supra) (160 mg, crude) and 3-chlorobenzylamine (236 mg, 1.67 mmol) was heated at 130° C. with stirring for 3 hours. The resulting oil was purified by chromatography (silica gel, 7 g, 200-300 mesh, eluting with dichloromethane:methanol, 10:1) and further purified by prep-HPLC. Concentrated HCl was added to the fractions with product and concentrated under reduced pressure to give N-{3-[2-(3-chloro-benzylamino)-pyrimidin-4-yl]-1H-pyrazolo[3,4-d]pyrimidin-6-yl}-N',N'-dimethyl-ethane-1,2-diamine; hydrochloride. (Yield 26 mg).

¹H NMR (300 MHz, CD₃OD): δ 9.12 (s, 1H), 8.36 (s, 1H), 7.64 (d, 1H, J=5.7 Hz), 7.42-7.24 (m, 4H), 4.89 (brs, 2H), 3.89 (brs, 2H), 3.43 (s, 2H), 2.90 (s, 6H). LC-MS: [M+H]⁺ 424; [M−H]⁺ 422.

Example 88

{3-[2-(3-Chloro-benzylamino)-pyrimidin-4-yl]-1H-pyrazolo[3,4-d]pyrimidin-6-yl}-piperidin-4-ylmethyl-amine; hydrochloride

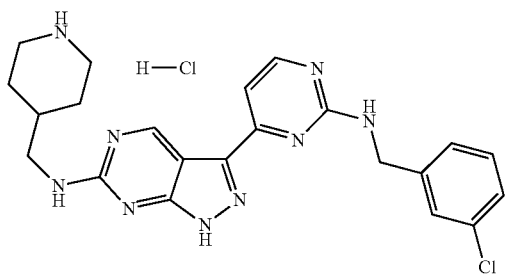

Step A 4-({3-[2-(3-Chloro-benzylamino)-pyrimidin-4-yl]-1H-pyrazolo[3,4-d]pyrimidin-6-ylamino}-methyl)-piperidine-1-carboxylic acid tert-butyl ester

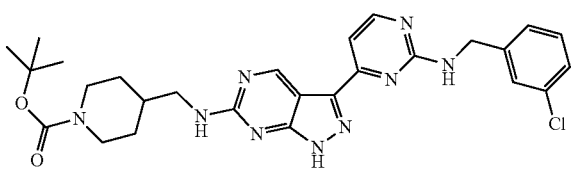 [SMILES: CC(C)(C)OC(=O)N1CCC(CNc2ncc3c(-c4ccnc(NCc5cccc(Cl)c5)n4)n[nH]c3n2)CC1]

The mixture of 4-{[3-(2-methanesulfinyl-pyrimidin-4-yl)-1H-pyrazolo[3,4-d]pyrimidin-6-ylamino]-methyl}-piperidine-1-carboxylic acid tert-butyl ester (from Example 15 supra) (200 mg, 0.42 mmol) and 3-chlorobenzylamine (238 mg, 1.7 mmol) was heated at 130° C. with stirring for 2 hours. The resulting oil was purified by chromatography (silica gel, 7 g, 200-300 mesh, eluting with dichloromethane:methanol, 50:1 to 30:1) to afford 4-({3-[2-(3-chloro-benzylamino)-pyrimidin-4-yl]-1H-pyrazolo[3,4-d]pyrimidin-6-ylamino}-methyl)-piperidine-1-carboxylic acid tert-butyl ester. (Yield 200 mg, 86.2%).

LC-MS: [M+H]⁺ 550.

Step B

{3-[2-(3-Chloro-benzylamino)-pyrimidin-4-yl]-1H-pyrazolo[3,4-d]pyrimidin-6-yl}-piperidin-4-ylmethyl-amine; hydrochloride

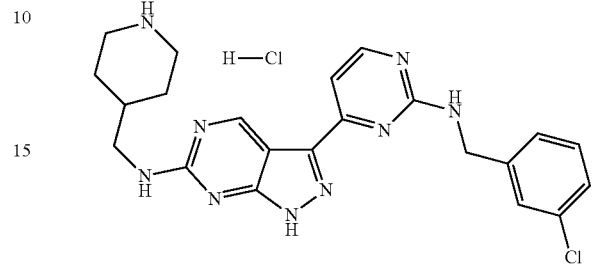

To a solution of 4-({3-[2-(3-chloro-benzylamino)-pyrimidin-4-yl]-1H-pyrazolo[3,4-d]pyrimidin-6-ylamino}-methyl)-piperidine-1-carboxylic acid tert-butyl ester (200 mg, 0.36 mmol) in EtOH (4 mL) was added conc. HCl (4 mL). The reaction mixture was stirred at room temperature for 15 hours. The solvent was then removed and the residue was purified by prep-HPLC to afford {3-[2-(3-chloro-benzylamino)-pyrimidin-4-yl]-1H-pyrazolo[3,4-d]pyrimidin-6-yl}-piperidin-4-ylmethyl-amine; hydrochloride. (Yield 60 mg, 30.0%).

¹H NMR (300 MHz, CD₃OD): δ 9.18 (s, 1H), 8.48 (s, 1H), 7.76 (d, 1H, J=6.9 Hz), 7.54-7.38 (m, 4H), 5.04 (s, 2H), 3.56-3.42 (m, 4H), 3.07-2.99 (m, 2H), 2.14-2.06 (m, 3H), 1.64-1.51 (m, 2H). LC-MS: [M+H]⁺ 451; [M−H]⁺ 449.

Example 89

N-{3-[2-(3-Chloro-benzylamino)-pyrimidin-4-yl]-1H-pyrazolo[3,4-d]pyrimidin-6-yl}-cyclohexane-1,4-diamine; hydrochloride

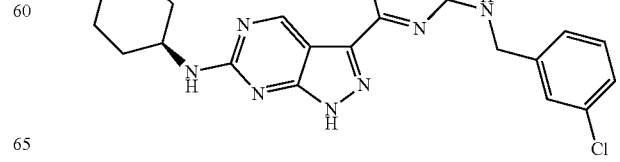

Step A (4-{3-[2-(3-Chloro-benzylamino)-pyrimidin-4-yl]-1H-pyrazolo[3,4-d]pyrimidin-6-ylamino}-cyclohexyl)-carbamic acid tert-butyl ester

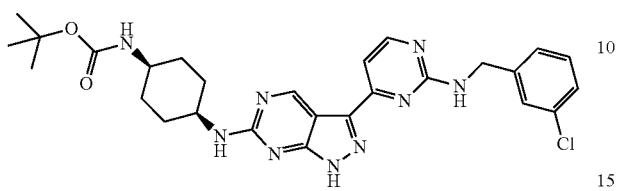

The mixture of 4-[3-(2-methanesulfinyl-pyrimidin-4-yl)-1H-pyrazolo[3,4-d]pyrimidin-6-ylamino]-cyclohexyl}-carbamic acid tert-butyl ester (from Example 19 supra) (300 mg, 0.64 mmol) and 3-chlorobenzylamine (360 mg, 2.54 mmol) was heated at 130° C., with stirring for 2 hours. The resulting oil was purified by chromatography (silica gel, 10 g, 200-300 mesh, eluting with dichloromethane:methanol, 30:1 to 10:1) to afford (4-{3-[2-(3-chloro-b enzylamino)-pyrimidin-4-yl]-1H-pyrazolo[3,4-d]pyrimidin-6-ylamino}-cyclohexyl)-carbamic acid tert-butyl ester. (Yield 150 mg, 43.5%).
LC-MS: [M+H]$^+$ 550.

Step B

N-{3-[2-(3-Chloro-benzylamino)-pyrimidin-4-yl]-1H-pyrazolo[3,4-d]pyrimidin-6-yl}-cyclohexane-1,4-diamine; hydrochloride

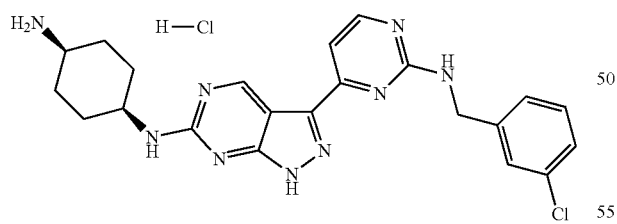

To a solution of (4-{3-[2-(3-chloro-benzylamino)-pyrimidin-4-yl]-1H-pyrazolo[3,4-d]pyrimidin-6-ylamino}-cyclohexyl)-carbamic acid tert-butyl ester (150 mg, 0.27 mmol) in ethanol (5 mL) was added concentrated hydrochloric acid (3 mL) slowly. The reaction mixture was stirred at room temperature for 15 hours. The solvent was then removed under reduced pressure and the solid was purified by prep-HPLC and concentrated to afford N-{3-[2-(3-chloro-benzylamino)-pyrimidin-4-yl]-1H-pyrazolo[3,4-d]pyrimidin-6-yl}-cyclohexane-1,4-diamine; hydrochloride. (Yield 25 mg, 20.3%).

$^1$H NMR (300 MHz, CD$_3$OD): δ 9.17 (s, 1H), 8.48 (s, 1H), 7.72 (s, 1H), 7.52-7.44 (m, 4H), 4.92 (s, 2H), 4.31 (s, 1H), 2.08-1.85 (m, 9H). LC-MS: [M+H]$^+$ 450; [M–H]$^+$ 448.

Example 90

{3-[2-(3-Chloro-benzylamino)-pyrimidin-4-yl]-1H-pyrazolo[3,4-d]pyrimidin-6-yl}-(2-pyrrolidin-1-yl-ethyl)-amine; hydrochloride 449.950

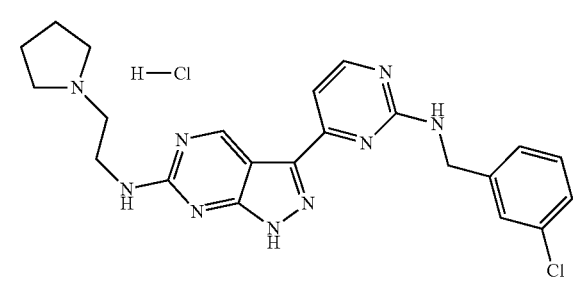

The mixture of [3-(2-methanesulfonyl-pyrimidin-4-yl)-1H-pyrazolo[3,4-d]pyrimidin-6-yl]-(2-pyrrolidin-1-yl-ethyl)-amine (from Example 17 supra) (180 mg, 0.46 mmol) and 3-chlorobenzylamine (131 mg, 0.92 mmol) was heated at 130° C. with stirring for 2 hours. The resulting oil was purified by chromatography (silica gel, 7 g, 200-300 mesh, eluting with dichloromethane:methanol, 40:1-10:1) to afford the crude product (110 mg, crude) which undergo purification by prep-HPLC to give pure compound (35 mg). To a solution of this compound (35 mg, 0.08 mmol) in EtOH (5 mL) was added conc. HCl (2 mL). The reaction mixture was stirred at room temperature for 4 hours. The solvent was removed and the residue was purified by prep-HPLC to afford {3-[2-(3-chloro-benzylamino)-pyrimidin-4-yl]-1H-pyrazolo[3,4-d]pyrimidin-6-yl}-(2-pyrrolidin-1-yl-ethyl)-amine; hydrochloride. (Yield 42 mg, 20%).

$^1$H NMR (300 MHz, CD$_3$OD): δ 9.18 (s, 1H), 8.46 (s, 1H), 7.78 (d, 1H, J=6.6 Hz), 7.54-7.52 (m, 4H), 4.97 (s, 2H), 3.98-3.95 (m, 2H), 3.88-3.82 (m, 2H), 3.59-3.55 (m, 2H), 3.26-3.18 (m, 2H), 2.23-2.06 (m, 4H). LC-MS: [M+H]$^+$ 450; [M–H]$^+$ 448.

Example 91

2-{3-[2-(3-Chloro-benzylamino)-pyrimidin-4-yl]-1H-pyrazolo[3,4-d]pyrimidin-6-ylamino}-ethanol; hydrochloride 396.842

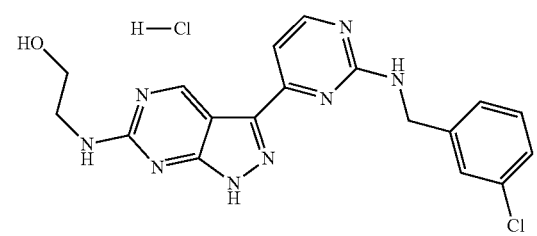

The mixture of 2-[3-(2-methane sulfinyl-pyrimidin-4-yl)-1H-pyrazolo[3,4-d]pyrimidin-6-ylamino]-ethanol (from Example 21 supra) (1.9 g, crude, 2.31 mmol) and 3-chlorobenzylamine (797 mg, 4.62 mmol) was heated at 130° C. with stirring for 3 hours. The solvent was removed under reduced pressure and the solid was purified by prep-TLC and prep-HPLC. Concentrated HCl was added to the fractions with product and concentrated under reduced pressure to give 2-{3-[2-(3-chloro-benzylamino)-pyrimidin-4-yl]-1H-pyrazolo[3,4-d]pyrimidin-6-ylamino}-ethanol; hydrochloride. (Yield 28 mg, 3.1% of the 3 steps).

$^1$H NMR (300 MHz, CD$_3$OD): δ 8.46 (s, 1H), 7.73 (s, 1H), 7.51 (s, 1H), 7.42-7.35 (m, 4H), 4.91 (s, 2H), 3.80-3.78 (m, 2H), 3.69-3.67 (m, 2H). LC-MS: [M+H]$^+$ 397; [M−H]$^+$395.

Example 92

{3-[2-(3-Chloro-benzylamino)-pyrimidin-4-yl]-1H-pyrazolo[3,4-d]pyrimidin-6-yl}-(2-piperazin-1-yl-ethyl)-amine; hydrochloride 464.965

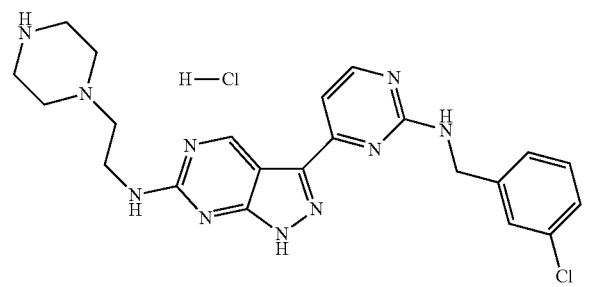

Step A 4-(2-{3-[2-(3-Chloro-benzylamino)-pyrimidin-4-yl]-1H-pyrazolo[3,4-d]pyrimidin-6-ylamino}-ethyl)-piperazine-1-carboxylic acid tert-butyl ester

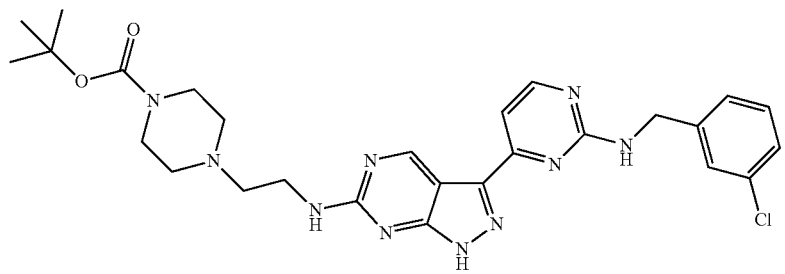 [SMILES: CC(C)(C)OC(=O)N1CCN(CCNc2ncc3c(-c4ccnc(NCc5cccc(Cl)c5)n4)n[nH]c3n2)CC1]

The mixture of 4-{2-[3-(2-methanesulfonyl-pyrimidin-4-yl)-1H-pyrazolo[3,4-d]pyrimidin-6-ylamino]-ethyl}-piperazine-1-carboxylic acid tert-butyl ester (from Example 27 supra) (153 mg, 0.304 mmol) and 3-chlorobenzylamine (171 mg, 1.21 mmol) was heated at 130° C. with stirring for 3 hours. The resulting oil was purified by chromatography (silica gel, 7 g, 100-200 mesh, eluting with dichloromethane:methanol, 10:1) and further purified by prep-HPLC to afford 4-(2-{3-[2-(3-chloro-benzylamino)-pyrimidin-4-yl]-1H-pyrazolo[3,4-d]pyrimidin-6-ylamino}-ethyl)-piperazine-1-carboxylic acid tert-butyl ester. (Yield 90 mg, 52%).

LC-MS: [M+H]$^+$ 565.

Step B

{3-[2-(3-Chloro-benzylamino)-pyrimidin-4-yl]-1H-pyrazolo[3,4-d]pyrimidin-6-yl}-(2-piperazin-1-yl-ethyl)-amine; hydrochloride

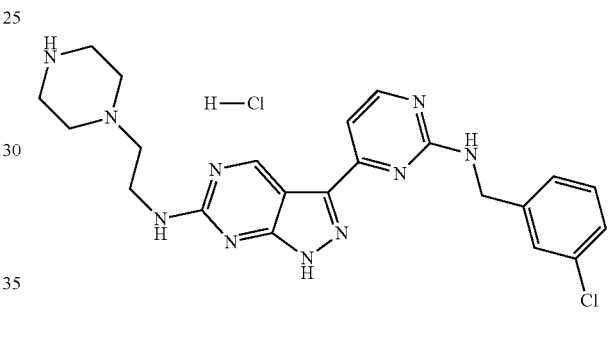

To a solution of 4-(2-{3-[2-(3-chloro-benzylamino)-pyrimidin-4-yl]-1H-pyrazolo[3,4-d]pyrimidin-6-ylamino}-ethyl)-piperazine-1-carboxylic acid tert-butyl ester (90 mg, 0.16 mmol) in EtOH (10 mL) was added conc. HCl (5 mL). The reaction mixture was stirred at room temperature for 15 hours. The solvent was removed to afford {3-[2-(3-Chloro-benzylamino)-pyrimidin-4-yl]-1H-pyrazolo[3,4-d]pyrimidin-6-yl}-(2-piperazin-1-yl-ethyl)-amine; hydrochloride. (Yield 46 mg).

$^1$H NMR (300 MHz, CD$_3$OD): δ 9.08 (brs, 1H), 8.34 (s, 1H), 7.64 (d, 1H, J=6.0 Hz), 7.40-7.25 (m, 4H), 4.85 (s, 2H), 3.94-3.55 (m, 12H). LC-MS: [M+H]$^+$ 465; [M−H]$^+$ 463.

Example 93

{3-[2-(3-Chloro-benzylamino)-pyrimidin-4-yl]-1H-pyrazolo[3,4-d]pyrimidin-6-yl}-(2-piperazin-1-yl-ethyl)-amine; hydrochloride

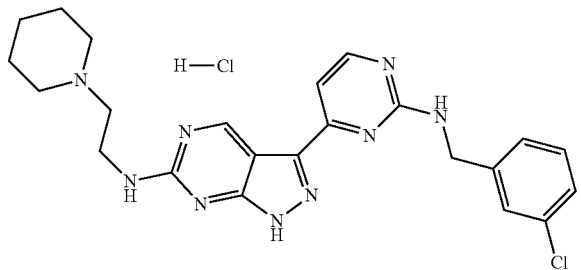

463.977

The mixture of [3-(2-methanesulfonyl-pyrimidin-4-yl)-1H-pyrazolo[3,4-d]pyrimidin-6-yl]-(2-piperidin-1-yl-ethyl)-amine (from Example 25 supra) (196 mg, 0.49) and 3-chlorobenzyl-amine (274 mg, 1.94 mmol) was heated at 130° C. with stirring for 3 hours. The resulting oil was purified by chromatography (silica gel, 7 g, 100-200 mesh, eluting with dichloromethane:methanol, 10:1) and further purified by prep-HPLC. Concentrated HCl was added to the fractions with product and concentrated under reduced pressure to give {3-[2-(3-chloro-benzylamino)-pyrimidin-4-yl]-1H-pyrazolo[3,4-d]pyrimidin-6-yl}-(2-piperazin-1-yl-ethyl)-amine; hydrochloride. (Yield 100 mg).

$^1$H NMR (300 MHz, CD$_3$OD): δ 9.18 (brs, 1H), 8.45 (s, 1H), 7.75 (d, 1H, J=6.3 Hz), 7.52-7.34 (m, 4H), 4.98 (s, 2H), 4.01-3.97 (m, 2H), 3.74-3.70 (m, 2H), 3.47-3.43 (m, 2H), 3.09-3.00 (m, 2H), 1.94-1.53 (m, 6H). LC-MS: [M+H]$^+$ 464; [M−H]$^+$ 462.

The pharmacological properties of the compounds of this invention may be confirmed by a number of pharmacological assays. The exemplified antiproliferative activity assays which follow have been carried out with compounds according to the invention.

If test compounds were assessed in multiple runs of the same assay, the activities reported in Table I below are the averages of the results obtained from the multiple runs of the assay.

Example 94

DYRK1B Kinase TR-FRET (IMAP-Tb) Assay

Assay Principle

The kinase TR-FRET (IMAP-Tb) assay uses a fluorescence labeled substrate peptide in the kinase reaction. Upon phosphorylation by the kinase, phosphopeptide is produced, which will be detected by the binding solution provided in IMAP TR-FRET binding kit. After the completion of the kinase reaction, the reaction will be stopped by adding the binding solution containing terbium tracer. This tracer is immobilized on the surface of the IMAP beads, which also contain metal ions on the beads that bind to the phospho-groups of the products. Thus the phosphorylated product of the reaction can enter into close proximity to the tracer, producing resonance energy transfer. Due to the long lifetime of terbium (Tb) fluorescence the detection can be run in time resolved mode, which virtually eliminates fluorescence interference from assay components or compounds.

The TR-FRET signal measurement from this assay, given as an IC$_{50}$ measurement, is a measure of a test compound's ability to interfere with the phosphorylation of the peptide substrate, that is it inhibits the phosphorylation of the substrate peptide by DYRK1B, and is thus a measure of the test compound's ability to inhibit the activity of DYRK1B. IC$_{50}$ is the amount of test compound that inhibits 50% of the activity of DYRK1B in this assay. In some cases where the IC$_{50}$ was not determined, then the % inhibition at 10 μM test compound concentration may be reported. The results of this assay for sample compounds of the invention are provided in Table I below.

Materials and Reagents
1. Human DYRK1B: from Invitrogen. Part #PR8350B (former PV4649)
2. Substrate Peptide: in-house synthesized: RRRFRPASPL-RGPPK
3. IMAP TR-FRET IPP Explorer Kit: from Molecular Devices. Part #R8157
4. Kinase Assay Buffer (KAB): 10 mM HEPES pH 7.0, 50 mM NaCl, 5 mM MgCl$_2$, 1 mM DTT, 1 mM NaVO$_4$, 200 μg/mL BSA (0.02%)
5. Assay Plate: Remp polypropylene clear 384-well microplate. Cat#23490-102
6. Detection Plate: Costa black 384-well microplate. Cat #3710

Assay Procedure: this Assay was Performed as Follows:
1. Transfer 1.5 μL of 20× compound solution to each well of an assay plate.
2. Add to each well 22.5 μL of KAB Buffer.
3. Add to each well 3 μL of the solution of DYRK1B and ATP. The final concentration of DYRK1B is 1.25 nM and ATP concentration is 70 μM (3 times of Km of ATP, which is 23.3 μM)
4. Add to each well 3 μL of the substrate peptide. The assay concentration is 1.0 μM
5. Incubate the assay plates at 37° C. for 60 minutes.
6. Add 18 μL of Detection Solution (1:800 diluted Progress bead stock, 1:400 diluted Tb stock, 80% Buffer A, and 20% Buffer B) into each well of detection plates.
7. Transfer 6 μL of assay solution from the assay plate to the detection plate.
8. Shake detection plates for 30 minutes.
9. Read plates in Envision with wavelength set at excitation 340 nm for Tb, emission 490 nm, and excitation 520 nm.
10. Calculation:

TR-FRET Signal=(Reading at 520 nM/Reading at 490 nM)×2000000

Example 95

DYRK1A Kinase TR-FRET (IMAP-Tb) Assay

Assay Principle

The kinase TR-FRET (IMAP-Tb) assay uses a fluorescence labeled substrate peptide in the kinase reaction. Upon phosphorylation by the kinase, phosphopeptide is produced, which will be detected by the binding solution provided in IMAP TR-FRET binding kit. After the completion of the kinase reaction, the reaction will be stopped by adding the binding solution containing terbium tracer. This tracer is immobilized on the surface of the IMAP beads, which also contain metal ions on the beads that bind to the phospho-groups of the products. Thus the phosphorylated product of the reaction can enter into close proximity to the tracer, producing resonance energy transfer. Due to the long lifetime of terbium (Tb) fluorescence the detection can be run in time resolved mode, which virtually eliminates fluorescence interference from assay components or compounds.

The TR-FRET signal measurement from this assay, given as an $IC_{50}$ measurement, is a measure of a test compound's ability to interfere with the phosphorylation of the peptide substrate, that is it inhibits the phosphorylation of the substrate peptide by DYRK1A, and is thus a measure of the test compound's ability to inhibit the activity of DYRK1A. $IC_{50}$ is the amount of test compound that inhibits 50% of the activity of DYRK1A in this assay. In some cases where the $IC_{50}$ was not determined, then the % inhibition at 10 μM test compound concentration may be reported. The results of this assay for sample compounds of the invention are provided in Table I below.

Materials and Reagents
1. Human DYRK1A: from Invitrogen. Part #PV3997
2. Substrate Peptide: RRRFRPASPLRGPPK
3. IMAP TR-FRET IPP Explorer Kit: from Molecular Devices. Part #R8157
4. Kinase Assay Buffer (KAB): 10 mM HEPES pH 7.0, 50 mM NaCl, 5 mM $MgCl_2$, 1 mM DTT, 1 mM $NaVO_4$, 200 ug/mL BSA (0.02%)
5. Assay Plate: Remp polypropylene clear 384-well microplate. Cat#23490-102
6. Detection Plate: Costa black 384-well microplate. Cat #3710

Assay Procedure: this Assay was Performed as Follows:
1. Transfer 1.5 μL of 20× compound solution to each well of an assay plate.
2. Add to each well 22.5 μL of KAB Buffer.
3. Add to each well 3 μL of the solution of DYRK1A and ATP. The final concentration of DYRK1A is 1.25 nM and ATP concentration is 70 μM (3 times of Km of ATP, which is 23.3 μM)
4. Add to each well 3 μL of the substrate peptide. The assay concentration is 1.0 μM
5. Incubate the assay plates at 37° C. for 60 minutes.
6. Add 18 μL of Detection Solution (1:800 diluted Progress bead stock, 1:400 diluted Tb stock, 80% Buffer A, and 20% Buffer B) into each well of detection plates.
7. Transfer 6 μL of assay solution from the assay plate to the detection plate.
8. Shake detection plates for 30 minutes.
9. Read plates in Envision with wavelength set at excitation 340 nm for Tb, emission 490 nm, and excitation 520 nm.
10. Calculation:

TR-FRET Signal=(Reading at 520 nM/Reading at 490 nM)×2000000

Example 96

SW620 Cell Viability Assay

1. Cell Plate Preparation: SW620 human colon cancer cells (known to express DYRK1B), obtained from ATCC, were seeded into 96-well plates at $3\times10^3$ cells/well in 50 μL of media.
  Harvested the required number of cells (counts & viability determined by Guava Viacount).
  Centrifuge cells to pellet and removed supernant.
  Resuspended in growth media (50 μL/well) & pipetted thoroughly to break up clumps.
  Setup for ~100 wells/plate, therefore, $V_T$=5 mL/plate @ $1.2\times10^5$ cells/mL.
1A. Some cells (S—) were allowed to attach for 24 hrs, serum starved for 48 hrs, and then followed with test compound treatments.
  Test compound solution were prepared in regular corresponding media supplemented with serum.
2. Test compound Preparation: Drugs were solubilized in either DMSO or media and prepared at various stock concentrations.
  All compounds were incubated at 37° C. for 30 minutes and vortexed.
  (5 mM stocks of test compound were prepared for non-soluble test compounds)
3. Test compound Plate Preparation:
  The 10 mM test compound stock was diluted to a concentration of 100× the final $C_{max}$ concentration.
  Then the test compound stock is diluted 50-fold in media and/or second test compound for a final $C_{max}$ concentration in the test compound plate.
  The $C_{max}$ in the test compound plate (2% DMSO) is 2-fold higher than the final $C_{max}$ in the cell plate (60 μl, titrations were 1:3).
4. Viability Assay: This assay was performed as follows:
  Transfer 50 μL of test compound solution per well from the test compound plate onto the cell plate prepared in Step #1.
  Mix the plate with treated cells by pipetting up and down three times with 200 μL multi-channel pipette.
  Incubate the cells in 5% $CO_2$ incubator @ 37° C. for 4 days.
  Run the CellTiter-Glo™ Luminescent Cell Viability Assay.

The results of this assay, given as $EC_{50}$ values, indicate the concentration of test compound that inhibits tumor cell proliferation by 50%. The results of this assay for sample compounds of the invention are provided in Table I below.

TABLE 1

| | Kinase enzyme and cellular activity | | |
|---|---|---|---|
| Example | Enzyme IC50 (μM) DYRK1B | Enzyme IC50 (μM) DYRK1A | Cellular EC50 (μM) SW620 |
| 44 | 32% | 3.956 | |
| 45 | 4.581 | 2.312 | |
| 46 | 43% | 55% | |
| 47 | 1.061 | 1.394 | >10 |
| 48 | 2.921 | 2.963 | |
| 49 | 0.101 | 0.0124 | 1.706 |
| 50 | >10 | 4.91 | |
| 51 | >10 | 9.02 | |
| 52 | 0.241 | 0.594 | 0.923 |
| 53 | 0.183 | 0.405 | 1.84 |
| 54 | 4.962 | 3.853 | >10 |
| 55 | 0.181 | 0.502 | 1.85 |
| 56 | 0.194 | 0.346 | 4.10 |
| 57 | 1.551 | 2.621 | >10 |
| 58 | 0.762 | 2.608 | 6.414 |
| 59 | 0.924 | 0.663 | >10 |
| 60 | 0.234 | 0.785 | >10 |
| 62 | 0.0586 | 0.0384 | >10 |
| 63 | 0.0671 | 0.0371 | 0.90 |
| 64 | 0.353 | 0.242 | >10 |
| 61 | 0.0958 | 0.061 | >10 |
| 65 | <0.005 | 0.021 | |
| 66 | 0.0172 | 0.0148 | 0.04 |
| 67 | 0.00517 | 0.0046 | |
| 68 | 0.011 | 0.011 | |
| 69 | 0.197 | 0.231 | 0.001 |
| 70 | 0.0125 | 0.0062 | >10 |
| 71 | 0.006 | 0.0046 | 0.027 |

TABLE 1-continued

Kinase enzyme and cellular activity

| Example | Enzyme IC50 (μM) DYRK1B | Enzyme IC50 (μM) DYRK1A | Cellular EC50 (μM) SW620 |
|---|---|---|---|
| 72 | 0.009 | 0.013 | 0.056 |
| 73 | 9.588 | 4.879 | |
| 74 | <0.0046 | 0.0046 | >10 |
| 75 | 2.728 | 2.581 | |
| 76 | 0.0121 | 0.0076 | 0.14 |
| 77 | 0.04 | 0.0129 | 5.99 |
| 78 | <0.0046 | 0.0046 | 0.70 |
| 79 | 0.601 | 1.11 | >10 |
| 80 | <0.0046 | 0.0046 | 0.89 |
| 81 | 0.0944 | 0.112 | 1.75 |
| 82 | 0.012 | 0.0050 | 0.27 |
| 83 | 0.0183 | 0.0059 | 0.56 |
| 84 | 0.007 | 0.005 | |
| 85 | <0.0046 | 0.0046 | |
| 86 | 0.078 | 0.047 | |
| 87 | 0.69 | 0.31 | |
| 88 | 0.016 | 0.0089 | |
| 89 | 0.186 | 0.415 | |
| 90 | 1.315 | 0.536 | |
| 91 | 0.183 | 0.25 | |
| 92 | 0.057 | 0.076 | |
| 93 | 0.93 | 0.46 | |

What is claimed:

1. A compound of formula I

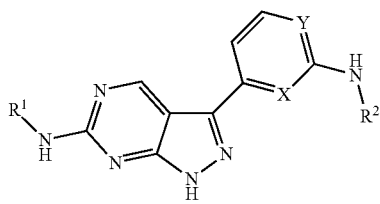

I wherein
X and Y are independently selected from CH and N;
$R^1$ is selected from the group consisting of
H,
$C_{1-4}$ alkyl,
$C_{1-4}$ alkyl substituted with up to 3 groups selected from cycloalkyl, heterocycle, $OR^3$, $NR^3R^4$ and CN,
Aryl,
Aryl substituted with up to three groups selected from $C_{1-4}$ alkyl, $OR^5$, $NR^5R^6$, halogen and CN,
Heterocycle,
Heterocycle substituted with up to three groups selected from $C_{1-4}$ alkyl, $OR^5$, $NR^5R^6$ and CN,
Cycloalkyl, and
Cycloalkyl substituted with up to three groups selected from $C_{1-4}$ alkyl, $OR^5$, $NR^5R^6$, halogen and CN;
$R^2$ is selected from the group consisting of $C_{2-6}$ alkyl and
$C_{1-6}$ alkyl substituted by up to 3 groups selected from
aryl,
aryl substituted with Cl, F, $CH_3$, or $CF_3$,
heteroaryl,
cycloalkyl,
heterocycle,
OH,
$OCH_3$,
$NR^5R^6$, and
CN;

$R^3$ and $R^4$ are independently selected from the group
H,
$C_{1-4}$ alkyl, and
$C_{1-4}$ alkyl substituted with up to three groups selected from cycloalkyl, heterocycle, OH, $OCH_3$, $NR^5R^6$ and CN; and
$R^5$ and $R^6$ are independently selected from the group
H and
$C_{1-4}$ alkyl;
or a pharmaceutically acceptable salt thereof.

2. The compound of claim 1, wherein either one of X or Y is N and the other is CH,
or a pharmaceutically acceptable salt thereof.

3. The compound of claim 1, wherein both X and Y are CH, or a pharmaceutically acceptable salt thereof.

4. The compound of claim 1, wherein both X and Y are N, or a pharmaceutically acceptable salt thereof.

5. The compound of claim 1, wherein $R^1$ is $C_{1-4}$ alkyl, or a pharmaceutically acceptable salt thereof.

6. The compound of claim 5, wherein $R^1$ is $C_{1-4}$ alkyl that optionally is substituted with heterocycle, or a pharmaceutically acceptable salt thereof.

7. The compound of claim 5, wherein $R^1$ is $C_{1-4}$ alkyl that optionally is substituted with $OR^3$ or $NR^3R^4$, and $R^3$ is H or $CH_3$, and $R^3$ and $R^4$ are independently $C_{1-4}$ alkyl, or a pharmaceutically acceptable salt thereof.

8. The compound of claim 1, wherein $R^1$ is cycloalkyl that optionally is substituted with $NR^5R^6$, or a pharmaceutically acceptable salt thereof.

9. The compound of claim 8, wherein $NR^5R^6$ is $NH_2$, or a pharmaceutically acceptable salt thereof.

10. The compound of claim 1, wherein $R^2$ is $C_{1-6}$ alkyl that optionally is substituted with aryl that itself optionally is substituted with Cl, F or $CF_3$, or a pharmaceutically acceptable salt thereof.

11. The compound of claim 10, wherein the aryl is phenyl that optionally is substituted with Cl, or a pharmaceutically acceptable salt thereof.

12. The compound of claim 1, wherein $R^2$ is $C_{1-6}$ alkyl that optionally is substituted with heteroaryl, or a pharmaceutically acceptable salt thereof.

13. The compound of claim 12 wherein the heteroaryl is thiophene, or a pharmaceutically acceptable salt thereof.

14. The compound of claim 1, wherein $R^2$ is $C_{1-6}$ alkyl that optionally is substituted with a group selected from heterocycle and $NR^5R^6$, or a pharmaceutically acceptable salt thereof.

15. The compound of claim 14, wherein $R^5$ and $R^6$ are H, or a pharmaceutically acceptable salt thereof.

16. The compound of claim 1, wherein $R^3$ and $R^4$ are H or $CH_3$, or a pharmaceutically acceptable salt thereof.

17. The compound of claim 1, wherein $R^5$ and $R^6$ are H or $CH_3$, or a pharmaceutically acceptable salt thereof.

18. A composition comprising a compound of claim 1, or a pharmaceutically acceptable salt thereof, as an active ingredient and a pharmaceutically acceptable carrier or excipient.

19. The compound of claim 2, selected from the group consisting of:
[3-(6-Benzylamino-pyridin-2-yl)-1H-pyrazolo[3,4-d]pyrimidin-6-yl]-(2-piperidin-1-yl-ethyl)-amine;
[3-(6-Benzylamino-pyridin-2-yl)-1H-pyrazolo[3,4-d]pyrimidin-6-yl]-(2-morpholin-4-yl-ethyl)-amine;
{3-[6-(3-Chloro-benzylamino)-pyridin-2-yl]-1H-pyrazolo[3,4-d]pyrimidin-6-yl}-(2-morpholin-4-yl-ethyl)-amine;

{3-[6-(4-Chloro-benzylamino)-pyridin-2-yl]-1H-pyrazolo[3,4-d]pyrimidin-6-yl}-(2-morpholin-4-yl-ethyl)-amine;

N-[3-(6-Benzylamino-pyridin-2-yl)-1H-pyrazolo[3,4-d]pyrimidin-6-yl]-cyclohexane-1,4-diamine;

{3-[6-(2-Chloro-benzylamino)-pyridin-2-yl]-1H-pyrazolo[3,4-d]pyrimidin-6-yl}-(2-morpholin-4-yl-ethyl)-amine;

(2-Morpholin-4-yl-ethyl)-(3-{6-[(thiophen-3-ylmethyl)-amino]-pyridin-2-yl}-1H-pyrazolo[3,4-d]pyrimidin-6-yl)-amine;

N-(3-{6-[(Thiophen-3-ylmethyl)-amino]-pyridin-2-yl}-1H-pyrazolo[3,4-d]pyrimidin-6-yl)-cyclohexane-1,4-diamine; hydrochloride;

N-{3-[6-(3-Amino-1-phenyl-propylamino)-pyridin-2-yl]-1H-pyrazolo[3,4-d]pyrimidin-6-yl}-cyclohexane-1,4-diamine; hydrochloride;

N-{3-[6-(2-Amino-1-phenyl-ethylamino)-pyridin-2-yl]-1H-pyrazolo[3,4-d]pyrimidin-6-yl}-cyclohexane-1,4-diamine; hydrochloride; and N1-{6-[6-(2-Morpholin-4-yl-ethylamino)-1H-pyrazolo[3,4-d]pyrimidin-3-yl]-pyridin-2-yl}-1-phenyl-propane-1,3-diamine; hydrochloride;

or a pharmaceutically acceptable salt of any of the foregoing compounds.

20. The compound of claim 3, selected from the group consisting of

[3-(3-Benzylamino-phenyl)-1H-pyrazolo[3,4-d]pyrimidin-6-yl]-(2-morpholin-4-yl-ethyl)-amine;

{3-[3-(4-Chloro-benzylamino)-phenyl]-1H-pyrazolo[3,4-d]pyrimidin-6-yl}-(2-morpholin-4-yl-ethyl)-amine;

(2-Morpholin-4-yl-ethyl)-(3-{3-[(thiophen-3-ylmethyl)-amino]-phenyl}-1H-pyrazolo[3,4-d]pyrimidin-6-yl)-amine;

N-[3-(3-Benzylamino-phenyl)-1H-pyrazolo[3,4-d]pyrimidin-6-yl]-cyclohexane-1,4-diamine;

N-(3-{3-[(Thiophen-2-ylmethyl)-amino]-phenyl}-1H-pyrazolo[3,4-d]pyrimidin-6-yl)-cyclohexane-1,4-diamine;

(2-Morpholin-4-yl-ethyl)-(3-{3-[(thiophen-2-ylmethyl)-amino]-phenyl}-1H-pyrazolo[3,4-d]pyrimidin-6-yl)-amine;

N-{3-[3-(4-Chloro-benzylamino)-phenyl]-1H-pyrazolo[3,4-d]pyrimidin-6-yl}-cyclohexane-1,4-diamine;

N-{3-[3-(2-Chloro-benzylamino)-phenyl]-1H-pyrazolo[3,4-d]pyrimidin-6-yl}-cyclohexane-1,4-diamine;

{3-[3-(2-Chloro-benzylamino)-phenyl]-1H-pyrazolo[3,4-d]pyrimidin-6-yl}-(2-morpholin-4-yl-ethyl)-amine;

N-(3-{3-[(Thiophen-3-ylmethyl)-amino]-phenyl}-1H-pyrazolo[3,4-d]pyrimidin-6-yl)-cyclohexane-1,4-diamine;

N1-{3-[6-(2-Morpholin-4-yl-ethylamino)-1H-pyrazolo[3,4-d]pyrimidin-3-yl]-phenyl}-1-phenyl-propane-1,3-diamine; hydrochloride; and N-{3-[3-(3-Amino-1-phenyl-propylamino)-phenyl]-1H-pyrazolo[3,4-d]pyrimidin-6-yl}-cyclohexane-1,4-diamine; hydrochloride;

or a pharmaceutically acceptable salt of any of the foregoing compounds.

21. The compound of claim 4, selected from the group consisting of

[3-(2-Benzylamino-pyrimidin-4-yl)-1H-pyrazolo[3,4-d]pyrimidin-6-yl]-(2-morpholin-4-yl-ethyl)-amine; hydrochloride;

{3-[2-(3-Chloro-benzylamino)-pyrimidin-4-yl]-1H-pyrazolo[3,4-d]pyrimidin-6-yl}-(2-morpholin-4-yl-ethyl)-amine; hydrochloride;

{3-[2-(2-Chloro-benzylamino)-pyrimidin-4-yl]-1H-pyrazolo[3,4-d]pyrimidin-6-yl}-(2-morpholin-4-yl-ethyl)-amine; hydrochloride;

{3-[2-(4-Chloro-benzylamino)-pyrimidin-4-yl]-1H-pyrazolo[3,4-d]pyrimidin-6-yl}-(2-morpholin-4-yl-ethyl)-amine; hydrochloride;

N-(3-{2-[(Thiophen-3-ylmethyl)-amino]-pyrimidin-4-yl}-1H-pyrazolo[3,4-d]pyrimidin-6-yl)-cyclohexane-1,4-diamine; hydrochloride;

N-{3-[2-(2-Amino-1-phenyl-ethylamino)-pyrimidin-4-yl]-1H-pyrazolo[3,4-d]pyrimidin-6-yl}-cyclohexane-1,4-diamine; hydrochloride;

N-{3-[2-(3-Amino-1-phenyl-propylamino)-pyrimidin-4-yl]-1H-pyrazolo[3,4-d]pyrimidin-6-yl}-cyclohexane-1,4-diamine; hydrochloride;

N-[3-(2-Benzylamino-pyrimidin-4-yl)-1H-pyrazolo[3,4-d]pyrimidin-6-yl]-cyclohexane-1,4-diamine; hydrochloride;

N-{3-[2-(3-Chloro-benzylamino)-pyrimidin-4-yl]-1H-pyrazolo[3,4-d]pyrimidin-6-yl}-cyclohexane-1,4-diamine; hydrochloride;

N-{3-[2-(4-Chloro-benzylamino)-pyrimidin-4-yl]-1H-pyrazolo[3,4-d]pyrimidin-6-yl}-cyclohexane-1,4-diamine; hydrochloride;

1-(3-Chloro-phenyl)-N1-{4-[6-(2-morpholin-4-yl-ethylamino)-1H-pyrazolo[3,4-d]pyrimidin-3-yl]-pyrimidin-2-yl}-ethane-1,2-diamine; hydrochloride;

(2-Morpholin-4-yl-ethyl)-(3-{2-[(thiophen-3-ylmethyl)-amino]-pyrimidin-4-yl}-1H-pyrazolo[3,4-d]pyrimidin-6-yl)-amine; hydrochloride; and N-(3-{2-[2-Amino-1-(3-chloro-phenyl)-ethylamino]-pyrimidin-4-yl}-1H-pyrazolo[3,4-d]pyrimidin-6-yl)-cyclohexane-1,4-diamine; hydrochloride;

or a pharmaceutically acceptable salt of any of the foregoing compounds.

22. The compound of claim 4, selected from the group consisting of

N-(3-{2-[3-Amino-1-(3-chloro-phenyl)-propylamino]-pyrimidin-4-yl}-1H-pyrazolo[3,4-d]pyrimidin-6-yl)-cyclohexane-1,4-diamine; hydrochloride; and N1-{4-[6-(2-Morpholin-4-yl-ethylamino)-1H-pyrazolo[3,4-d]pyrimidin-3-yl]-pyrimidin-2-yl}-1-phenyl-propane-1,3-diamine; hydrochloride;

N1-{4-[6-(2-Morpholin-4-yl-ethylamino)-1H-pyrazolo[3,4-d]pyrimidin-3-yl]-pyrimidin-2-yl}-1-thiophen-3-yl-ethane-1,2-diamine; hydrochloride;

N1-{4-[6-(2-Morpholin-4-yl-ethylamino)-1H-pyrazolo[3,4-d]pyrimidin-3-yl]-pyrimidin-2-yl}-1-phenyl-ethane-1,2-diamine; hydrochloride;

N-{3-[2-(3-Trifluoromethyl-benzylamino)-pyrimidin-4-yl]-1H-pyrazolo[3,4-d]pyrimidin-6-yl}-cyclohexane-1,4-diamine; hydrochloride;

N-{3-[2-(3-Fluoro-benzylamino)-pyrimidin-4-yl]-1H-pyrazolo[3,4-d]pyrimidin-6-yl}-cyclohexane-1,4-diamine; hydrochloride;

{3-[2-(3-Chloro-benzylamino)-pyrimidin-4-yl]-1H-pyrazolo[3,4-d]pyrimidin-6-yl}-piperidin-4-yl-amine; hydrochloride;

N-{3-[2-(3-Chloro-benzylamino)-pyrimidin-4-yl]-1H-pyrazolo[3,4-d]pyrimidin-6-yl}-N',N'-dimethyl-ethane-1,2-diamine; hydrochloride;

{3-[2-(3-Chloro-benzylamino)-pyrimidin-4-yl]-1H-pyrazolo[3,4-d]pyrimidin-6-yl}-piperidin-4-ylmethyl-amine; hydrochloride;

N-{3-[2-(3-Chloro-benzylamino)-pyrimidin-4-yl]-1H-pyrazolo[3,4-d]pyrimidin-6-yl}-cyclohexane-1,4-diamine; hydrochloride;

{3-[2-(3-Chloro-benzylamino)-pyrimidin-4-yl]-1H-pyrazolo[3,4-d]pyrimidin-6-yl}-(2-pyrrolidin-1-yl-ethyl)-amine; hydrochloride;

2-{3-[2-(3-Chloro-benzylamino)-pyrimidin-4-yl]-1H-pyrazolo[3,4-d]pyrimidin-6-ylamino}-ethanol; hydrochloride;

{3-[2-(3-Chloro-benzylamino)-pyrimidin-4-yl]-1H-pyrazolo[3,4-d]pyrimidin-6-yl}-(2-piperazin-1-yl-ethyl)-amine; hydrochloride; and {3-[2-(3-Chloro-benzylamino)-pyrimidin-4-yl]-1H-pyrazolo[3,4-d]pyrimidin-6-yl}-(2-piperazin-1-yl-ethyl)-amine; hydrochloride;

or the pharmaceutically acceptable salts of any of the foregoing compounds.

* * * * *

UNITED STATES PATENT AND TRADEMARK OFFICE
CERTIFICATE OF CORRECTION

PATENT NO. : 8,362,023 B2
APPLICATION NO. : 13/347718
DATED : January 29, 2013
INVENTOR(S) : Liu et al.

It is certified that error appears in the above-identified patent and that said Letters Patent is hereby corrected as shown below:

In the Claims:

Claim 6, column 122, line 21, delete "claim 5" and insert -- claim 1 --

Signed and Sealed this
Fourth Day of June, 2013

Teresa Stanek Rea
*Acting Director of the United States Patent and Trademark Office*